(12) United States Patent
Ledbetter et al.

(10) Patent No.: US 8,106,161 B2
(45) Date of Patent: *Jan. 31, 2012

(54) BINDING DOMAIN-IMMUNOGLOBULIN FUSION PROTEINS

(75) Inventors: Jeffrey A. Ledbetter, Shoreline, WA (US); Martha S. Hayden-Ledbetter, Shoreline, WA (US)

(73) Assignee: Emergent Product Development Seattle, LLC, Seattle, WA (US)

(*) Notice: Subject to any disclaimer, the term of this patent is extended or adjusted under 35 U.S.C. 154(b) by 1242 days.

This patent is subject to a terminal disclaimer.

(21) Appl. No.: 11/088,693

(22) Filed: Mar. 23, 2005

(65) Prior Publication Data

US 2005/0202028 A1 Sep. 15, 2005

Related U.S. Application Data

(63) Continuation of application No. 10/053,530, filed on Jan. 17, 2002, now abandoned.

(60) Provisional application No. 60/367,358, filed on Jan. 17, 2001.

(51) Int. Cl.
*C07K 16/00* (2006.01)

(52) U.S. Cl. .................. 530/387.1; 424/178.1

(58) Field of Classification Search .................. None
See application file for complete search history.

(56) References Cited

U.S. PATENT DOCUMENTS

| | | | |
|---|---|---|---|
| 4,704,692 A | 11/1987 | Ladner .................. 364/496 |
| 4,816,567 A | 3/1989 | Cabilly et al. ................ 530/387 |
| 4,906,562 A | 3/1990 | Hellstrom et al. ................ 435/7 |
| 4,935,495 A | 6/1990 | Hellstrom et al. ............ 530/387 |
| 4,946,778 A | 8/1990 | Ladner et al. ................ 435/69.6 |
| 5,091,177 A | 2/1992 | Hellstrom et al. |
| 5,098,833 A | 3/1992 | Lasky et al. |
| 5,225,539 A | 7/1993 | Winter |
| 5,260,203 A | 11/1993 | Ladner et al. |
| 5,434,131 A | 7/1995 | Linsley et al. |
| 5,455,030 A | 10/1995 | Ladner et al. |
| 5,500,362 A | 3/1996 | Robinson et al. ............ 435/7.23 |
| 5,521,288 A | 5/1996 | Linsley et al. |
| 5,530,101 A | 6/1996 | Queen et al. |
| 5,580,756 A | 12/1996 | Linsley et al. |
| 5,585,089 A | 12/1996 | Queen et al. ................ 424/133.1 |
| 5,597,707 A | 1/1997 | Marken et al. |
| 5,605,690 A | 2/1997 | Jacobs et al. |
| 5,637,481 A | 6/1997 | Ledbetter et al. |
| 5,645,835 A | 7/1997 | Fell, Jr. et al. |
| 5,677,425 A * | 10/1997 | Bodmer et al. ............ 530/387.1 |
| 5,693,762 A | 12/1997 | Queen et al. ................ 530/387.3 |
| 5,709,859 A | 1/1998 | Aruffo et al. |
| 5,714,147 A | 2/1998 | Capon et al. |
| 5,736,137 A | 4/1998 | Anderson et al. |
| 5,770,197 A | 6/1998 | Linsley et al. |
| 5,773,253 A | 6/1998 | Linsley et al. |
| 5,776,456 A | 7/1998 | Anderson et al. |
| 5,795,572 A | 8/1998 | Diegel et al. |
| 5,807,734 A | 9/1998 | Diegel et al. |
| 5,844,093 A | 12/1998 | Kettleborough et al. |
| 5,844,095 A | 12/1998 | Linsley et al. |
| 5,869,049 A | 2/1999 | Noelle et al. |
| 5,869,620 A | 2/1999 | Whitlow et al. ............ 530/387.3 |
| 5,876,718 A | 3/1999 | Noelle et al. |
| 5,876,950 A | 3/1999 | Siadak et al. |
| 5,888,773 A | 3/1999 | Jost et al. ................ 435/69.6 |
| 5,892,019 A | 4/1999 | Schlom et al. ............ 536/23.53 |
| 5,916,560 A | 6/1999 | Larsen et al. |
| 5,955,315 A | 9/1999 | Lee et al. ................ 435/69.52 |
| 6,015,695 A | 1/2000 | Casterman et al. .......... 435/69.6 |
| 6,074,644 A | 6/2000 | Pastan et al. |
| 6,087,329 A | 7/2000 | Armitage et al. |
| 6,090,914 A | 7/2000 | Linsley et al. |
| 6,120,767 A | 9/2000 | Robinson et al. .......... 424/133.1 |
| 6,147,203 A | 11/2000 | Pastan et al. |
| 6,150,584 A * | 11/2000 | Kucherlapati et al. |
| 6,180,370 B1 | 1/2001 | Queen et al. ................ 435/69.6 |
| 6,194,551 B1 | 2/2001 | Idusogie et al. |
| 6,264,951 B1 * | 7/2001 | Armitage et al. |
| 6,284,536 B1 * | 9/2001 | Morrison et al. |
| 6,306,393 B1 | 10/2001 | Goldenberg ................ 424/141.1 |
| 6,312,692 B1 | 11/2001 | Noelle et al. |
| 6,352,694 B1 | 3/2002 | June et al. ................ 424/93.71 |
| 6,376,459 B1 | 4/2002 | Aruffo et al. |
| 6,384,198 B1 | 5/2002 | Diegel et al. |
| 6,403,769 B1 | 6/2002 | Larochelle et al. ........ 530/387.3 |

(Continued)

FOREIGN PATENT DOCUMENTS

EP 0274394 A2 7/1988

(Continued)

OTHER PUBLICATIONS

Aldersberg Ric Clin. Lab. 6(3):191-205 (1976).*
Wu et al (Protein Engineering 14(12):1025-1033, 2001).*
Shan et al (The Journal of immunology, 162:6589-6595, 1999).*
Liu et al (The Journal of Immunology, 139(10):3521-3526, 1987).*
Dall'Acqua et al., The Journal of Immunology, 177:pp. 1129-1138, 2006.*
Rudikoff et al , PNAS 79:1979, 1982.*
Paul, Fundamental Immunology, Raven Press, Chapter 8, p. 242, 1993.*
Cruse et al, Illustrated Dictionary of Immunology, CRC Press, p. 157, 1995.*
Fell et al. The Journal of Biological Chemistry, 267(22):15552-15558, 1992.*

(Continued)

*Primary Examiner* — Laura B Goddard
*Assistant Examiner* — Meera Natarajan
(74) *Attorney, Agent, or Firm* — Cooley LLP

(57) ABSTRACT

The invention relates to novel binding domain-immunoglobulin fusion proteins that feature a binding domain for a cognate structure such as an antigen, a counterreceptor or the like, a hinge region polypeptide having either zero or one cysteine residue, and immunoglobulin CH2 and CH3 domains, and that are capable of ADCC and/or CDC while occurring predominantly as monomeric polypeptides. The fusion proteins can be recombinantly produced at high expression levels. Also provided are related compositions and methods, including immunotherapeutic applications.

23 Claims, 26 Drawing Sheets

U.S. PATENT DOCUMENTS

| | | |
|---|---|---|
| 6,410,319 B1 | 6/2002 | Raubitschek et al. |
| 6,444,792 B1 | 9/2002 | Gray et al. |
| 6,472,510 B1 | 10/2002 | Aruffo et al. |
| 6,482,919 B2 | 11/2002 | Ledbetter et al. |
| 6,515,110 B1 | 2/2003 | Whitlow et al. ......... 530/387.3 |
| 6,586,428 B2 | 7/2003 | Geroni et al. ............. 514/231.5 |
| 6,623,940 B1 | 9/2003 | Ledbetter et al. |
| 6,641,809 B1 | 11/2003 | Linsley et al. |
| 6,696,290 B2 | 2/2004 | Fitzpatrick et al. ........... 435/325 |
| 6,815,540 B1 | 11/2004 | Plückthun et al. ........ 536/23.53 |
| 6,893,625 B1 | 5/2005 | Robinson et al. ........... 424/1.49 |
| 7,074,403 B1 | 7/2006 | Goldenberg et al. ...... 424/130.1 |
| 7,148,321 B2 | 12/2006 | Gillies et al. .................. 530/300 |
| 7,754,208 B2 | 7/2010 | Ledbetter et al. ......... 424/133.1 |
| 7,754,209 B2 | 7/2010 | Ledbetter et al. ......... 424/133.1 |
| 7,829,084 B2 | 11/2010 | Ledbetter et al. ......... 424/133.1 |
| 2001/0044135 A1 | 11/2001 | Stahl et al. |
| 2002/0004587 A1 | 1/2002 | Miller et al. ................ 530/388.8 |
| 2002/0031510 A1 | 3/2002 | Larsen et al. |
| 2002/0039557 A1 | 4/2002 | White |
| 2002/0155604 A1 | 10/2002 | Ledbetter et al. |
| 2003/0044423 A1* | 3/2003 | Gillies et al. |
| 2003/0088074 A1 | 5/2003 | Hamers et al. ............. 530/387.1 |
| 2003/0118592 A1 | 6/2003 | Ledbetter et al. ......... 424/178.1 |
| 2003/0133930 A1 | 7/2003 | Goldenberg et al. ...... 424/141.1 |
| 2003/0133939 A1 | 7/2003 | Ledbetter et al. ......... 424/178.1 |
| 2003/0219433 A1 | 11/2003 | Hansen et al. |
| 2003/0219436 A1 | 11/2003 | Ledbetter et al. |
| 2003/0219446 A1 | 11/2003 | Linsley et al. |
| 2003/0219876 A1 | 11/2003 | Ledbetter et al. |
| 2004/0058445 A1 | 3/2004 | Ledbetter et al. |
| 2005/0084933 A1 | 4/2005 | Schilling et al. ............. 435/69.1 |
| 2005/0136049 A1* | 6/2005 | Ledbetter et al. ......... 424/132.1 |
| 2005/0175614 A1 | 8/2005 | Ledbetter et al. ......... 424/145.1 |
| 2005/0180970 A1 | 8/2005 | Ledbetter et al. ......... 424/143.1 |
| 2005/0186216 A1 | 8/2005 | Ledbetter et al. ......... 424/155.1 |
| 2005/0202012 A1 | 9/2005 | Ledbetter et al. ......... 424/144.1 |
| 2005/0202023 A1 | 9/2005 | Ledbetter et al. ......... 424/155.1 |
| 2005/0202028 A1 | 9/2005 | Ledbetter et al. ......... 424/178.1 |
| 2005/0202534 A1 | 9/2005 | Ledbetter et al. ............. 435/69.1 |
| 2005/0238646 A1 | 10/2005 | Ledbetter et al. ......... 424/144.1 |
| 2007/0059306 A1 | 3/2007 | Grosmaire et al. ........ 424/144.1 |
| 2007/0237779 A1 | 10/2007 | Ledbetter et al. ......... 424/155.1 |
| 2008/0213273 A1 | 9/2008 | Burge ......................... 424/141.1 |
| 2008/0279850 A1 | 11/2008 | Brady et al. ............... 424/133.1 |
| 2009/0088346 A1 | 4/2009 | Enzelberger et al. ............ 506/17 |
| 2009/0148447 A1 | 6/2009 | Ledbetter et al. ......... 424/134.1 |
| 2009/0175867 A1 | 7/2009 | Thompson et al. ........ 424/135.1 |
| 2009/0196870 A1 | 8/2009 | Ledbetter et al. ......... 424/133.1 |
| 2009/0214539 A1 | 8/2009 | Grosmaire et al. ........ 424/135.1 |
| 2009/0274692 A1 | 11/2009 | Tan et al. ................... 424/134.1 |
| 2010/0034820 A1 | 2/2010 | Ledbetter et al. ......... 424/134.1 |
| 2010/0135900 A1 | 6/2010 | Cerveny et al. ............. 424/1.11 |
| 2010/0203052 A1 | 8/2010 | Ledbetter et al. ......... 424/134.1 |
| 2010/0279932 A1 | 11/2010 | Ledbetter et al. ............. 514/7.3 |
| 2011/0033483 A1 | 2/2011 | Thompson et al. ........ 424/179.1 |
| 2011/0091461 A1 | 4/2011 | Ledbetter et al. ......... 424/134.1 |
| 2011/0105729 A1 | 5/2011 | Ledbetter et al. ......... 530/387.3 |

FOREIGN PATENT DOCUMENTS

| | | |
|---|---|---|
| EP | 0555880 | 8/1993 |
| EP | 0586002 | 3/1994 |
| EP | 0757099 | 7/1995 |
| EP | 0682039 | 11/1995 |
| EP | 1186300 | 3/2002 |
| WO | WO 88/04936 A1 | 7/1988 |
| WO | 89/07142 A1 | 8/1989 |
| WO | WO-8907142 | 8/1989 |
| WO | 91/04329 A1 | 4/1991 |
| WO | 91/13166 A1 | 9/1991 |
| WO | WO-9200092 | 1/1992 |
| WO | WO-9221755 | 12/1992 |
| WO | WO-9300431 | 1/1993 |
| WO | 94/04678 A1 | 3/1994 |
| WO | WO-9405690 | 3/1994 |
| WO | 94/25591 A1 | 11/1994 |
| WO | WO-9509917 | 4/1995 |
| WO | 96/34103 A1 | 10/1996 |
| WO | WO 98/02462 | 1/1998 |
| WO | WO-9942077 | 8/1999 |
| WO | 99/43713 A1 | 9/1999 |
| WO | 99/57266 A2 | 11/1999 |
| WO | 00/27885 A1 | 5/2000 |
| WO | WO-0044777 | 8/2000 |
| WO | 00/69913 A1 | 11/2000 |
| WO | WO 02/056910 | 7/2002 |
| WO | WO 02/072605 A2 | 9/2002 |
| WO | 03/083069 A2 | 10/2003 |
| WO | 2004/003019 A2 | 1/2004 |
| WO | 2005/017148 A1 | 2/2005 |
| WO | 2005/037989 A2 | 4/2005 |
| WO | 2007/014238 A2 | 2/2007 |
| WO | 2007/014278 A2 | 2/2007 |
| WO | 2007/146968 A2 | 12/2007 |
| WO | 2009/023386 A2 | 2/2009 |
| WO | 2009/126944 A1 | 10/2009 |
| WO | 2010/057047 A1 | 5/2010 |

OTHER PUBLICATIONS

Tan et al. Proc. Natl. Acad. Sci. USA, 87:162-166, Jan. 1990.*
Dall'Acqua et al. The Journal of Immunology, 177:1129-1138, 2006.*
Aicher et al., "Characterization of Human Inducible Costimulator Ligand Expression and Function," *The Journal of Immunology* 164:4689-4696, 2000.
Batra et al., "Single Chain Immunotoxins Directed at the Human Transferrin Receptor Containing *Pseudomonas* Exotoxin A or Diphtheria Toxin: Anti-TFR(Fv)-PE40 and DT388-Anti-TFR(Fv)," *Molecular and Cellular Biology* 11(4):2200-2205, 1991.
Beiske et al., "Triggering of Neoplastic B Cells Via Surface IgM and the Cell Surface Antigens CD20 and CDw40. Responses Differ from Normal Blood B Cells and are Restricted to Certain Morphologic Subsets," *Int J Cancer* 42:521-8, 1988.
Brekke et al., "The Structural Requirements for Complement Activation by IgG: Does it Hinge on the Hinge?" *Immunol. Today* 16:85-90, 1995.
Brown et al., "Treatment of B-Cell Lymphomas with Anti-Idiotype Antibodies Alone and in Combination with Alpha Interferon," *Blood* 73(3):651-61, 1989.
Burke et al., "Radioimmunotherapy for Acute Leukemia," *Cancer Control* 9:106-113, 2002.
Carter, "Improving the Efficacy of Antibody-Based Cancer," *Nature* 1(2):118-129, 2001.
Chaudhary et al., "A Recombinant Immunotoxin Consisting of Two Antibody Variable Domains Fused to *Pseudomonas* Exotoxin," *Nature* 339:394-397, 1989.
Clark et al., "Activation of Human B Cells Mediated Through Two Distinct Cell Surface Differentiation Antigens, Bp35 and Bp50," *Proc. Natl. Acad. Sci. USA* 83:4494-4498, 1986.
Clark et al., "Structure, Function, and Genetics of Human B Cell-Associated Surface Molecules," *Advances in Cancer Research* 52:81-149, 1989.
Coloma et al., "The Hinge as a Spacer Contributes to Covalent Assembly and is Required for Function of IgG," *J. Immunol.* 158(2):733-40, 1997.
Damle et al., "Direct Helper T Cell-Induced B Cell Differentiation Involves Interaction Between T Cell Antigen CD28 and B Cell Activation Antigen B7," *Eur. J. Immunology* 21:1277-1282, 1991.
Davies et al., "Camelising Human Antibody Fragments: NMR Studies on VH Domains," *FEBS Letters* 339:285-290, 1994.
Davis et al., "High Level Expression in Chinese Hamster Ovary Cells of Soluble Forms of CD4 T Lymphocyte Glycoprotein Including Glycosylation Variants," *The Journal of Biological Chemistry* 265(18):10410-10418, 1990.
Desmyter et al., "Crystal Structure of a Camel Single Domain VH Antibody Fragment in Complex with Lysozyme," *Nature Structural Biology* 3(9):803-811, 1996.
Dietsch et al., "Bispecific Receptor Globulins, Novel Tools for the Study of Cellular Interactions," *Journal of Immunological Methods*, 162:123-132, 1993.
Dietsch et al., "Coengagement of CD2 with LFA-1 or VLA-4 by Bispecific Ligand Fusion Proteins Primes T Cells to Respond More Effectively to T Cell Receptor-Dependant Signals," *Journal of Leukocyte Biology* 56:444-452, 1994.

Dillman et al., "Continuous Infusion of T101 Monoclonal Antibody in Chronic Lymphocytic Leukemia and Cutaneous T-Cell Lymphoma," *Journal of Biological Response Modifiers* 5(5):394-410, 1986.

Dorai et al., "Role of Inter-Heavy and Light Chain Disulfide Bonds in the Effector Functions of Human Immunoglobulin IgG1," *Mol. Immunology* 29:1487-1491, 1992.

Duncan et al., "The Binding Site for Clq on IgG," *Nature* 322:738-740, 1988.

Durie et al., "Prevention of Collagen-Induced Arthritis with an Antibody to gp39, the Ligand for CD40," *Science* 261:1328-1330, 1993.

Einfeld et al., "Molecular Cloning of the Human B Cell CD20 Receptor Predicts a Hydrophobic Protein with Multiple Transmembrane Domains," *EMBO Journal* 7:711-717, 1988.

Fell et al., "Genetic Construction and Characterization of a Fusion Protein Consisting of a Chimeric F(ab') with Specificity for Carcinomas and Human IL-2," *Journal of Immunology* 146(7):2446-2452, 1991.

Filpula et al., "Single-Chain Fv Designs for Protein, Cell and Gene Therapeutics," *Exp. Opin. Ther. Patents* 9(3):231-245, 1991.

Funakoshi et al., "Differential in Vitro and in Vivo Antitumor Effects Mediated by Anti-CD40 and Anti-CD20 Monoclonal Antibodies Against Human B-Cell Lymphomas," *Journal of Immunotherapy* 19(2):93-101, 1996.

Funakoshi et al., "Inhibition of Human B-Cell Lymphoma Growth by CD40 Stimulation," *Blood* 83(10):2787-2794, 1994.

Genbank Accession No. L07414, Apr. 27, 1993.
Genbank Accession No. M62541, Jul. 26, 1993.
Genbank Accession No. M62542, Apr. 27, 1993.
Genbank Accession No. M83312, Sep. 23, 1996.
Genbank Accession No. M84371, Jul. 17, 1995.
Genbank Accession No. U15637, Mar. 8, 2002.
Genbank Accession No. X14046, Sep. 12, 1993.
Genbank Accession No. X53517, Feb. 17, 1992.
Genbank Accession No. X65453, Apr. 26, 2001.
Genbank Accession No. X67878, Jun. 6, 1997.
Genbank Accession No. X96710, Feb. 13, 1997.
Genbank Accession No. Y10507, Sep. 4, 1997.

Gillies et al., "Antigen Binding and Biological Activities of Engineered Mutant Chimeric Antibodies with Human Tumor Specifities," *Hum. Antibodies Hybridomas* 1:47-54, 1990.

Gilliland et al., "Rapid and Reliable Cloning of Antibody Variable Regions and Generation of Recombinant Single Chain Antibody Fragments," *Tissue Antigens* 47:1-20, 1996.

Hayden et al., "Antibody Engineering," *Curr. Opin. Immuno.* 9:201-212, 1997.

Hayden et al., "Costimulation by CD28 sFv Expressed on the Tumor Cell Surface or as a Soluable Bispecific Molecule Targeted to the L6 Carcinoma Antigen," *Tissue Antigens* 48:242-254, 1996.

Hayden et al., "Single-Chain Mono- and Bispecific Antibody Derivatives with Novel Biological Properties and Antitumor Activity from a COS Cell Transient Expression System," *Thera. Immuno.*, 1:3-15, 1994.

Hekman et al., "Initial Experience with Treatment of Human B Cell Lymphoma with Anti-CD19 Monoclonal Antibody," *Cancer Immunol. Immunother.* 32:364-372, 1991.

Hollenbaugh et at., "The Human T Cell Antigen gp39, a Member of the TNF Gene Family, Is a Ligand for the CD40 Receptor: Expression of a Soluble Form of gp39 with B Cell Costimulatory Activity," *EMBO Journal* 11:4313-4321, 1992.

Hu et al., "Minibody: A Novel Engineered Anti-Carcinoembryonic Antigen Antibody Fragment (Single Chain Fv-CH3) Which Exhibits Rapid, High-Level Targeting of Xenografts," *Cancer Res.* 56(13):3055-3061, 1996.

Hudson et al., "Recombinant Antibodies: A Novel Approach to Cancer Diagnostics and Therapy," *Exp. Opin. Invest. Drugs* 9(6):1231-1242, 2000.

Hudson, "Recombinant Antibody Fragments," *Current Opinions in Biotechnology* 9:395-402, 1998.

Huston et al., "Protein Engineering of Antibody Binding Sites: Recovery of Specific Activity in an Anti-Digoxin Single-Chain Fv Analogue Produced in *Escherichia coli*," *Proc. Natl. Acad. Sci. USA* 85:5879-5883, 1988.

International Search Report from PCT/US02/01487 dated May 9, 2002.

Written Opinion from PCT/US02/01487 dated Nov. 20, 2002.

Isenman et al., "Correlation Between the Exposure of Aromatic Chromophores at the Surface of the Fc Domains of Immunoglobulin G and Their Ability to Bind Complement," *Biochemistry* 16:233-240, 1977.

Jost et al., "Mammalian Expression and Secretion of Functional Single-Chain Fv Molecules," *The Journal of Biological Chemistry* 269(42):26267-26273, 1994.

Kaminski et al., "Radioimmunotherapy of B-Cell Lymphoma with [131I] Anti-B1 (Anti-CD20) Antibody," *The New England Journal of Medicine* 329(7):459-465, 1993.

Kato of al., "A Conformational Change in the Fc Precludes the Binding of Two Fcγ y Receptor Molecules to One IgG," *Immunology Today* 21(7):310-312, 2000.

Klein et al., "Expression of Biological Effector Functions by Immunoglobulin G Molecules Lacking the Hinge Region," *Proc. Natl. Acad. Sci. USA* 78:524-528, 1981.

Koolwijk et al., "Interaction Between Hybrid Mouse Monoclonal Antibodies and the Human High-Affinity IgG FcR, huFcγγRI, on U937," *The Journal of Immunology* 143(5)1656-1662, 1989.

Kortt et al., "Dimeric and Trimeric Antibodies: High Avidity scFvs for Cancer Targeting," *Biomole. Eng.* 18:95-108, 2001.

Ledbetter et al., "Augmentation of Normal and Malignant B Cell Proliferation by Monoclonal Antibody to the B Cell-Specific Antigen BP50 (CDW40)," *The Journal of Immunology* 138(3):788-794, 1987.

Lee et al., "Generation and Characterization of a Novel Single-Gene-Encoded Single-Chain Immunoglobulin Molecule with Antigen Binding Activity and Effector Functions," *Molecular Immunology* 36:61-71, 1999.

Li et al., "Single-Chain Antibodies Against Human Insulin-Like Growth Factor I Receptor: Expression, Purification and Effect on Tumor Growth," *Cancer Immunol. Immunother.* 49:243-252, 2000.

Liu et al., "Production of a Mouse-Human Chimeric Monoclonal Antibody to CD20 with Potent Fc-Dependent Biologic Activity," *The Journal of Immunology* 139(10):3521-3526, 1987.

Maloney et al., "IDEC=C2B8: Results of a Phase I Multiple-Dose Trial in Patients with Relapsed Non-Hodgkin's Lymphoma," *Journal of Clinical Oncology* 15(10): 3266-3274, 1997.

Maloney et al., "IDEC-C2B8 (Rituximab) Anti-CD20 Monoclonal Antibody Therapy in Patients with Relapsed Low-Grade Non-Hodgkin's Lymphoma," *Blood* 90(6):2188-2195, 1997.

McLaughlin et al., "IDEC-C2B8 Anti-CD20 Antibody: Final Report on a Phase III Pivotal Trial in Patients (PTS) with Relapsed Low-Grade or Follicular Lymphoma (LG/F NHL)," *Blood* 88(*Abstract Suppl. 1*):90a, Abstract 349, 1996.

Michaelsen et al., "Antibody Dependent Cell-Mediated Cytotoxicity Induced by Chimeric Mouse-Human IgG Subclasses and IgG3 Antibodies with Altered Hinge Region," *Mol. Immunol.* 29:319-326, 1992.

Michaelsen et al., "Enhancement of Complement Activation and Cytolysis of Human IgG3 by Deletion of Hinge Exons," *Scand. J. Immunol.* 32:517-528, 1990.

Michaelsen et al., "One Disulfide Bond in Front of the Second Heavy Chain Constant Region is Necessary and Sufficient for Effector Functions of Human IgG3 without a Genetic Hinge," *Proc. Natl. Acad. Sci. USA* 91:9243-9247, 1994.

Multani et al., "Monoclonal Antibody-Based Therapies for Hematologic Malignancies," *Journal of Clinical Oncology* 16(11):3691-3710, 1998.

Nikula et al., "Impact of the High Tyrosine Fraction in Complementarity Determining Regions: Measured and Predicted Effects of Radioiodination on IgG Immunoreactivity," *Mol. Immunol.* 32: 865-871, 1995.

Park et al., "Generation and Characterization of a Novel Tetravalent Bispecific Antibody that Binds to Hepatitis B Virus Surface Antigens," *Molecular Immunology* 37:1123-1130, 2000.

Pawson et al., "Treatment of T-Cell Prolymphocytic Leukemia with Human CD52 Antibody," *Journal of Clinical Oncology 15*(7) 2667-2672, 1997.

Press et al, "Radiolabeled-Antibody Therapy of B-Cell Lymphoma with Autologous Bone Marrow Support," *The New England Journal of Medicine 329*(17): 1219-1224, 1993.

Press et al., "Monoclonal Antibody 1F5 (Anti-CD20) Serotherapy of Human B Cell Lymphomas," *Blood 69*(2):584-591, 1987.

Radaev et al., "Recognition of IgG by Fcγ Receptor," *The Journal of Biological Chemistry 276*(19)16478-16483, 2001.

Radaev et al., "The Structure of a Human Type III Fcγ Receptor in Complex with Fc," *The Journal of Biological Chemistry 276*(19):16469-16477, 2001.

Redpath et al., "The Influence of the Hinge Region Length in Binding of Human IgG to Human Fcγ Receptors," *Hum. Immunol. 59*:720-727, 1998.

Rudikoff et al., "Single Amino Acid Substitution Altering Antigen-binding Specificity", *PNAS 79*:1979, 1982.

Scheinberg et al., "A Phase I Toxicity, Pharmacology, and Dosimetry Trial of Monoclonal Antibody OKB7 in Patients with Non-Hodgkin's Lymphoma: Effects of Tumor Burden and Antigen Expression," *Journal of Clinical Oncology 8*(5):792-803, 1990.

Segal et al., "Introduction: Bispecific Antibodies," *Journal of Immunological Methods 248*:1-6, 2001.

Sensel et al., "Engineering Novel Antibody Molecules," *Clinical Immunology 65*:129-158, 1997.

Shan et al., "Apoptosis of Malignant Human B Cells by Ligation of CD20 with Monoclonal Antibodies," *Blood 91*(5):1644-1652, 1998.

Shan et al., "Characterization of scFv-Ig Constructs Generated from the Anti-CD20 mAb1F5 Using Linker Peptides of Varying Lengths," *The Journal of Immunology 162*(11):6589-6595, 1999.

Shin et al., "Genetically-Engineered Antibodies: Tools for the Study of Diverse Properties of the Antibody Molecule," *Immunological Reviews 130*:87-107, 1992.

Shin et al., "Hybrid Antibodies," *Intern. Rev. Immunol. 10*:177-186, 1993.

Shu et al., "Secretion of a Single-Gene-Encoded Immunoglobulin from Myeloma Cells," *Proc. Natl. Acad. Sci. USA 90*:7995-7999, 1993.

Smellie et al., "Radioimmunotherapy of Breast Cancer Xenografts with Monoclonal Antibody ICR12 Against c-erbB2 p185: Comparison of Iodogen and N-succinimidyl 4-methyl-3-(tri-n-butylstannyl)benzoate Radioiodination Methods," *Cancer Res.* 55: 5842s-5846s, 1995.

Sondermann et al., "The 3.2-Å Crystal Structure of the Human IgG1 Fragment-FcγRIII Complex," *Nature 406*:267-273, 2000.

Souriau et al., "Recombinant Antibodies for Cancer Diagnosis and Therapy." *Expert Opin. Biol. Ther.* 3(2):305-318, 2003.

Sporici et al., "ICOS Ligand Costimulation is Required for T-Cell Encephalitogenicity," *Clinical Immunology 100*(3):277-288, 2001.

Tan et al., "Influence of the Hinge Region on Complement Activation, C1 q Binding, and Segmental Flexibility in Chimeric Human Immunoglobulins," *PNAS, USA 87*(1):162-6, 1990.

Tao et al., "Role of Carbohydrate in the Structure and Effector Functions Mediated by the Human IgG Constant Region," *J. Immunol.* 143(8):2595-2601, 1989.

Thommesen, et al., "Lysine 322 in the Human IgG3 CH2 Domain is Crucial for Antibody Dependent Complement Activation," *Mol. Immunol.* 37:995-1004, 2000.

Traunecker et al., "Bispecific Single Chain Molecules (Janusins) Target Cytotoxic Lymphocytes on HIV Infected Cells," *EMBO Journal 10*:3655-3659, 1991.

Van den Abbeele et al., "Antigen-Binding Site Protection During Radiolabeling Leads to a Higher Immunoreactive Fraction," *J. Nucl. Med.* 32:116-122, 1991.

Vlasveld et al., "Treatment of Low-Grade Non-Hodgkin's Lymphoma with Continuous Infusion of Low-Dose Recombinant Interleukin-2 in combination with the B-Cell-Specific Monoclonal Antibody CLB-CD19," *Cancer Immunolo. Immunother.* 40:37-47, 1995.

Walker et al., "Aglycosylation of Human IgG1 and IgG3 Monoclonal Antibodies Can Eliminate Recognition by Human Cells Expressing Fc Gamma RI and/or Fc Gamma RII Receptors," *Biochem. J.* 259(2):347-53, 1989.

White et al., "Activation of Dense Human Tonsilar B Cells. Induction of c-myc Gene Expression Via Two Distinct Signal Transduction Pathways," *The Journal of Immunology 146*(3):846-859, 1993.

Wu et al., "Multimerization of a Chimeric Anti-CD20 Single-Chain Fv-Fc Fusion Protein Is Mediated Through Variable Domain Exchange," *Protein Eng.* 14(12):1025-1033, 2001.

Yokota et al., "Rapid Tumor Penetration of a Single-Chain Fv and Comparison with Other Immunoglobulin Forms," *Cancer Research* 52:3402-3408, 1992.

Zhorov et al., "Oxidative Iodination of Rabbit IgG: Localization of the Label in the Fc Fragment and Modification Effects," *Biokhimiia* 56:828-838, 1991.

Anderson et al., "Targeted anti-cancer therapy using rituximab, a chimaeric anti-CD20 antibody (IDEC-C2B8) in the treatment of non-Hodgkin's B-cell lymphoma," *Biochem. Soc. Trans.*, 25: 705-708 (1997).

International Preliminary Examination Report for corresponding PCT/US02/01487, dated Feb. 6, 2003.

Martin et al., "Efficient neutralization and disruption of rhinovirus by chimeric ICAM-1/immunoglobulin molecules," J. Virol., 67:3561-3568 (1993).

Munoz et al., "The CH1 domain of IgG is not essential for C3 covalent binding: importance of the other constant domains as targets for C3," *International Immunology*, 10:97-106 (1998).

Office Action from corresponding U.S. Appl. No. 10/053,530, dated Dec. 5, 2007.

Office Action from corresponding U.S. Appl. No. 10/053,530, dated Apr. 19, 2007.

Office Action from corresponding U.S. Appl. No. 10/053,530, dated Mar. 23, 2007.

Office Action from corresponding U.S. Appl. No. 10/053,530, dated Jan. 17, 2006.

Office Action from corresponding U.S. Appl. No. 10/053,530, dated Mar. 1, 2005.

Office Action from corresponding U.S. Appl. No. 10/053,530, dated Aug. 27, 2004.

Office Action from corresponding U.S. Appl. No. 10/053,530, dated Jan. 1, 2004.

Office Action from corresponding U.S. Appl. No. 10/053,530, dated May 22, 2003.

Stevenson et al., "Mechanisms in removal of tumor by antibody," Cell Biophysics, 24/25: 45-50 (1994).

Wang et al., "Human single-chain FV immunoconjugates targeted to a melanoma-associated chondroitin sulfate proteoglycan mediate specific lysis of human melanoma cells by natural killer cells and complement," *Proc. Natl. Acad. Sci. USA*, 96: 1627-1632 (1999).

Braslawsky et al., "Adriamycin(hydrazone)-antibody conjugates require internalization and intracellular acid hydrolysis for antitumor activity," *Cancer Immunol Immunother* 33: 367-374, 1991.

Clark et al., "Role of the Bp35 cell surface polypeptide in human B-cell activation," *Proc. Natl. Acad. Sci. USA* 82: 1766-1770, Mar. 1985.

Ledbetter et al., "B1.2 Monoclonal antibodies to a new gp40-45 (CD37) B-cell-associated cluster group modulate B-cell proliferation," in *Leucocyte Typing III: White Cell Differentiation Antigens*, A. J. McMichael, ed., International Workshop and Conference on Human Leucocyte Differentiation Antigens (3rd, 1986), Oxford University Press, Oxford, England, pp. 339-340.

Linsley et al., "T-cell antigen CD28 mediates adhesion with B cells by interacting with activation antigen B7/BB-1," *Proc. Natl. Acad. Sci. USA* 87: 5031-5035, Jul. 1990.

Pallesen et al., "B1.1 The expression of the 40-45 kDa pan-B cluster (CD37) in normal human tissues and in haematopoietic neoplasms as defined by immunohistology," in *Leucocyte Typing III: White Cell Differentiation Antigens*, A.J. McMichael, ed., International Workshop and Conference on Human Leucocyte Differentiation Antigens (3rd, 1986), Oxford University Press, Oxford, England, pp. 337-339.

Roux et al., "Comparisons of the Ability of Human IgG3 Hinge Mutants, IgM, IgE, and IgA2, to Form Small Immune Complexes: A Role for Flexibility and Geometry," *The Journal of Immunology* 161: 4083-4090, 1998.

Welschof et al., "The Antigen Binding Domain of Non-idiotypic Human Anti-F(ab')$_2$ Autoantibodies: Study of their Interaction with IgG Hinge Region Epitopes," *Human Immunology* 60: 282-290, 1999.

Afanasieva, T.A., et al., "Single-chain antibody and its derivatives directed against vascular endothelial growth factor: application for antiangiogenic gene therapy," Gene Therapy 10:1850-1859, 2003.

Angal, S., et al., "A single amino acid substitution abolishes the heterogeneity of chimeric mouse/human (IgG4) antibody," Mol. Immunol. 30(1):105-108, 1993.

Baum, P.R., et al., "Evaluation of the effect of TRU-016, an anti-CD37 directed SMIP™, in combination with other therapeutic drugs in models of Non-Hodgkin's Lymphoma," 2009 Annual Meeting, American Society of Clinical Oncology (ASCO), J. Clin. Oncol. 27(May 20 Suppl.):15S (Abstract 8571), 2009.

Benoist, C., and Mathis, D., "A revival of the B cell paradigm for rheumatoid arthritis pathogenesis?" Arthritis Res. 2(2):90-94, 2000.

Berzofsky, J.A., and Berkower, I.J., "Immunogenicity and Antigen Structure," in Fundamental Immunology, Third Edition, William E. Paul, Ed., Chap. 8, pp. 235-282, Raven Press, Ltd., New York, 1993.

Bloom, J.W., et al., "Intrachain disulfide bond in the core hinge region of human IgG4," Protein Sci. 6:407-415, 1997.

Boehm, M.K., et al., "The Fab and Fc fragments of IgA1 exhibit a different arrangement from that in IgG: a study by X-ray and neutron solution scattering and homology modelling," J. Mol. Biol. 286:1421-1447, 1999.

Brinkmann, U., et al., "Recombinant immunotoxins containing the VH or VL domain of monoclonal antibody B3 fused to Pseudomonas exotoxin," J. Immunol 150(7):2774-2782, 1993.

Brok, H.P.M., et al., "Prophylactic and therapeutic effects of a humanized monoclonal antibody against the IL-2 receptor (DACLIZUMAB) on collagen-induced arthritis (CIA) in rhesus monkeys," Clin. Exp. Immunol. 124:134-141, 2001.

Brorson, K., et al., "Mutational analysis of avidity and fine specificity of anti-levan antibodies," J. Immunol. 163:6694-6701, 1999.

Brown, R.S., et al., "Intratumoral microdistribution of [$^{131}$I]MB-1 in patients with B-cell lymphoma following radioimmunotherapy," Nucl. Med. Biol. 24:657-663, 1997.

Brummell, D.A., et al., "Probing the Combining Site of an Anti-Carbohydrate Antibody by Saturation-Mutagenesis: Role of the Heavy-Chain CDR3 Residues," Biochemistry 32:1180-1187, 1993.

Burgess, W.H., et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111:2129-2138, 1990.

Burks, E.A., et al., "In vitro scanning saturation mutagenesis of an antibody binding pocket," Proc. Natl. Acad. Sci. USA 94:412-417, 1997.

Bussel, J.B., "Overview of Idiopathic Thrombocytopenic Purpura: New Approach to Refractory Patients," Semin Oncol. 27(6 Suppl 12):91-98, 2000.

Byrd, J.C., et al., "Effect of CD37 small modular immuno-pharmaceutical (SMIP™) on direct apoptosis in chronic lymphocytic leukemia cells via transcriptional up-regulation of the BH3 family member BIM," 2009 Annual Meeting, American Society of Clinical Oncology (ASCO), J. Clin. Oncol. 27(May 20 Suppl.):155 (Abstract 3035), 2009.

Cai, X., and Garen, A., "Comparison of fusion phage libraries displaying VH or single-chain Fv antibody fragments derived from the antibody repertoire of a vaccinated melanoma patient as a source of melanoma-specific targeting molecules," Proc. Natl. Acad. Sci. USA 94:9261-9266, 1997.

Campbell, N.A., et al., Biology, 5th Ed., p. 856, Benjamin-Cummings Publ. Co., Menlo Park, CA (1999).

Carter, P., "Antibody Engineering—IBC's Tenth International Conference, Dec. 6-9, 1999, La Jolla, CA, USA," IDrugs 3(3):259-261, 2000. PubMed Abstract Only, PMID: 16103927.

Casset, F., et al., "A peptide mimetic of an anti-CD4 monoclonal antibody by rational design," Biochem. Biophys. Res. Commun. 307:198-205, 2003.

Chatterjee, M.B., et al., "Idiotypic antibody immunotherapy of cancer," Cancer Immunol Immunother. 38:75-82, 1994.

Chen, Y., et al., "Selection and Analysis of an Optimized Anti-VEGF Antibody: Crystal Structure of an Affinity-matured Fab in Complex with Antigen," J. Mol. Biol. 293:865-881, 1999.

Clackson, T., et al., "Making antibody fragments using phage display libraries," Nature 352:624-628, 1991.

Clark, E.A., and Einfeld, D, "Human B Cell Surface Molecules Defined by an International Workshop Panel of Monoclonal Antibodies," in Leukocyte Typing II (1986), vol. 2, Reinherz, E.L., et al., Eds., pp. 155-167, Springer-Verlag, New York, 1986.

Coiffier, B., et al., "Rituximab (Anti-CD20 Monoclonal Antibody) for the Treatment of Patients With Relapsing or Refractory Aggressive Lymphoma: A Multicenter Phase II Study," Blood 92(6):1927-1932, 1998.

Colman, P.M., "Effects of amino acid sequence changes on antibody-antigen interactions," Res. Immunol 145:33-36, 1994.

Cooke, S.P., et al., "A strategy for antitumor vascular therapy by targeting the vascular endothelial growth factor: receptor complex," Cancer Res. 61:3653-3659, 2001.

Davies J., and Riechmann, L., "Single antibody domains as small recognition units: design and in vitro antigen selection of camelized, human VH domains with improved protein stability," Protein Eng. 9(6):531-537, 1996.

De Pascalis, R., et al., "Grafting of 'abbreviated' complementarity-determining regions containing specificity-determining residues essential for ligand contact to engineer a less immunogenic humanized monoclonal antibody," J. Immunol. 169(6):3076-3084, 2002.

Deans, J.P., et al., "Association of tyrosine and serine kinases with the B cell surface antigen CD20. Induction via CD20 of tyrosine phosphorylation and activation of phospholipase C-γ1 and PLC phospholipase C-γ2," J. Immunol 151(9):4494-4504, 1993.

Dechant, M., et al., "Chimeric IgA antibodies against HLA class II effectively trigger lymphoma cell killing," Blood 100(13):4574-4580, 2002.

Dermer, G.B., "Another Anniversary for the War on Cancer," Bio/Technology 12:320, 1994.

Dorrington, K.J., and Klein, M., "Aspects of immunoglobulin G structure relevant to its interaction with Fc receptors," Arch. Immunol. Ther. Exp. (Warsz.) 29:275-282, 1981.

Dufner, P., et al., "Harnessing phage and ribosome display for antibody optimisation," Trends Biotechnol. 24(11):523-529, 2006.

Dyer, M.J., et al., "Effects of CAMPATH-1 antibodies in vivo in patients with lymphoid malignancies: influence of antibody isotype," Blood 73(6):1431-1439, 1989.

Edwards, J.C.W., and Cambridge, G., "Rheumatoid Arthritis: The Predictable Effect of Small Immune Complexes in which Antibody Is Also Antigen," Br. J. Rheumatol. 37:126-130, 1998.

Edwards, J.C.W., et al., "Do self-perpetuating B lymphocytes drive human autoimmune disease?" Immunology 97:188-196, 1999.

Edwards, J.C.W., et al., "B-lymphocyte depletion therapy in rheumatoid arthritis and other autoimmune disorders," Biochem. Soc. Trans. 30(4):824-828, 2002.

Edwards, J.C.W., et al., "Efficacy of B-Cell-Targeted Therapy with Rituximab in Patients with Rheumatoid Arthritis," New Engl. J. Med. 350:2572-2581, 2004.

Fell, H.P., et al., "Chimeric L6 Anti-tumor Antibody. Genomic construction, expression, and characterization of the antigen binding site," J. Biol. Chem. 267(22):15552-15558, 1992.

Genbank Accession No. M83312, Mouse CD40 mRNA, complete cds, Apr. 27, 1993.

Genbank Accession No. M84371, Human CD19 gene, complete cds, Apr. 27, 1993.

Genbank Accession No. M84371, Human CD19 gene, complete cds, Jul. 18, 1995.

Genbank Accession No. U15637, Homo sapiens CD40 binding protein (CD4OBP) mRNA, complete cds, Dec. 7, 1994.

Genbank Accession No. X14046, Human mRNA for leukocyte antigen CD37, Apr. 21, 1993.

Genbank Accession No. X53517, R. norvegicus mRNA for antigen CD37, Apr. 21, 1993.
Genbank Accession No. X65453, M. musculus mRNA for CD40 ligand, Apr. 21, 1993.
Genbank Accession No. X65453, M. musculus mRNA for CD40 ligand, Apr. 27, 2001.
Genbank Accession No. X67878, H. sapiens mRNA for CD40 ligand, Apr. 21, 1993.
Genbank Accession No. X96710, H. sapiens mRNA for CD40 ligand, Apr. 5, 1996.
Genbank Accession No. Y10507, H. sapiens mRNA for CD40 protein, Sep. 9, 1997.
Gillies, S.D., et al., "Improving the efficacy of antibody-interleukin 2 fusion proteins by reducing their interaction with Fc receptors," Cancer Res. 59:2159-2166, 1999.
Gura, T., "Cancer Models. Systems for Identifying New Drugs Are Often Faulty," Science 278(5340):1041-1042, 1997.
Halin, C., et al., "Tumor-targeting properties of antibody-vascular endothelial growth factor fusion proteins," Int. J. Cancer 102:109-116, 2002.
Hellström, I., et al., "Monoclonal Mouse Antibodies Raised against Human Lung Carcinoma," Canc. Res. 46:3917-3923, 1986.
Holliger, P., and Hudson, P.J., "Engineered antibody fragments and the rise of single domains," Nat. Biotechnol. 23(9):1126-1136, 2005.
Holm, P., et al., "Functional mapping and single chain construction of the anti-cytokeratin 8 monoclonal antibody TS1," Mol. Immunol. 44:1075-1084, 2007.
Huls, G., et al., "Antitumor Immune Effector Mechanisms Recruited by Phage Display-derived Fully Human IgG1 and IgA1 Monoclonal Antibodies," Cancer Res. 59:5778-5784, 1999.
Huston, J.S., et al., "Medical applications of single-chain antibodies," Int. Rev. Immunol. 10:195- 217, 1993.
International Preliminary Examination Report, dated Nov. 28, 2007, for PCTAN PCT/US03/24918, 5 pages.
International Preliminary Examination Report, dated Aug. 4, 2006, for PCTAN PCT/US03/41600, 5 pages.
International Search Report, mailed Sep. 18, 2002, for PCTAN PCT/US02/07011, 3 pages.
International Search Report, mailed Jan. 22, 2007, for PCTAN PCT/US03/24918, 4 pages.
International Search Report, mailed Nov. 2, 2004, for PCTAN PCT/US03/41600, 4 pages.
Isaacs, J.D., et al., "Therapy with monoclonal antibodies. II. The contribution of Fcγ receptor binding and the influence of $C_H1$ and $C_H3$ domains on in vivo effector function," J. Immunol 161:3862-3869, 1998.
"IUPAC-IUB commission on biochemical nomenclature rules for naming synthetic modifications of natural peptides tentative rules," J. Biol. Chem. 242:555-557, 1967.
Jain, R.K., "Physiological barriers to delivery of monoclonal antibodies and other macromolecules in tumors," Cancer Res. 50 (Suppl.):814s-819s, 1990.
Jain, R.K., "Barriers to drug delivery in solid tumors," Scientific American, pp. 58-65, 1994.
Jong, Y.-J., et al., "The structural basis for DNA binding by an anti-DNA autoantibody," Mol. Immunol 35:1207-1217, 1998.
Joosten, L.A.B., et al., "Protection against cartilage and bone destruction by systemic interleukin-4 treatment in established murine type II collagen-induced arthritis," Arthritis Res. 1:81-91, 1999.
Keystone, E., "B cell targeted therapies," Arthritis Res. Ther. 7(Suppl. 3):S13-S18, 2005.
Kobayashi, H., et al., "Tryptophan H33 plays an important role in pyrimidine (6-4) pyrimidone photoproduct binding by a high-affinity antibody," Protein Eng. 12(10):879-884, 1999.
Kortt, A.A., et al., "Recombinant anti-sialidase single-chain variable fragment antibody. Characterization, formation of dimer and higher-molecular-mass multimers and the solution of the crystal structure of the single-chain variable fragment/sialidase complex," Eur. J. Biochem. 221:151-157, 1994.
Kumar, S., et al., "Molecular Cloning and Expression of the Fabs of Human Autoantibodies in *Escherichia coli*," J. Biol. Chem. 275(45):35129-35136, 2000.
Ladetto, M., et al., "Rituximab anti-CD20 monoclonal antibody induces marked but transient reductions of peripheral blood lymphocytes in chronic lymphocytic leukaemia patients," Med. Oncol. 17:203-210, 2000.
Law, C.-L., et al., "Expression and characterization of recombinant soluble human CD3 molecules: presentation of antigenic epitopes defined on the native TCR-CD3 complex," Int. Immunol 14(4):389-400, 2002.
Layios, N., et al., "Remission of severe cold agglutinin disease after Rituximab therapy," Leukemia, pp. 187-188, 2000.
Lazar, E., et al., "Transforming growth factor α: mutation of aspartic acid 47 and leucine 48 results in different biological activities," Mol. Cell. Biol. 8(3):1247-1252, 1988.
Ledbetter, J.A., et al., "Antibodies to Tp67 and Tp44 Augment and Sustain Proliferative Responses of Activated T Cells," J. Immunol 135(4):2331-2336, 1985.
Ledbetter, J.A., et al., "Binding Domain-Immunoglobulin Fusion Proteins," Office Action dated Oct. 12, 2006, for U.S. Appl. No. 10/053,530, 16 pages.
Ledbetter, J.A., et al., "Binding Domain-Immunoglobulin Fusion Proteins," Office Action dated Jul. 25, 2006, for U.S. Appl. No. 10/207,655, 29 pages.
Ledbetter, J.A., et al., "Binding Domain-Immunoglobulin Fusion Proteins," Office Action dated Apr. 2, 2007, for U.S. Appl. No. 10/207,655, 22 pages.
Ledbetter, J.A., et al., "Binding Domain-Immunoglobulin Fusion Proteins," Office Action dated Jan. 14, 2008, for U.S. Appl. No. 10/207,655, 27 pages.
Ledbetter, J.A., et al., "Binding Domain-Immunoglobulin Fusion Proteins," Office Action dated Nov. 4, 2008, for U.S. Appl. No. 10/207,655, 20 pages.
Ledbetter, J.A., et al., "Binding Domain-Immunoglobulin Fusion Proteins," Office Action dated May 18, 2009, for U.S. Appl. No. 10/207,655, 7 pages.
Ledbetter, J.A., et al., "Binding Domain-Immunoglobulin Fusion Proteins," Office Action dated Nov. 20, 2009, for U.S. Appl. No. 10/207,655, 10 pages.
Ledbetter, J.A., et al., "Binding Constructs and Methods for Use Thereof," Office Action dated Jul. 10, 2008, for U.S. Appl. No. 10/566,409, 8 pages.
Ledbetter, J.A., et al., "Binding Constructs and Methods for Use Thereof," Office Action dated Feb. 20, 2009, for U.S. Appl. No. 10/566,409, 13 pages.
Ledbetter, J.A., et al., "Binding Constructs and Methods for Use Thereof," Office Action dated Jun. 9, 2009, for U.S. Appl. No. 10/566,409, 32 pages.
Ledbetter, J.A., et al., "Binding Constructs and Methods for Use Thereof," Office Action dated Nov. 27, 2009, for U.S. Appl. No. 10/566,409, 12 pages.
Ledbetter, J.A., et al., "Binding Constructs and Methods for Use Thereof," Office Action dated Dec. 8, 2006, for U.S. Appl. No. 10/627,556, 38 pages.
Ledbetter, J.A., et al., "Binding Constructs and Methods for Use Thereof," Office Action dated Sep. 11, 2007, for U.S. Appl. No. 10/627,556, 19 pages.
Ledbetter, J.A., et al., "Binding Constructs and Methods for Use Thereof," Office Action dated Feb. 14, 2008, for U.S. Appl. No. 10/627,556, 22 pages.
Ledbetter, J.A., et al., "Binding Constructs and Methods for Use Thereof," Office Action dated Nov. 26, 2008, for U.S. Appl. No. 10/627,556, 25 pages.
Ledbetter, J.A., et al., "Binding Constructs and Methods for Use Thereof," Office Action dated Jun. 24, 2009, for U.S. Appl. No. 10/627,556, 14 pages.
Ledbetter, J.A., et al., "Binding Constructs and Methods for Use Thereof," Office Action dated Nov. 6, 2009, for U.S. Appl. No. 10/627,556, 15 pages.
Ledbetter, J.A., et al., "Binding Domain-Immunoglobulin Fusion Proteins," Office Action dated Sep. 14, 2006, for U.S. Appl. No. 11/088,569, 8 pages.
Ledbetter, J.A., et al., "Binding Domain-Immunoglobulin Fusion Proteins," Office Action dated Jun. 4, 2007, for U.S. Appl. No. 11/088,569, 24 pages.

Ledbetter, J.A., et al., "Binding Domain-Immunoglobulin Fusion Proteins," Office Action dated Feb. 28, 2008, for U.S. Appl. No. 11/088,569, 26 pages.

Ledbetter, J.A., et al., "Binding Domain-Immunoglobulin Fusion Proteins," Office Action dated Sep. 14, 2006, for U.S. Appl. No. 11/088,570, 7 pages.

Ledbetter, J.A., et al., "Binding Domain-Immunoglobulin Fusion Proteins," Office Action dated Jun. 6, 2007, for U.S. Appl. No. 11/088,570, 27 pages.

Ledbetter, J.A., et al., "Binding Domain-Immunoglobulin Fusion Proteins," Office Action dated Mar. 3, 2008, for U.S. Appl. No. 11/088,570, 28 pages.

Ledbetter, J.A., et al., "Binding Domain-Immunoglobulin Fusion Proteins," Office Action dated May 14, 2007, for U.S. Appl. No. 11/088,693, 11 pages.

Ledbetter, J.A., et al., "Binding Domain-Immunoglobulin Fusion Proteins," Office Action dated Mar. 28, 2008, for U.S. Appl. No. 11/088,693, 16 pages.

Ledbetter, J.A., et al., "Binding Domain-Immunoglobulin Fusion Proteins," Office Action dated Mar. 4, 2009, for U.S. Appl. No. 11/088,693, 10 pages.

Ledbetter, J.A., et al., "Binding Domain-Immunoglobulin Fusion Proteins," Office Action dated Sep. 11, 2009, for U.S. Appl. No. 11/088,693, 12 pages.

Ledbetter, J.A., et al., "Binding Domain-Immunoglobulin Fusion Proteins," Office Action dated Jan. 14, 2010, for U.S. Appl. No. 11/088,693, 13 pages.

Ledbetter, J.A., et al., "Binding Domain-Immunoglobulin Fusion Proteins," Office Action dated Jan. 18, 2011, for U.S. Appl. No. 11/088,693, 8 pages.

Ledbetter, J.A., et al., "Binding Domain-Immunoglobulin Fusion Proteins," Office Action dated Sep. 14, 2006, for U.S. Appl. No. 11/088,737, 7 pages.

Ledbetter, J.A., et al., "Binding Domain-Immunoglobulin Fusion Proteins," Office Action dated Jun. 4, 2007, for U.S. Appl. No. 11/088,737, 27 pages.

Ledbetter, J.A., et al., "Binding Domain-Immunoglobulin Fusion Proteins," Office Action dated Mar. 3, 2008, for U.S. Appl. No. 11/088,737, 29 pages.

Ledbetter, J.A., et al., "Binding Domain-Immunoglobulin Fusion Proteins," Office Action dated Sep. 14, 2006, for U.S. Appl. No. 11/089,190, 7 pages.

Ledbetter, J.A., et al., "Binding Domain-Immunoglobulin Fusion Proteins," Office Action dated Jun. 4, 2007, for U.S. Appl. No. 11/089,190, 27 pages.

Ledbetter, J.A., et al., "Binding Domain-Immunoglobulin Fusion Proteins," Office Action dated Mar. 3, 2008, for U.S. Appl. No. 11/089,190, 26 pages.

Ledbetter, J.A., et al., "Binding Domain-Immunoglobulin Fusion Proteins," Office Action dated Apr. 5, 2007, for U.S. Appl. No. 11/089,367, 11 pages.

Ledbetter, J.A., et al., "Binding Domain-Immunoglobulin Fusion Proteins," Office Action dated Nov. 30, 2007, for U.S. Appl. No. 11/089,367, 15 pages.

Ledbetter, J.A., et al., "Binding Domain-Immunoglobulin Fusion Proteins," Office Action dated Sep. 12, 2006, for U.S. Appl. No. 11/089,368, 8 pages.

Ledbetter, J.A., et al., "Binding Domain-Immunoglobulin Fusion Proteins," Office Action dated Jun. 8, 2007, for U.S. Appl. No. 11/089,368, 29 pages.

Ledbetter, J.A., et al., "Binding Domain-Immunoglobulin Fusion Proteins," Office Action dated Mar. 5, 2008, for U.S. Appl. No. 11/089,368, 30 pages.

Ledbetter, J.A., et al., "Binding Domain-Immunoglobulin Fusion Proteins," Office Action dated Jul. 13, 2006, for U.S. Appl. No. 11/089,511, 7 pages.

Ledbetter, J.A., et al., "Binding Domain-Immunoglobulin Fusion Proteins," Office Action dated Mar. 26, 2007, for U.S. Appl. No. 11/089,511, 34 pages.

Ledbetter, J.A., et al., "Binding Domain-Immunoglobulin Fusion Proteins," Office Action dated Jan. 14, 2008, for U.S. Appl. No. 11/089,511, 30 pages.

Ledbetter, J.A., et al., "Binding Constructs and Methods for Use Thereof," Office Action dated Nov. 29, 2010, for U.S. Appl. No. 12/371,467, 17 pages.

Ledbetter, J.A., et al., "Binding Domain-Immunoglobulin Fusion Proteins," Office Action dated Mar. 22, 2010, for U.S. Appl. No. 12/541,062, 9 pages.

Ledbetter, J.A., et al., "Binding Domain-Immunoglobulin Fusion Proteins," Office Action dated Jul. 12, 2010, for U.S. Appl. No. 12/541,062, 9 pages.

Ledbetter, J.A., et al., "Binding Domain-Immunoglobulin Fusion Proteins," Office Action dated Dec. 13, 2010, for U.S. Appl. No. 12/541,062, 12 pages.

Ledbetter, J.A., et al., "Binding Domain-Immunoglobulin Fusion Proteins," Office Action dated Jun. 2, 2010, for U.S. Appl. No. 12/724,333, 7 pages.

Ledbetter, J.A., et al., "Binding Domain-Immunoglobulin Fusion Proteins," Office Action dated Sep. 2, 2010, for U.S. Appl. No. 12/724,333, 11 pages.

Lee, E.J., and Kueck, B., "Rituxan in the Treatment of Cold Agglutinin Disease," Blood 92(9):3490-3491, 1998.

Lehninger, A.L., et al., Principles of Biochemistry, 2nd Ed., Figure 5-6, Worth Publishers, New York (1993).

Leigh, B.R., et al., "Preclinical evaluation of chimeric L6 antibody for the treatment of Kaposi's sarcoma with radioimmunotherapy," Cancer Biother. Radiopharm. 14(2):113-119, 1999.

Levine, T.D., and Pestronk, A., "IgM antibody-related polyneuropathies: B-cell depletion chemotherapy using Rituximab," Neurology 52:1701-1704, 1999.

Lin, M.C, et al., "Structure-Function Relationships in Glucagon: Properties of Highly Purified Des-His$^1$-, Monoiodo-, and [Des-Asn$^{28}$, Thr$^{29}$](homoserine lactone$^{27}$)-glucagon," Biochemistry 14(8):1559-1563, 1975.

MacCallum, R.M., et al., "Antibody-antigen Interactions: Contact Analysis and Binding Site Topography," J. Mol. Biol. 262:732-745, 1996.

Maloney, D.G., et al., "Phase I Clinical Trial Using Escalating Single-Dose Infusion of Chimeric Anti-CD20 Monoclonal Antibody (IDEC-C2B8) in Patients With Recurrent B-Cell Lymphoma," Blood 84(8):2457-2466, 1994.

Martens, C.L., et al., "Heavy chain genes of rabbit IgG: Isolation of a cDNA encoding γ heavy chain and identification of two genomic Cγ genes," Proc. Natl. Acad. Sci. USA 79:6018-6022, 1982.

Mattu, T.S., et al., "The Glycosylation and Structure of Human Serum IgA1, Fab, and Fc Regions and the Role of N-Glycosylation on Fcα Receptor Interactions," J. Biol. Chem. 273(4):2260-2272, 1998.

Nadler, L.M., "B Cell/Leukemia Panel Workshop. Summary and Comments," in Leukocyte Typing II, vol. 2, Reinherz, E.L., et al., Eds., pp. 3-21, Springer Verlag, New York, 1986.

Nguyen, V.K., et al., "Heavy-chain antibodies in *Camelidae*; a case of evolutionary innovation," Immunogenetics 54:39-47, 2002.

Nieba, L., et al., "Disrupting the hydrophobic patches at the antibody variable/constant domain interface: improved in vivo folding and physical characterization of an engineered scFv fragment," Protein Eng. 10(4):435-444, 1997.

Novak, H., et al., "Selective antibody-mediated targeting of class I MHC to EGFR-expressing tumor cells induces potent antitumor CTL activity in vitro and in vivo," Int. J. Cancer 120:329-336, 2006.

Nuttall, S.D., et al., "Immunoglobulin VH domains and beyond: design and selection of single-domain binding and targeting reagents," Curr. Pharm. Biotechnol. 1:253-263, 2000.

Okazaki, T., et al., "PD-1 immunoreceptor inhibits B cell receptor-mediated signaling by recruiting src homology 2-domain-containing tyrosine phosphatase 2 to phosphotyrosine," Proc. Natl. Acad. Sci. USA 98(24):13866-13871, 2001.

Oki, S., et al., "Augmentation of CTLA-4 expression by wortmannin: involvement of lysosomal sorting properties of CTLA-4," Int. Immunol 11(9):1563-1571, 1999.

Padlan, E.A., "Anatomy of the Antibody Molecule," Mol. Immunol 31(3):169-217, 1994.

Protheroe, A., et al., "Remission of inflammatory arthropathy in association with anti-CD20 therapy for non-Hodgkin's lymphoma," Rheumatology 38:1150-1152, 1999.

PubMed (NCBI) search for "des-leucine," Publication Date to Jul. 26, 2003.

Ratanatharathorn, V., et al., "Anti-CD20 Chimeric Monoclonal Antibody Treatment of Refractory Immune-Mediated Thrombocytopenia in a Patient with Chronic Graft-versus-Host Disease," Ann Intern. Med. 133(4):275-279, 2000.

Riechmann, L., "Rearrangement of the former VL interface in the solution structure of a camelised, single antibody VH domain," J. Mol. Biol. 259:957-969, 1996.

Saleh, M.N., et al., A Pilot Study of the Anti-CD20 Monoclonal Antibody Rituximab in Patients With Refractory Immune Thrombocytopenia, Semin. Oncol. 27(6)(Suppl 12):99-103, 2000.

Santos, L., et al., "Role of macrophage migration inhibitory factor (MIF) in murine antigen-induced arthritis: interaction with glucocorticoids," Clin. Exp. Immunol. 123:309-314, 2001.

Schmidt, M., et al., "Suppression of metastasis formation by a recombinant single chain antibody-toxin targeted to full-length and oncogenic variant EGF receptors," Oncogene 18:1711-1721, 1999.

Schwartz, G.P., et al., "A superactive insulin: [B10-aspartic acid]insulin(human)," Proc. Natl. Acad. Sci. USA 84:6408-6411, 1987.

Search Output from ATCC Website for Hybridomas: 2H7 (pp. 1-2), 1D8 (p. 1), HD37 (p. 1), G28-1 (p. 1), 4.4.220 (p. 1), Fc2-2 (p. 1), UCHL-1 (p. 1), 5B9 (p. 1), L6 (p. 1), 10A8 (p. 1), 2e12 (p. 1). 40.2.36 (p. 1) and G19-4 (p. 1) (cited in Office Action dated Dec. 8, 2006 in U.S. Appl. No. 10/627,556, now U.S. Patent No. 7,829,084).

Seaver, S.S., "Monoclonal Antibodies in Industry: More Difficult Than Originally Thought," Genet. Eng. News 14(14):10, 21, 1994.

Shankar, S., et al., "Antiepidermal growth factor variant III scFv fragment: effect of radioiodination method on tumor targeting and normal tissue clearance," Nucl. Med. Biol. 33:101-110, 2006.

Shimoni, A., et al., "Autologous T Cells Control B-Chronic Lymphocytic Leukemia Tumor Progression in Human → Mouse Radiation Chimera," Cancer Res. 59:5968-5974, 1999.

Simonds, H.M., and Miles, D., "Adjuvant treatment of breast cancer: impact of monoclonal antibody therapy directed against the HER2 receptor," Expert Opin. Biol. Ther. 7(4):487-491, 2007.

Smith, K.A., et al., "Isolation and characterisation of vascular endothelial growth factor-165 specific scFv fragments by phage display," Int. J. Oncol. 22:333-338, 2003.

Smith-Gill, S.J., et al., "Contributions of immunoglobulin heavy and light chains to antibody specificity for lysozyme and two haptens," J. Immunol 139:4135-4144, 1987.

Song, M.-K., et al., "Light chain of natural antibody plays a dominant role in protein antigen binding," Biochem. Biophys. Res. Commun. 268:390-394, 2000.

Stevenson, G.T., et al., "Conjugation of Human Fcγin Closed-Hinge or Open-Hinge Configuration to Fab'γ and Analogous Ligands," J. Immunol. 158:2242-2250, 1997.

Tamura, H., et al., "B7-H1 costimulation preferentially enhances CD28-independent T-helper cell function," Blood 97(6):1809-1816, 2001.

Terry, L.A., et al., "The monoclonal antibody, UCHL1, recognizes a 180,000 MW component of the human leucocyte-common antigen, CD45," Immunol 64:331-336, 1988.

Treon, S.P., and Anderson, K.C., "The Use of Rituximab in the Treatment of Malignant and Nonmalignant Plasma Cell Disorders," Semin. Oncol. 27(Suppl 12):79-85, 2000.

Vajdos, F.F., et al., "Comprehensive Functional Maps of the Antigen-binding Site of an Anti-ErbB2 Antibody Obtained with Shotgun Scanning Mutagenesis," J. Mol. Biol. 320:415-428, 2002.

van den Beucken, T., et al., "Building novel binding ligands of B7.1 and B7.2 based on human antibody single variable light chain domains," J. Mol. Biol. 310:591-601, 2001.

Vitaliti, A., et al, "Inhibition of tumor angiogenesis by a single-chain antibody directed against vascular endothelial growth factor," Cancer Res. 60:4311-4314, 2000.

Ward, E.S., et al., "Binding activities of a repertoire of single immunoglobulin variable domains secreted from Escherichia coli," Nature 341:544-546, 1989.

Ward, E.S., and Ghetie, V., "The effector functions of immunoglobulins: implications for therapy," Ther. Immunol. 2:77-94, 1995.

Weston, K.M., et al., "In vivo binding of mouse IgG via polyreactive surface IgM abrogates progressive lymphocytosis in prolymphocytic leukemia," Leuk. Lymphoma 29:361-373, 1998.

Winberg, G., et al., "Surface Expression of CD28 Single Chain Fv for Costimulation by Tumor Cells," Immunol Rev. 153:209-223, 1996.

Wörn, A., and Plückthun, A., "Stability engineering of antibody single-chain Fv fragments," J. Mol. Biol. 305(5):989-1010, 2001.

Written Opinion, mailed Aug. 19, 2005, for PCTAN PCT/US03/41600, 4 pages.

Wu, H., et al., "Humanization of a murine monoclonal antibody by simultaneous optimization of framework and CDR residues," J. Mol. Biol. 294:151-162, 1999.

Ye, Z., et al., "Gene therapy for cancer using single-chain Fv fragments specific for 4-1BB," Nat. Med. 8(4):343-348, 2002.

Yoshinaga, S.K., et al., "Characterization of a new human B7-related protein: B7RP-1 is the ligand to the co-stimulatory protein ICOS," Int. Immunol 12(10):1439-1447, 2000.

Zaja, F., et al., "Rituximab for myasthenia gravis developing after bone marrow transplant," Neurology 55:1062-1063, 2000.

Zarling, J.M., et al., "Lysis of Cells Infected with HIV-1 by Human Lymphocytes Targeted with Monoclonal Antibody Heteroconjugates," J. Immunol. 140(8):2609-2613, 1988.

Zhao, X., et al., "Targeting CD37-positive lymphoid malignancies with a novel engineered small modular immunopharmaceutical," Blood 110(7):2569-2577, 2007.

Batra, J.K., et al., "Single-Chain Immunotoxins Directed at the Human Transferrin Receptor Containing Pseudomonas Exotoxin A or Diphtheria Toxin: Anti-TFR(Fv)-PE40 and DT388-Anti-TFR(Fv)," Mol. Cell. Biol. 11(4):2200-2205, 1991.

Brown, S.L., et al., "Treatment of B-Cell Lymphomas with Anti-idiotype Antibodies Alone and in Combination with Alpha Interferon," Blood 73(3):651-661, 1989.

Chaudhary, V.K., et al., "A recombinant immunotoxin consisting of two antibody variable domains fused to Pseudomonas exotoxin," Nature 339:394-397, 1989.

Clark, E.A., and Ledbetter, J.A., "Activation of human B cells mediated through two distinct cell surface differentiation antigens, Bp35 and Bp50," Proc. Natl. Acad. Sci. USA 83:4494-4498, 1986.

Davis, S.J., et al., "High Level Expression in Chinese Hamster Ovary Cells of Soluble Forms of CD4 T Lymphocyte Glycoprotein Including Glycosylation Variants," J. Biol. Chem. 265(18):10410-10418, 1990.

Dillman, R.O., et al., "Continuous infusion of T101 monoclonal antibody in chronic lymphocytic leukemia and cutaneous T-cell lymphoma," J. Biol. Response Mod. 5:394-410, 1986.

Einfeld, D.A., et al., "Molecular cloning of the human B cell CD20 receptor predicts a hydrophobic protein with multiple transmembrane domains," EMBO J. 7(3):711-717, 1988.

Filpula, et al., "Single-chain Fv designs for protein, cell and gene therapeutics," Exp. Opin. Ther. Patents 9(3):231-245, 1999.

Funakoshi, S., et al., "Differential in Vitro and in Vivo Antitumor Effects Mediated by Anti-CD40 and Anti-CD20 Monoclonal Antibodies Against Human B-Cell Lymphomas," J. Immunother. 19(2):93-101, 1996.

Hekman, A., et al., "Initial experience with treatment of human B cell lymphoma with anti-CD19 monoclonal antibody," Cancer Immunol Immunother. 32:364-372, 1991.

Huston, J.S., et al., "Protein engineering of antibody binding sites: Recovery of specific activity in an anti-digoxin single-chain Fv analogue produced in Escherichia coli," Proc. Natl. Acad. Sci. USA 85:5879-5883, 1988.

Jost, C.R., et al., "Mammalian Expression and Secretion of Functional Single-chain Fv Molecules," J. Biol. Chem. 269(42):26267-26273, 1994.

Kaminski, M.S., et al., "Radioimmunotherapy of B-Cell Lymphoma with [$^{131}$I]Anti-B1 (Anti-CD20) Antibody," N. Engl. J. Med. 329(7):459-465, 1993.

Kato, K., et al., "A conformational change in the Fc precludes the binding of two Fcγ receptor molecules to one IgG," Immunol. Today 21:310-312, 2000.

Koolwijk, P., et al., "Interaction between hybrid mouse monoclonal antibodies and the human high-affinity IgG FcR, huFcγ RI, on U937.

Involvement of only one of the mIgG heavy chains in receptor binding," J. Immunol. 143(5):1656-1662, 1989.

Maloney, D.G., et al., "IDEC-C2B8: results of a phase I multiple-dose trial in patients with relapsed non-Hodgkin's lymphoma," J. Clin. Oncol. 15(10):3266-3274, 1997.

Maloney, D.G., et al., "IDEC-C2B8 (Rituximab) Anti-CD20 Monoclonal Antibody Therapy in Patients with Relapsed Low-Grade Non-Hodgkin's Lymphoma," Blood 90(6):2188-2195, 1997.

McLaughlin, P., et al., "IDEC-C2B8 Anti-CD20 Antibody: Final Report on a Phase III Pivotal Trial in Patients (PTS) with Relapsed Low-Grade or Follicular Lymphoma (LG/F NHL)," Blood 88(10)(Suppl. 1):90a (Abstract 349), 1996.

Pawson, R., et al., "Treatment of T-cell prolymphocytic leukemia with human CD52 antibody," J. Clin. Oncol. 15(7):2667-2672, 1997.

Press, O.W., et al., "Monoclonal Antibody 1F5 (Anti-CD20) Serotherapy of Human B Cell Lymphomas," Blood 69(2):584-591, 1987.

Press, O.W., et al., "Radiolabeled-Antibody Therapy of B-Cell Lymphoma with Autologous Bone Marrow Support," N. Engl. J. Med. 329(17):1219-1224, 1993.

Radaev, S., et al., "The Structure of a Human Type III Fcγ Receptor in Complex with Fc," J. Biol. Chem. 276(19):16469-16477, 2001.

Radaev, S., and Sun, P.D., "Recognition of IgG by Fcγ receptor. The role of Fc glycosylation and the binding of peptide inhibitors," J. Biol. Chem. 276(19):16478-16483, 2001.

Redpath, S., et al., "The influence of the hinge region length in binding of human IgG to human Fcγ receptors," Hum. Immunol. 59:720-727, 1998.

Scheinberg, D.A., et al., "A phase I toxicity, pharmacology, and dosimetry trial of monoclonal antibody OKB7 in patients with non-Hodgkin's lymphoma: effects of tumor burden and antigen expression," J. Clin. Oncol. 8(5):792-803, 1990.

Sensel, M.G., et al., "Engineering novel antibody molecules," Chem. Immunol 65:129-158, 1997.

Shan, D., et al., "Apoptosis of Malignant Human B Cells by Ligation of CD20 with Monoclonal Antibodies," Blood 91(5):1644-1652, 1998.

Shin, S.-U., et al., "Genetically-Engineered Antibodies: Tools for the Study of Diverse Properties of the Antibody Molecule," Immunol Rev. 130:87-107, 1992.

Shin, S.-U., et al., "Hybrid antibodies," Int. Rev. Immunol 10:177-186, 1993.

Sondermann, P., et al., "The 3.2-Å crystal structure of the human IgG1 Fc fragment-FcγRIII complex," Nature 406:267-273, 2000.

Traunecker, A., et al., "Bispecific single chain molecules (Janusins) target cytotoxic lymphocytes on HIV infected cells," EMBO J. 10(12):3655-3659, 1991.

Vlasveld, L.T., et al., "Treatment of low-grade non-Hodgkin's lymphoma with continuous infusion of low-dose recombinant interleukin-2 in combination with the B-cell-specific monoclonal antibody CLB-CD19," Cancer Immunol Immunother. 40:37-47, 1995.

Yokota, T., et al., "Rapid Tumor Penetration of a Single-Chain Fv and Comparison with Other Immunoglobulin Forms," Canc. Res. 52:3402-3408, 1992.

Chothia, C., et al., "Domain association in immunoglobulin molecules. The packing of variable domains," J. Mol. Biol. 186(3):651-663, 1985.

Hamers-Casterman, C., et al., "Naturally occurring antibodies devoid of light chains," Nature 363:446-448, 1993.

Kaminski, M.S., et al., "Imaging, Dosimetry, and Radioimmunotherapy With Iodine 131-Labeled Anti-CD37 Antibody in B-Cell Lymphoma," J. Clin. Oncol. 10(11):1696-1711, 1992.

Muyldermans, S., et al., "Sequence and structure of VH domain from naturally occurring camel heavy chain immunoglobulins lacking light chains," Protein Eng. 7(9):1129-1135, 1994.

Muyldermans, S., "Single domain camel antibodies: current status," Rev. Mol. Biotechnol. 74:277-302, 2001.

Nadler, L.M., "B Cell/Leukemia Panel Workshop: Summary and Comments," in Leukocyte Typing II, vol. 2, Reinherz, E.L., et al., Eds., pp. 3-14, 20, 21, Springer Verlag, New York, 1986.

NCBI Reference Sequence NP_001765.1 for Leukocyte Surface Antigen CD37, Oct. 31, 2000.

Neve, R.M., et al., "Biological effects of anti-ErbB2 single chain antibodies selected for internalizing function," Biochem. Biophys. Res. Commun 280:274-279, 2001.

Nguyen, V.K., et al., "The specific variable domain of camel heavy-chain antibodies is encoded in the germline," J. Mol. Biol. 275:413-418, 1998.

Peter, K. et al., "Construction and functional evaluation of a single-chain antibody fusion protein with fibrin targeting and thrombin inhibition after activation by factor Xa," Circulation 101:1158-1164, 2000.

Pezzutto, A., et al., "CD19 Monoclonal Antibody HD37 Inhibits Anti-Immunoglobulin-Induced B Cell Activation and Proliferation," J. Immunol. 138(9):2793-2799, 1987.

Portolano, S., et al., "Lack of promiscuity in autoantigen-specific H and L chain combinations as revealed by human H and L chain 'roulette'," J. Immunol 150(3):880-887, 1993.

Press, O.W., et al., "Treatment of refractory non-Hodgkin's lymphoma with radiolabeled MB-1 (anti-CD37) antibody," J. Clin. Oncol. 7(8):1027-1038, 1989.

Ratanatharathorn, V., et al., "Anti-CD20 Chimeric Monoclonal Antibody Immune-Mediated Thrombocytopenia in a Patient with Chronic Graft-versus-Host Intern. Med. 133(4):275-279, 2000. Treatment of Refractory Disease," Ann. Intern. Med. 133(4):275-279, 2000.

Reff, M.E., et al., "Depletion of B Cells in Vivo by a Chimeric Mouse Human Monoclonal Antibody to CD20," Blood 83(2):435-445, 1994.

Spiro, R.G., "Protein glycosylation: nature, distribution, enzymatic formation, and disease implications of glycopeptide bonds," Glycobiology 12(4):43R-56R, 2002.

Stamenkovic, I., and Seed, B., "Analysis of Two cDNA Clones Encoding the B Lymphocyte Antigen CD20 (B1, Bp35), A Type III Integral Membrane Protein," J. Exp. Med. 167:1975-1980, 1988.

Tedder, T.F., et al., "Cloning of a Complementary DNA Encoding a New Mouse B Lymphocyte Differentiation Antigen, Homologous to the Human B1 (CD20) Antigen, and Localization of the Gene to Chromosome 19," J. Immunol. 141(12):4388-4394, 1988.

* cited by examiner

FIG. 1A

2H7scFv-Ig cDNA and predicted amino acid sequence:

```
        HindIII      NcoI        2H7 V_L Leader Peptide→
        ~~~~~~       ~~~~~~
                              M   D   F   Q   V   Q   I   F   S   F   L   L   I   S   A   S
    1   AAGCTTGCCG CC    ATGGATTT TCAAGTGCAG ATTTCAGCT TCCTGCTAAT CAGTGCTTCA 2H7 V_L →
         V   I   I   A   R   G   Q   I   V   L   S   Q   S   P   A   I   L   S   A   S
   61   GTCATAATTG CCAGAGGACA AATTGTTCTC TCCCAGTCTC CAGCAATCCT GTCTGCATCT P   G   E   K   V   T   M   T   C   R   A   S   S   S   V   S   Y   M   H   W
  121   CCAGGGGAGA AGGTCACAAT GACTTGCAGG GCCAGCTCAA GTGTAAGTTA CATGCACTGG BamHI
                     ~~~~~~
         Y   Q   Q   K   P   G   S   S   P   K   P   W   I   Y   A   P   S   N   L   A
  181   TACCAGCAGA AGCCAGGATC CTCCCCCAAA CCCTGGATTT ATGCCCCATC CAACCTGGCT S   G   V   P   A   R   F   S   G   S   G   S   G   T   S   Y   S   L   T   I
  241   TCTGGAGTCC CTGCTCGCTT CAGTGGCAGT GGGTCTGGGA CCTCTTACTC TCTCACAATC S   R   V   E   A   E   D   A   A   T   Y   Y   C   Q   Q   W   S   F   N   P
  301   AGCAGAGTGG AGGCTGAAGA TGCTGCCACT TATTACTGCC AGCAGTGGAG TTTTAACCCA (Gly_4Ser)_3 Linker
         P   T   F   G   A   G   T   K   L   E   L   K   G   G   G   S   G   G   G
  361   CCCACGTTCG GTGCTGGGAC CAAGCTGGAG CTGAAAGGTG GCGGTGGCTC GGGCGGTGGT 2H7 V_H →
         G   S   G   G   G   S   S   Q   A   Y   L   Q   Q   S   G   A   E   L   V
  421   GGATCTGGAG GAGGTGGGAG CTCTCAGGCT TATCTACAGC AGTCTGGGGC TGAGCTGGTG R   P   G   A   S   V   K   M   S   C   K   A   S   G   Y   T   F   T   S   Y
  481   AGGCCTGGGG CCTCAGTGAA GATGTCCTGC AAGGCTTCTG GCTACACATT TACCAGTTAC N   M   H   W   V   K   Q   T   P   R   Q   G   L   E   W   I   G   A   I   Y
  541   AATATGCACT GGGTAAAGCA GACACCTAGA CAGGGCCTGG AATGGATTGG AGCTATTTAT P   G   N   G   D   T   S   Y   N   Q   K   F   K   G   K   A   T   L   T   V
  601   CCAGGAAATG GTGATACTTC CTACAATCAG AAGTTCAAGG GCAAGGCCAC ACTGACTGTA D   K   S   S   S   T   A   Y   M   Q   L   S   S   L   T   S   E   D   S   A
  661   GACAAATCCT CCAGCACAGC CTACATGCAG CTCAGCAGCC TGACATCTGA AGACTCTGCG V   Y   F   C   A   R   V   V   Y   Y   S   N   S   Y   W   Y   F   D   V   W
  721   GTCTATTTCT GTGCAAGAGT GGTGTACTAT AGTAACTCTT ACTGGTACTT CGATGTCTGG
```

FIG. 1B

```
                                            BclI
                                         ~~~~~~~human IgG1 Fc domain →
        G   T   G   T       T   V   T       V   S   D       Q   E   P   K       S   C   D       K   T   H
 781    GGCACAGGGA  CCACGGTCAC  CGTCTCTGAT  CAGGAGCCCA  AATCTTGTGA  CAAAACTCAC T   C   P   P       C   P   A       P   E   L       L   G   G   P       S   V   F       L   F   P
 841    ACATGCCCAC  CGTGCCCAGC  ACCTGAACTC  CTGGGGGGAC  CGTCAGTCTT  CCTCTTCCCC P   K   P   K       D   T   L       M   I   S       R   T   P   E       V   T   C       V   V   V
 901    CCAAAACCCA  AGGACACCCT  CATGATCTCC  CGGACCCCTG  AGGTCACATG  CGTGGTGGTG D   V   S   H       E   D   P       E   V   K       F   N   W   Y       V   D   G       V   E   V
 961    GACGTGAGCC  ACGAAGACCC  TGAGGTCAAG  TTCAACTGGT  ACGTGGACGG  CGTGGAGGTG H   N   A   K       T   K   P       R   E   E       Q   Y   N   S       T   Y   R       V   V   S
1021    CATAATGCCA  AGACAAAGCC  GCGGGAGGAG  CAGTACAACA  GCACGTACCG  TGTGGTCAGC V   L   T   V       L   H   Q       D   W   L       N   G   K   E       Y   K   C       K   V   S
1081    GTCCTCACCG  TCCTGCACCA  GGACTGGCTG  AATGGCAAGG  AGTACAAGTG  CAAGGTCTCC N   K   A   L       P   A   P       I   E   K       T   I   S   K       A   K   G       Q   P   R
1141    AACAAAGCCC  TCCCAGCCCC  CATCGAGAAA  ACAATCTCCA  AAGCCAAAGG  GCAGCCCCGA E   P   Q   V       Y   T   L       P   P   S       R   D   E   L       T   K   N       Q   V   S
1201    GAACCACAGG  TGTACACCCT  GCCCCCATCC  CGGGATGAGC  TGACCAAGAA  CCAGGTCAGC L   T   C   L       V   K   G       F   Y   P       S   D   I   A       V   E   W       E   S   N
1261    CTGACCTGCC  TGGTCAAAGG  CTTCTATCCC  AGCGACATCG  CCGTGGAGTG  GGAGAGCAAT G   Q   P   E       N   N   Y       K   T   T       P   P   V   L       D   S   D       G   S   F
1321    GGGCAGCCGG  AGAACAACTA  CAAGACCACG  CCTCCCGTGC  TGGACTCCGA  CGGCTCCTTC F   L   Y   S       K   L   T       V   D   K       S   R   W   Q       Q   G   N       V   F   S
1381    TTCCTCTACA  GCAAGCTCAC  CGTGGACAAG  AGCAGGTGGC  AGCAGGGGAA  CGTCTTCTCA C   S   V   M       H   E   A       L   H   N       H   Y   T   Q       K   S   L       S   L   S
1441    TGCTCCGTGA  TGCATGAGGC  TCTGCACAAC  CACTACACGC  AGAAGAGCCT  CTCCCTGTCT XbaI
                                             ~~~~~
        P   G   K   *       S   R
1501    CCGGGTAAAT  GATCTAGA
```

FIG. 4A

Complement Mediated B Cell Killing After Binding of CD20-targeted 2H7 Derivatives:

| 2H7scFv-Ig Concentration | RAMOS | BJAB |
|---|---|---|
| 20 µg/ml + complement | 0.16 | 0.07 |
| 5 µg/ml + complement | 0.2 | N.D. |
| 1.25 µg/ml + complement | 0.32 | 0.1 |
| Complement alone | 0.98 | 0.94 |

*Viability was determined by trypan blue exclusion and is tabulated as the fraction of viable cells out of the total number of cells counted.

**N.D. (not determined).

FIG. 4B

Antibody-dependent cellular cytotoxicity (ADCC) mediated by 2H7scFv-Ig:

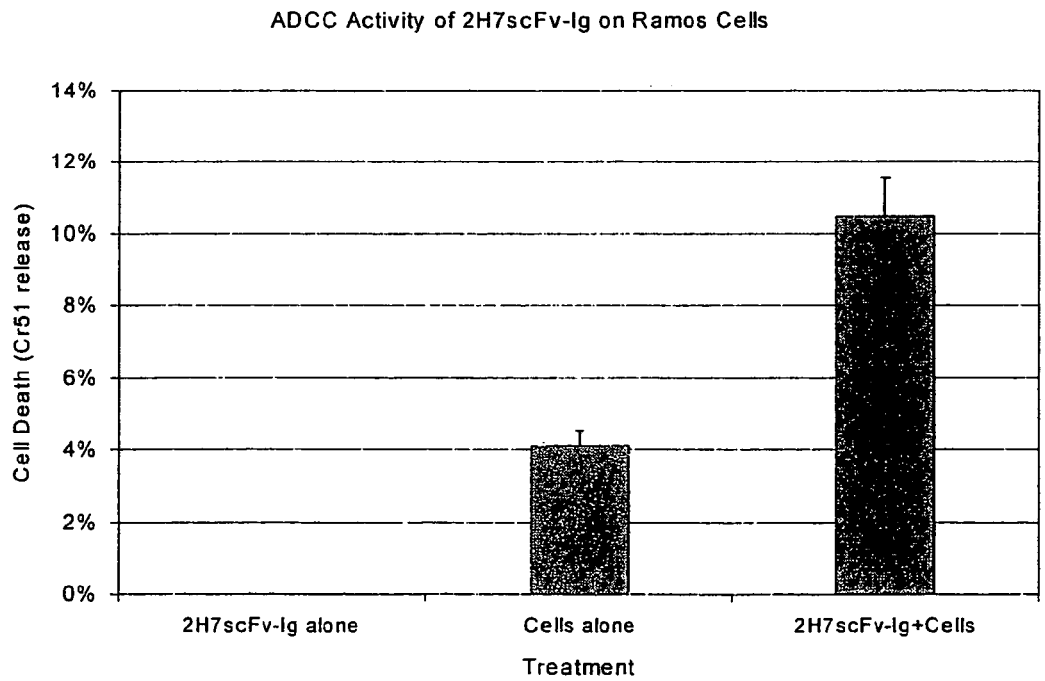

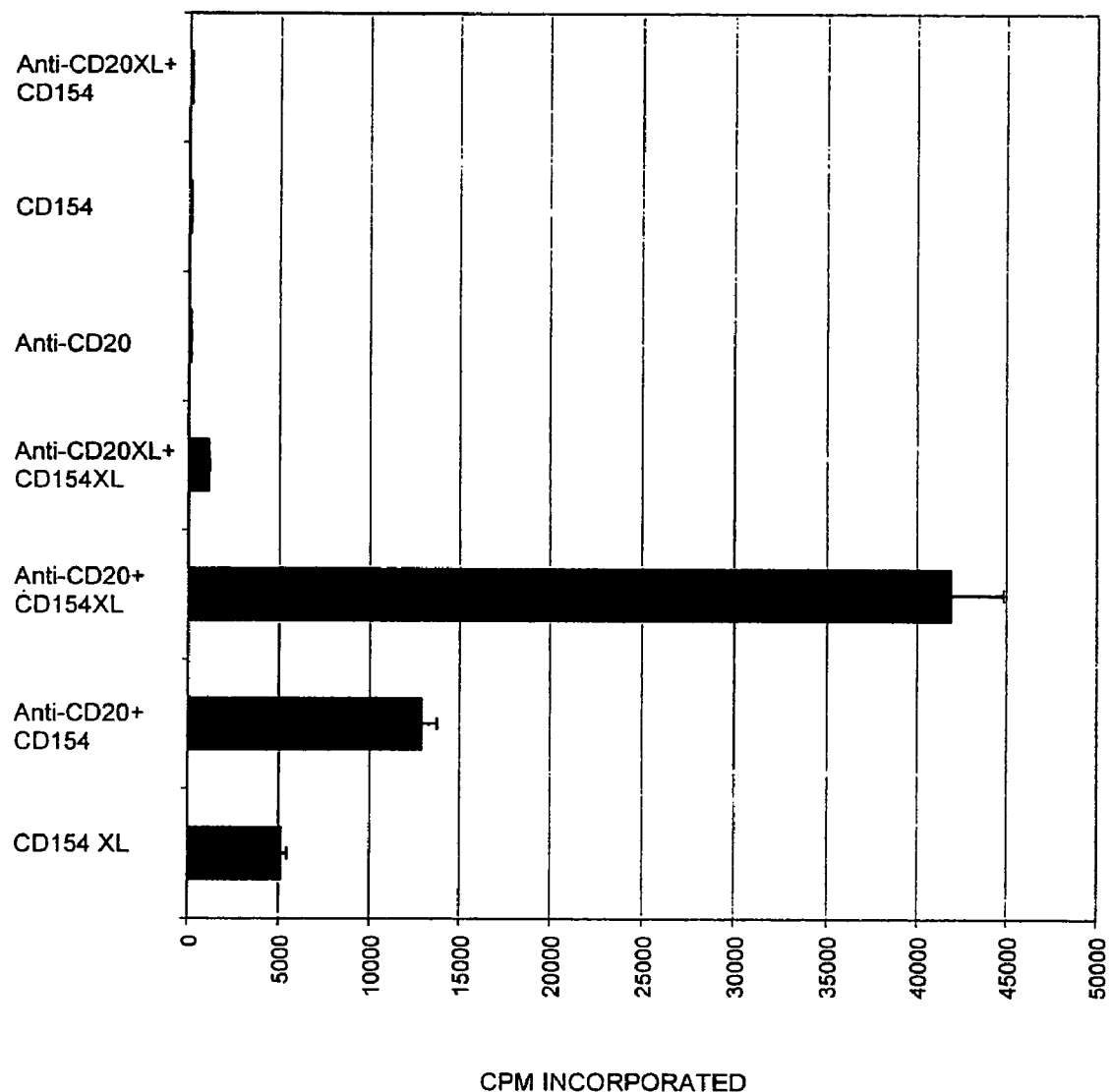

FIG. 6A
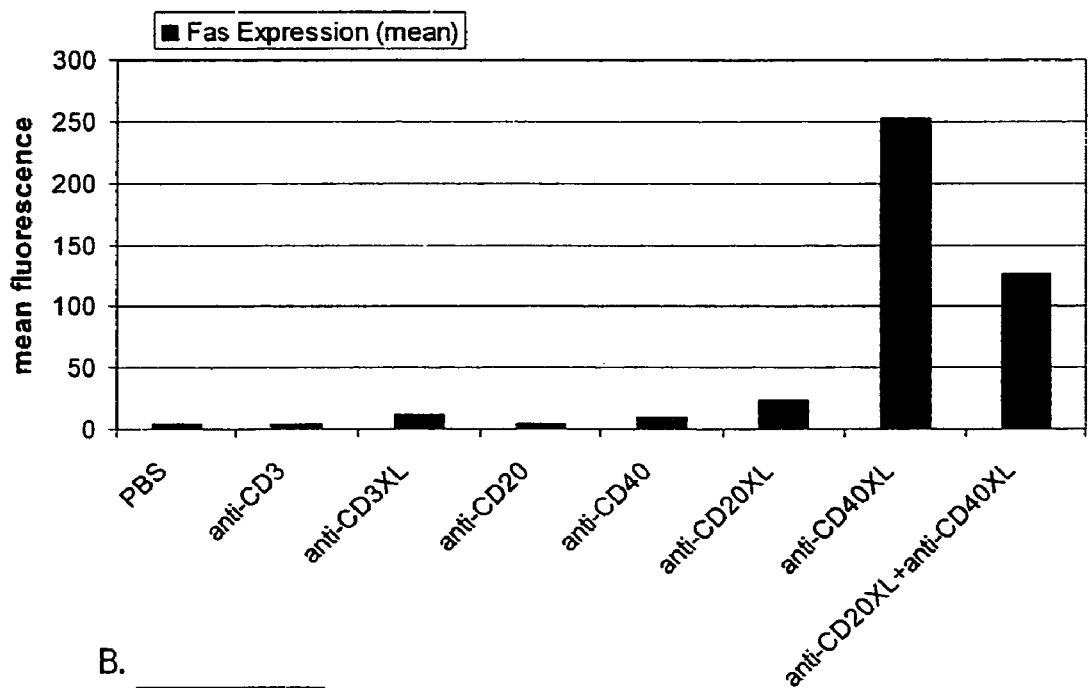
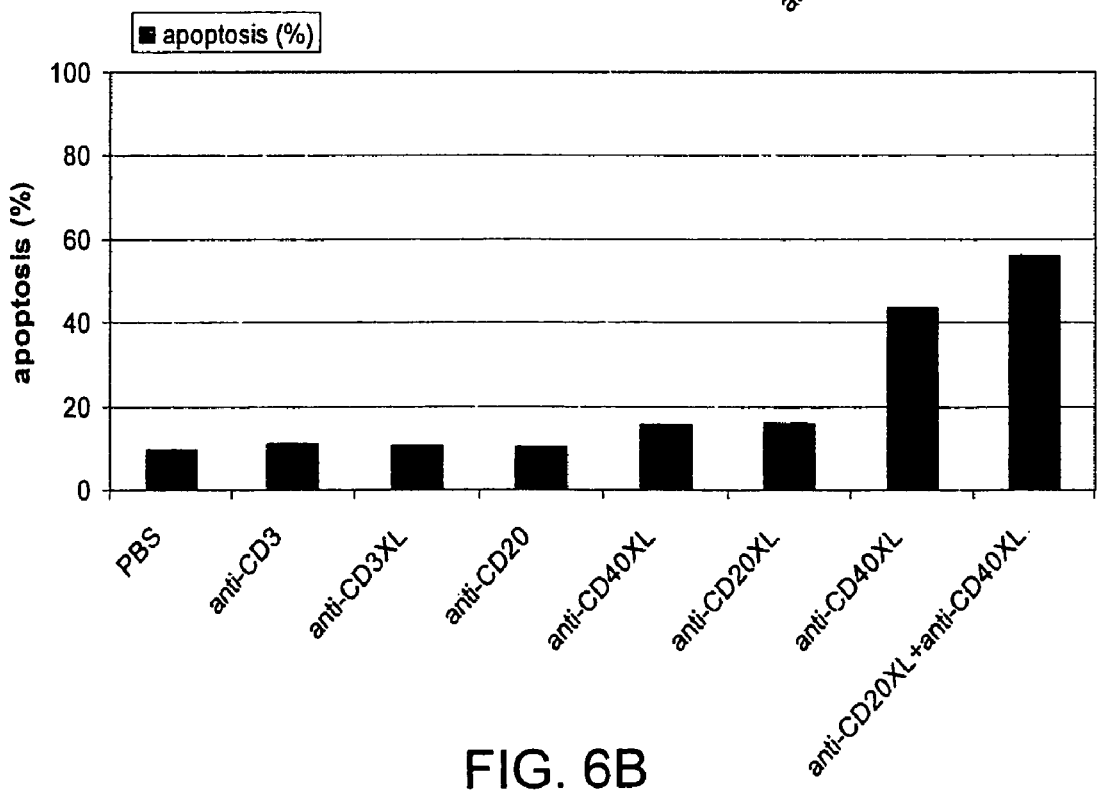
FIG. 6B

FIG. 7A

2H7-CD154 L2 cDNA and predicted amino acid sequence:

```
        HindIII     NcoI    2H7 V_L Leader Peptide →
        ~~~~~~      ~~~~~
                           M   D   F   Q   V   Q   I   F   S   F   L   L   I   S   A   S
      1 AAGCTTGCCG  CC      ATGGATTT TCAAGTGCAG ATTTTCAGCT TCCTGCTAAT CAGTGCTTCA 2H7 V_L →
        V   I   I   A   R   G   Q   I   V   L   S   Q   S   P   A   I   L   S   A   S
     61 GTCATAATTG CCAGAGGACA AATTGTTCTC TCCCAGTCTC CAGCAATCCT GTCTGCATCT P   G   E   K   V   T   M   T   C   R   A   S   S   S   V   S   Y   M   H   W
    121 CCAGGGGAGA AGGTCACAAT GACTTGCAGG GCCAGCTCAA GTGTAAGTTA CATGCACTGG BamHI
                        ~~~~~~~
        Y   Q   Q   K   P   G   S   S   P   K   P   W   I   Y   A   P   S   N   L   A
    181 TACCAGCAGA AGCCAGGATC CTCCCCCAAA CCCTGGATTT ATGCCCCATC CAACCTGGCT S   G   V   P   A   R   F   S   G   S   G   S   G   T   S   Y   S   L   T   I
    241 TCTGGAGTCC CTGCTCGCTT CAGTGGCAGT GGGTCTGGGA CCTCTTACTC TCTCACAATC S   R   V   E   A   E   D   A   A   T   Y   Y   C   Q   Q   W   S   F   N   P
    301 AGCAGAGTGG AGGCTGAAGA TGCTGCCACT TATTACTGCC AGCAGTGGAG TTTTAACCCA (Gly_4Ser)_3 Linker →
        P   T   F   G   A   G   T   K   L   E   L   K   G   G   G   S   G   G   G
    361 CCCACGTTCG GTGCTGGGAC CAAGCTGGAG CTGAAAGGTG GCGGTGGCTC GGGCGGTGGT 2H7 V_H →
        G   S   G   G   G   G   S   S   Q   A   Y   L   Q   Q   S   G   A   E   L   V
    421 GGATCTGGAG GAGGTGGGAG CTCTCAGGCT TATCTACAGC AGTCTGGGGC TGAGCTGGTG R   P   G   A   S   V   K   M   S   C   K   A   S   G   Y   T   F   T   S   Y
    481 AGGCCTGGGG CCTCAGTGAA GATGTCCTGC AAGGCTTCTG GCTACACATT TACCAGTTAC N   M   H   W   V   K   Q   T   P   R   Q   G   L   E   W   I   G   A   I   Y
    541 AATATGCACT GGGTAAAGCA GACACCTAGA CAGGGCCTGG AATGGATTGG AGCTATTTAT P   G   N   G   D   T   S   Y   N   Q   K   F   K   G   K   A   T   L   T   V
    601 CCAGGAAATG GTGATACTTC CTACAATCAG AAGTTCAAGG GCAAGGCCAC ACTGACTGTA D   K   S   S   S   T   A   Y   M   Q   L   S   S   L   T   S   E   D   S   A
    661 GACAAATCCT CCAGCACAGC CTACATGCAG CTCAGCAGCC TGACATCTGA AGACTCTGCG V   Y   F   C   A   R   V   V   Y   Y   S   N   S   Y   W   Y   F   D   V   W
    721 GTCTATTTCT GTGCAAGAGT GGTGTACTAT AGTAACTCTT ACTGGTACTT CGATGTCTGG
```

FIG. 7B human CD154/amino acid 48→

```
                                 Bcl/Bam hybrid site
         G   T   G   T      T   V   T     V   S   D     P   R   R   L     D   K   I     E   D   E
781      GGCACAGGGA     CCACGGTCAC     CGTCTCTGAT     CCAAGAAGGT     TGGACAAGAT     AGAAGATGAA R   N   L   H     E   D   F     V   F   M     K   T   I   Q     R   C   N     T   G   E
841      AGGAATCTTC     ATGAAGATTT     TGTATTCATG     AAAACGATAC     AGAGATGCAA     CACAGGAGAA R   S   L   S     L   L   N     C   E   E     I   K   S   Q     F   E   G     F   V   K
901      AGATCCTTAT     CCTTACTGAA     CTGTGAGGAG     ATTAAAAGCC     AGTTTGAAGG     CTTTGTGAAG BclI
         D   I   M   L     N   K   E     E   T   K     K   E   N   S     F   E   M     Q   K   G
961      GATATAATGT     TAAACAAAGA     GGAGACGAAG     AAAGAAAACA     GCTTTGAAAT     GCAAAAAGGT BclI
         ~~~~
         D   Q   N   P     Q   I   A     A   H   V     I   S   E   A     S   S   K     T   T   S
1021     GATCAGAATC     CTCAAATTGC     GGCACATGTC     ATAAGTGAGG     CCAGCAGTAA     AACAACATCT V   L   Q   W     A   E   K     G   Y   Y     T   M   S   N     N   L   V     T   L   E
1081     GTGTTACAGT     GGGCTGAAAA     AGGATACTAC     ACCATGAGCA     ACAACTTGGT     AACCCTGGAA N   G   K   Q     L   T   V     K   R   Q     G   L   Y   Y     I   Y   A     Q   V   T
1141     AATGGGAAAC     AGCTGACCGT     TAAAAGACAA     GGACTCTATT     ATATCTATGC     CCAAGTCACC HindIII
                          ~~~~~~~
         F   C   S   N     R   E   A     S   S   Q     A   P   F   I     A   S   L     C   L   K
1201     TTCTGTTCCA     ATCGGGAAGC     TTCGAGTCAA     GCTCCATTTA     TAGCCAGCCT     CTGCCTAAAG S   P   G   R     F   E   R     I   L   L     R   A   A   N     T   H   S     S   A   K
1261     TCCCCCGGTA     GATTCGAGAG     AATCTTACTC     AGAGCTGCAA     ATACCCACAG     TTCCGCCAAA P   C   G   Q     Q   S   I     H   L   G     G   V   F   E     L   Q   P     G   A   S
1321     CCTTGCGGGC     AACAATCCAT     TCACTTGGGA     GGAGTATTTG     AATTGCAACC     AGGTGCTTCG NcoI
                                                                    ~~~~~~~
         V   F   V   N     V   T   D     P   S   Q     V   S   H   G     T   G   F     T   S   F
1381     GTGTTTGTCA     ATGTGACTGA     TCCAAGCCAA     GTGAGCCATG     GCACTGGCTT     CACGTCCTTT XhoI            XbaI
                          ~~~~~~          ~~~~
         G   L   L   K     L   E   *      *   S   R
1441     GGCTTACTCA     AACTCGAGTG     ATAATCTAGA
```

FIG. 7C

2H7scFv-CD154 S4 cDNA and predicted amino acid sequence:

```
        HindIII      NcoI
        ~~~~~~       ~~~~~~2H7 V_L Leader Peptide→
                         M   D   F    Q   V   Q    I   F   S    L   L   I    S   A   S
    1   AAGCTTGCCG  CC    ATGGATTT  TCAAGTGCAG  ATTTTCAGCT  TCCTGCTAAT  CAGTGCTTCA 2H7 V_L →
         V   I   I    A   R   G    Q   I   V    L   S   Q    S   P   A    I   L   S   A   S
   61   GTCATAATTG  CCAGAGGACA  AATTGTTCTC  TCCCAGTCTC  CAGCAATCCT  GTCTGCATCT P   G   E    K   V   T    M   T   C    R   A   S    S   S   V    S   Y   M   H   W
  121   CCAGGGGAGA  AGGTCACAAT  GACTTGCAGG  GCCAGCTCAA  GTGTAAGTTA  CATGCACTGG BamHI
                     ~~~~~~~
         Y   Q   Q    K   P   G    S   S   P    K   P   W    I   Y   A    P   S   N   L   A
  181   TACCAGCAGA  AGCCAGGATC  CTCCCCCAAA  CCCTGGATTT  ATGCCCCATC  CAACCTGGCT S   G   V    P   A   R    F   S   G    S   G   S    G   T   S    Y   S   L   T   I
  241   TCTGGAGTCC  CTGCTCGCTT  CAGTGGCAGT  GGGTCTGGGA  CCTCTTACTC  TCTCACAATC S   R   V    E   A   E    D   A   A    T   Y   Y    C   Q   Q    W   S   F   N   P
  301   AGCAGAGTGG  AGGCTGAAGA  TGCTGCCACT  TATTACTGCC  AGCAGTGGAG  TTTTAACCCA (Gly_4Ser)_3 Linker →
         P   T   F    G   A   G    T   K   L    E   L   K    G   G   G    G   S   G   G   G
  361   CCCACGTTCG  GTGCTGGGAC  CAAGCTGGAG  CTGAAAGGTG  GCGGTGGCTC  GGGCGGTGGT 2H7 V_H →
         G   S   G    G   G   S    S   Q   A    Y   L   Q    Q   S   G    A   E   L   V
  421   GGATCTGGAG  GAGGTGGGAG  CTCTCAGGCT  TATCTACAGC  AGTCTGGGGC  TGAGCTGGTG R   P   G    A   S   V    K   M   S    C   K   A    S   G   Y    T   F   T   S   Y
  481   AGGCCTGGGG  CCTCAGTGAA  GATGTCCTGC  AAGGCTTCTG  GCTACACATT  TACCAGTTAC N   M   H    W   V   K    Q   T   P    R   Q   G    L   E   W    I   G   A   I   Y
  541   AATATGCACT  GGGTAAAGCA  GACACCTAGA  CAGGGCCTGG  AATGGATTGG  AGCTATTTAT P   G   N    G   D   T    S   Y   N    Q   K   F    K   G   K    A   T   L   T   V
  601   CCAGGAAATG  GTGATACTTC  CTACAATCAG  AAGTTCAAGG  GCAAGGCCAC  ACTGACTGTA D   K   S    S   S   T    A   Y   M    Q   L   S    S   L   T    S   E   D   S   A
  661   GACAAATCCT  CCAGCACAGC  CTACATGCAG  CTCAGCAGCC  TGACATCTGA  AGACTCTGCG V   Y   F    C   A   R    V   V   Y    Y   S   N    S   Y   W    Y   F   D   V   W
  721   GTCTATTTCT  GTGCAAGAGT  GGTGTACTAT  AGTAACTCTT  ACTGGTACTT  CGATGTCTGG
```

FIG. 7D human CD154/amino acid 108 →

```
                       Bcl/Bam hybrid site                         BclI
       G  T  G  T     T  V  T     V  S  D     P  E  N     S  F  E  M  Q  K  G
781    GGCACAGGGA  CCACGGTCAC  CGTCTCTGAT  CCAGAAAACA  GCTTTGAAAT  GCAAAAAGGT BclI
~~~~~
       D  Q  N  P     Q  I  A     H  V        I  S  E  A     S  S  K     T  T  S
841    GATCAGAATC  CTCAAATTGC  GGCACATGTC  ATAAGTGAGG  CCAGCAGTAA  AACAACATCT V  L  Q  W     A  E  K     G  Y  Y     T  M  S  N     N  L  V     T  L  E
901    GTGTTACAGT  GGGCTGAAAA  AGGATACTAC  ACCATGAGCA  ACAACTTGGT  AACCCTGGAA N  G  K     Q  L  T  V     K  R  Q     G  L  Y  Y     I  Y  A     Q  V  T
961    AATGGGAAAC  AGCTGACCGT  TAAAAGACAA  GGACTCTATT  ATATCTATGC  CCAAGTCACC HindIII
                  ~~~~~~~
       F  C  S  N     R  E  A     S  S  Q     A  P  F  I     A  S  L     C  L  K
1021   TTCTGTTCCA  ATCGGGAAGC  TTCGAGTCAA  GCTCCATTTA  TAGCCAGCCT  CTGCCTAAAG S  P  G  R     F  E  R     I  L  L     R  A  A  N     T  H  S     S  A  K
1081   TCCCCCGGTA  GATTCGAGAG  AATCTTACTC  AGAGCTGCAA  ATACCCACAG  TTCCGCCAAA P  C  G  Q     Q  S  I     H  L  G     V  F  E        L  Q  P     G  A  S
1141   CCTTGCGGGC  AACAATCCAT  TCACTTGGGA  GGAGTATTTG  AATTGCAACC  AGGTGCTTCG NcoI
                                                       ~~~~~~~
       V  F  V  N     V  T  D     P  S  Q     V  S  H  G     T  G  F     T  S  F
1201   GTGTTTGTCA  ATGTGACTGA  TCCAAGCCAA  GTGAGCCATG  GCACTGGCTT  CACGTCCTTT XhoI           XbaI
                  ~~~~~~         ~~~~
       G  L  L  K     L  E  *     *  S  R
1261   GGCTTACTCA  AACTCGAGTG  ATAATCTAGA
```

......control supernatant ___2H7scFv-CD154 supernatant

| Day | Monkey J99231 LFE(1:40) | Concentration (μg/mL) | Monkey K99334 LFE(1:40) | Concentration (μg/mL) |
|---|---|---|---|---|
| Injection -7 | 2.41 | <0.6μg/mL | 1.51 | <0.4μg/mL |
| 0 | 2.22 | <0.6μg/mL | 1.63 | <0.4μg/mL |
| Injection 1 | 73.8 | 220μg/mL | 44.4 | 100μg/mL |
| 3 | 20.0 | 28μg/mL | 40.2 | 80μg/mL |
| 7 | 15.6 | 24μg/mL | 15.7 | 24μg/mL |
| 8 | 39.1 | 80μg/mL | 42.6 | 92μg/mL |
| 10 | 11.5 | 18μg/mL | 2.74 | 1.2μg/mL |
| 14 | 2.05 | 0.6mg/mL | 1.96 | 0.6μg/mL |

Standard Curve of HD37 scFvIg Derivative Binding to B Cells

| Clone/Isolate | Mean LFE at 1:100 | Estimated Concentration |
|---|---|---|
| Bulk IgAHWTG1C | 11.2 | > 60 ug/ml |
| 1B2 | 10.4 | >50 ug/ml |
| 6C5 | 10.5 | >50 ug/ml |
| 4B1 | 8.6 | >40 ug/ml |
| Bulk MHWTG1C | 10.9 | > 50 ug/ml |
| 2G8 | 10.6 | > 50 ug/ml |
| 3F3 | 8.3 | >40 ug/ml |
| 3D9 | 11.1 | > 60 ug/ml |

| Construct | Mean LFE 1:20 | Estimated Concentration |
|---|---|---|
| L6IgAHWTG1C unamplified CHO sup | 51.1 | 6.25 ug/ml |
| L6IgGMHWTG1C unamplified CHO sup | 23.0 | 3.2 ug/ml |

A. 2H7 (anti-CD20) scFv Derivatives

B. G28-1 (anti-CD37) scFv Derivatives

C. HD37 (anti-CD19) scFv Derivatives

SEQUENCE LISTING

<160> NUMBER OF SEQ ID NOS: 38

<210> SEQ ID NO 1
<211> LENGTH: 812
<212> TYPE: DNA
<213> ORGANISM: Artificial Sequence
<220> FEATURE:
<223> OTHER INFORMATION: SYNTHETIC MOUSE SCFV FUSION GENE
<220> FEATURE:
<221> NAME/KEY: sig_peptide
<222> LOCATION: (13)..(78)
<220> FEATURE:
<221> NAME/KEY: V_region
<222> LOCATION: (79)..(396)
<223> OTHER INFORMATION: light chain variable region for anti-CD20 scFv
<220> FEATURE:
<221> NAME/KEY: misc_feature
<222> LOCATION: (397)..(444)
<223> OTHER INFORMATION: asp-gly3ser(gly4ser)2-ser peptide linker
<220> FEATURE:
<221> NAME/KEY: V_region
<222> LOCATION: (445)..(808)
<223> OTHER INFORMATION: heavy chain variable region for anti-CD20 scFv

<400> SEQUENCE: 1
aagcttgccg ccatggattt tcaagtgcag attttcagct tcctgctaat cagtgcttca        60
gtcataattg ccagaggaca aattgttctc tcccagtctc cagcaatcct gtctgcatct       120
ccaggggaga aggtcacaat gacttgcagg gccagctcaa gtgtaagtta catgcactgg       180
taccagcaga agccaggatc ctcccccaaa ccctggattt atgccccatc caacctggct       240
tctggagtcc ctgctcgctt cagtggcagt gggtctggga cctcttactc tctcacaatc       300
agcagagtgg aggctgaaga tgctgccact tattactgcc agcagtggag ttttaaccca       360
cccacgttcg gtgctgggac caagctggag ctgaaaggtg gcggtggctc gggcggtggt       420
ggatctggag gaggtgggag ctctcaggct tatctacagc agtctggggc tgagctggtg       480
aggcctgggg cctcagtgaa gatgtcctgc aaggcttctg gctacacatt taccagttac       540
aatatgcact gggtaaagca gacacctaga cagggcctgg aatggattgg agctatttat       600
ccaggaaatg gtgatacttc ctacaatcag aagttcaagg gcaaggccac actgactgta       660
gacaaatcct ccagcacagc ctacatgcag ctcagcagcc tgacatctga agactctgcg       720
gtctatttct gtgcaagagt ggtgtactat agtaactctt actggtactt cgatgtctgg       780
ggcacaggga ccacggtcac cgtctctgat ca                                     812

<210> SEQ ID NO 2
<211> LENGTH: 1518
<212> TYPE: DNA
<213> ORGANISM: Artificial Sequence
<220> FEATURE:
<223> OTHER INFORMATION: SYNTHETIC MOUSE HUMAN CHIMERIC FUSION GENE
<220> FEATURE:
<221> NAME/KEY: misc_feature
<222> LOCATION: (13)..(807)
<223> OTHER INFORMATION: MURINE ANTI-HUMAN CD20 scFv
<220> FEATURE:
<221> NAME/KEY: C_region
<222> LOCATION: (808)..(1513)
<223> OTHER INFORMATION: HUMAN IgG1 Fc TAIL, WILD TYPE HINGE, CH2 AND
      CH3

<400> SEQUENCE: 2
aagcttgccg ccatggattt tcaagtgcag attttcagct tcctgctaat cagtgcttca        60
gtcataattg ccagaggaca aattgttctc tcccagtctc cagcaatcct gtctgcatct       120

```
ccaggggaga aggtcacaat gacttgcagg gccagctcaa gtgtaagtta catgcactgg      180
taccagcaga agccaggatc ctcccccaaa ccctggattt atgccccatc caacctggct      240
tctggagtcc ctgctcgctt cagtggcagt gggtctggga cctcttactc tctcacaatc      300
agcagagtgg aggctgaaga tgctgccact tattactgcc agcagtggag ttttaaccca      360
cccacgttcg gtgctgggac caagctggag ctgaaagatg gcggtggctc gggcggtggt      420
ggatctggag gaggtgggag ctctcaggct tatctacagc agtctggggc tgagctggtg      480
aggcctgggg cctcagtgaa gatgtcctgc aaggcttctg gctacacatt taccagttac      540
aatatgcact gggtaaagca gacacctaga cagggcctgg aatggattgg agctatttat      600
ccaggaaatg gtgatacttc ctacaatcag aagttcaagg gcaaggccac actgactgta      660
gacaaatcct ccagcacagc ctacatgcag ctcagcagcc tgacatctga agactctgcg      720
gtctatttct gtgcaagagt ggtgtactat agtaactctt actggtactt cgatgtctgg      780
ggcacaggga ccacggtcac cgtctctgat caggagccca atcttgtga caaaactcac       840 acatgcccac cgtgcccagc acctgaactc ctggggggac cgtcagtctt cctcttcccc      900
ccaaaaccca aggacaccct catgatctcc cggacccctg aggtcacatg cgtggtggtg      960
gacgtgagcc acgaagaccc tgaggtcaag ttcaactggt acgtggacgg cgtggaggtg     1020
cataatgcca agacaaagcc gcgggaggag cagtacaaca gcacgtaccg tgtggtcagc     1080
gtcctcaccg tcctgcacca ggactggctg aatggcaagg agtacaagtg caaggtctcc     1140
aacaaagccc tcccagcccc catcgagaaa acaatctcca agccaaagg gcagccccga     1200 gaaccacagg tgtacaccct gcccccatcc cgggatgagc tgaccaagaa ccaggtcagc     1260
ctgacctgcc tggtcaaagg cttctatccc agcgacatcg ccgtggagtg ggagagcaat     1320
gggcagccgg agaacaacta caagaccacg cctcccgtgc tggactccga cggctccttc     1380
ttcctctaca gcaagctcac cgtggacaag agcaggtggc agcagggaa cgtcttctca     1440 tgctccgtga tgcatgaggc tctgcacaac cactacacgc agaagagcct ctccctgtct     1500
ccgggtaaat gatctaga                                                  1518
```

<210> SEQ ID NO 3
<211> LENGTH: 1518
<212> TYPE: DNA
<213> ORGANISM: Artificial Sequence
<220> FEATURE:
<223> OTHER INFORMATION: SYNTHETIC MOUSE-HUMAN CHIMERIC FUSION GENE
<220> FEATURE:
<221> NAME/KEY: misc_feature
<222> LOCATION: (13)..(807)
<223> OTHER INFORMATION: MOUSE ANTI-HUMAN CD20 SCFV
<220> FEATURE:
<221> NAME/KEY: C_region
<222> LOCATION: (808)..(1513)
<223> OTHER INFORMATION: HINGE CYSTEINES (826-829; 844-847; 853-856)
    MUTATED TO SERINES PROLINE TO SERINE MUTATION (880-883) IN CH2
    DISRUPTS EFFECTOR FUNCTION

<400> SEQUENCE: 3

```
aagcttgccg ccatggattt tcaagtgcag attttcagct tcctgctaat cagtgcttca       60
gtcataattg ccagaggaca aattgttctc tcccagtctc cagcaatcct gtctgcatct      120
ccaggggaga aggtcacaat gacttgcagg gccagctcaa gtgtaagtta catgcactgg      180
taccagcaga agccaggatc ctcccccaaa ccctggattt atgccccatc caacctggct      240
tctggagtcc ctgctcgctt cagtggcagt gggtctggga cctcttactc tctcacaatc      300
agcagagtgg aggctgaaga tgctgccact tattactgcc agcagtggag ttttaaccca      360
```

```
cccacgttcg gtgctgggac caagctggag ctgaaagatg gcggtggctc gggcggtggt    420
ggatctggag gaggtgggag ctctcaggct tatctacagc agtctggggc tgagctggtg    480
aggcctgggg cctcagtgaa gatgtcctgc aaggcttctg gctacacatt taccagttac    540
aatatgcact gggtaaagca gacacctaga cagggcctgg aatggattgg agctatttat    600
ccaggaaatg gtgatacttc ctacaatcag aagttcaagg gcaaggccac actgactgta    660
gacaaatcct ccagcacagc ctacatgcag ctcagcagcc tgacatctga agactctgcg    720
gtctatttct gtgcaagagt ggtgtactat agtaactctt actggtactt cgatgtctgg    780
ggcacaggga ccacggtcac cgtctctgat caggagccca atcttctga caaaactcac    840 acatccccac cgtccccagc acctgaactc ctggggggat cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg   1020
cataatgcca agacaaagcc gcgggaggag cagtacaaca gcacgtaccg tgtggtcagc   1080
gtcctcaccg tcctgcacca ggactggctg aatggcaagg agtacaagtg caaggtctcc   1140
aacaaagccc tccagccccc catcgagaaa acaatctcca agccaaagg gcagccccga   1200 gaaccacagg tgtacaccct gcccccatcc cgggatgagc tgaccaagaa ccaggtcagc   1260
ctgacctgcc tggtcaaagg cttctatccc agcgacatcg ccgtggagtg ggagagcaat   1320
gggcagccgg agaacaacta caagaccacg cctcccgtgc tggactccga cggctccttc   1380
ttcctctaca gcaagctcac cgtggacaag agcaggtggc agcaggggaa cgtcttctca   1440
tgctccgtga tgcatgaggc tctgcacaac cactacacg agaagagcct ctccctgtct   1500
ccgggtaaat gatctaga                                                 1518
```

<210> SEQ ID NO 4
<211> LENGTH: 1518
<212> TYPE: DNA
<213> ORGANISM: Artificial Sequence
<220> FEATURE:
<223> OTHER INFORMATION: SYNTHETIC MOUSE-HUMAN CHIMERIC FUSION GENE
<220> FEATURE:
<221> NAME/KEY: misc_feature
<222> LOCATION: (13)..(807)
<223> OTHER INFORMATION: MOUSE ANTI-HUMAN CD20 SCFV
<220> FEATURE:
<221> NAME/KEY: C_region
<222> LOCATION: (808)..(1513)
<223> OTHER INFORMATION: HINGE CYSTEINES MUTATED TO SERINES (826-829; 844-847; 853-856) WILD TYPE CH2 AND CH3 DOMAINS MEDIATE EFFECTOR FUNCTIONS

<400> SEQUENCE: 4

```
aagcttgccg ccatggattt tcaagtgcag attttcagct tcctgctaat cagtgcttca     60
gtcataattg ccagaggaca aattgttctc tcccagtctc cagcaatcct gtctgcatct    120
ccaggggaga aggtcacaat gacttgcagg gccagctcaa gtgtaagtta catgcactgg    180
taccagcaga agccaggatc ctcccccaaa ccctggattt atgccccatc caacctggct    240
tctggagtcc ctgctcgctt cagtggcagt gggtctggga cctcttactc tctcacaatc    300
agcagagtgg aggctgaaga tgctgccact tattactgcc agcagtggag ttttaaccca    360
cccacgttcg gtgctgggac caagctggag ctgaaagatg gcggtggctc gggcggtggt    420
ggatctggag gaggtgggag ctctcaggct tatctacagc agtctggggc tgagctggtg    480
aggcctgggg cctcagtgaa gatgtcctgc aaggcttctg gctacacatt taccagttac    540
aatatgcact gggtaaagca gacacctaga cagggcctgg aatggattgg agctatttat    600
```

```
ccaggaaatg gtgatacttc ctacaatcag aagttcaagg gcaaggccac actgactgta     660
gacaaatcct ccagcacagc ctacatgcag ctcagcagcc tgacatctga agactctgcg     720
gtctatttct gtgcaagagt ggtgtactat agtaactctt actggtactt cgatgtctgg     780
ggcacaggga ccacggtcac cgtctctgat caggagccca atcttctga caaaactcac     840 acatccccac cgtccccagc acctgaactc ctggggggac cgtcagtctt cctcttcccc     900
ccaaaaccca aggacaccct catgatctcc cggacccctg aggtcacatg cgtggtggtg     960
gacgtgagcc acgaagaccc tgaggtcaag ttcaactggt acgtggacgg cgtggaggtg    1020
cataatgcca agacaaagcc gcgggaggag cagtacaaca gcacgtaccg tgtggtcagc    1080
gtcctcaccg tcctgcacca ggactggctg aatggcaagg agtacaagtg caaggtctcc    1140
aacaaagccc tcccagcccc catcgagaaa acaatctcca aagccaaagg gcagccccga    1200
gaaccacagg tgtacaccct gcccccatcc cgggatgagc tgaccaagaa ccaggtcagc    1260
ctgacctgcc tggtcaaagg cttctatccc agcgacatcg ccgtggagtg ggagagcaat    1320
gggcagccgg agaacaacta caagaccacg cctcccgtgc tggactccga cggctccttc    1380
ttcctctaca gcaagctcac cgtggacaag agcaggtggc agcaggggaa cgtcttctca    1440
tgctccgtga tgcatgaggc tctgcacaac cactacacgc agaagagcct ctccctgtct    1500
ccgggtaaat gatctaga                                                  1518
```

<210> SEQ ID NO 5
<211> LENGTH: 1524
<212> TYPE: DNA
<213> ORGANISM: Artificial Sequence
<220> FEATURE:
<223> OTHER INFORMATION: SYNTHETIC MOUSE HUMAN CHIMERIC FUSION GENE
<220> FEATURE:
<221> NAME/KEY: misc_feature
<222> LOCATION: (1)..(796)
<223> OTHER INFORMATION: MOUSE ANTI HUMAN CD20 SCFV
<220> FEATURE:
<221> NAME/KEY: N_region
<222> LOCATION: (797)..(864)
<223> OTHER INFORMATION: HUMAN IGA HINGE REGION
<220> FEATURE:
<221> NAME/KEY: C_region
<222> LOCATION: (865)..(1518)
<223> OTHER INFORMATION: HUMAN IGG1 CH2 AND CH3 WILD TYPE FC DOMAIN

<400> SEQUENCE: 5

```
atggatttc aagtgcagat tttcagcttc ctgctaatca gtgcttcagt cataattgcc      60
agaggacaaa ttgttctctc ccagtctcca gcaatcctgt ctgcatctcc aggggagaag    120
gtcacaatga cttgcagggc cagctcaagt gtaagttaca tgcactggta ccagcagaag    180
ccaggatcct cccccaaacc ctggatttat gccccatcca acctggcttc tggagtccct    240
gctcgcttca gtggcagtgg gtctgggacc tcttactctc tcacaatcag cagagtggag    300
gctgaagatg ctgccactta ttactgccag cagtggagtt ttaacccacc cacgttcggt    360
gctgggacca agctggagct gaaagatggc ggtggctcgg cggtggtgg atctggagga    420 ggtgggagct ctcaggctta tctacagcag tctggggctg agctggtgag gcctggggcc    480
tcagtgaaga tgtcctgcaa ggcttctggc tacacattta ccagttacaa tatgcactgg    540
gtaaagcaga cacctagaca gggcctggaa tggattggag ctatttatcc aggaaatggt    600
gatacttcct acaatcagaa gttcaagggc aaggccacac tgactgtaga caaatcctcc    660
agcacagcct acatgcagct cagcagcctg acatctgaag actctgcggt ctatttctgt    720
gcaagagtgg tgtactatag taactcttac tggtacttcg atgtctgggg cacagggacc    780
```

-continued

```
acggtcaccg tctctgatca gccagttccc tcaactccac ctaccccatc tccctcaact    840
ccacctaccc catctccctc atgcgcacct gaactcctgg ggggaccgtc agtcttcctc    900
ttccccccaa acccaagga caccctcatg atctcccgga cccctgaggt cacatgcgtg    960
gtggtggacg tgagccacga agaccctgag gtcaagttca actggtacgt ggacggcgtg   1020
gaggtgcata atgccaagac aaagccgcgg gaggagcagt acaacagcac gtaccgtgtg   1080
gtcagcgtcc tcaccgtcct gcaccaggac tggctgaatg gcaaggagta caagtgcaag   1140
gtctccaaca aagccctccc agccccatc gagaaaacaa tctccaaagc caaagggcag    1200
ccccgagaac acaggtgta caccctgccc ccatcccggg atgagctgac caagaaccag   1260
gtcagcctga cctgcctggt caaaggcttc tatcccagcg acatcgccgt ggagtgggag   1320
agcaatgggc agccggagaa caactacaag accacgcctc ccgtgctgga ctccgacggc   1380
tccttcttcc tctacagcaa gctcaccgtg gacaagagca ggtggcagca ggggaacgtc   1440
ttctcatgct ccgtgatgca tgaggctctg cacaaccact acacgcagaa gagcctctcc   1500
ctgtctccgg gtaaatgatc taga                                          1524
```

<210> SEQ ID NO 6
<211> LENGTH: 711
<212> TYPE: DNA
<213> ORGANISM: Artificial Sequence
<220> FEATURE:
<223> OTHER INFORMATION: SYNTHETIC HUMAN PARTIAL FUSION GENE
<220> FEATURE:
<221> NAME/KEY: misc_feature
<222> LOCATION: (1)..(705)
<223> OTHER INFORMATION: HINGE CYSTEINES MUTATED TO SERINES (19-21; 37-39; 46-48)

<400> SEQUENCE: 6

```
gatcaggagc ccaaatcttc tgacaaaact cacacatccc caccgtcccc agcacctgaa     60
ctcctggggg gaccgtcagt cttcctcttc cccccaaaac ccaaggacac cctcatgatc    120
tcccggaccc ctgaggtcac atgcgtggtg gtggacgtga gccacgaaga ccctgaggtc    180
aagttcaact ggtacgtgga cggcgtggag gtgcataatg ccaagacaaa gccgcgggag    240
gagcagtaca acagcacgta ccgtgtggtc agcgtcctca ccgtcctgca ccaggactgg    300
ctgaatggca aggagtacaa gtgcaaggtc tccaacaaag ccctcccagc cccatcgag    360
aaaacaatct ccaaagccaa agggcagccc cgagaaccac aggtgtacac cctgccccca    420
tcccgggatg agctgaccaa gaaccaggtc agcctgacct gcctggtcaa aggcttctat    480
cccagcgaca tcgccgtgga gtgggagagc aatgggcagc cggagaacaa ctacaagacc    540
acgcctcccg tgctggactc cgacggctcc ttcttcctct acagcaagct caccgtggac    600
aagagcaggt ggcagcaggg gaacgtcttc tcatgctccg tgatgcatga ggctctgcac    660
aaccactaca cgcagaagag cctctccctg tctccgggta aatgatctag a             711
```

<210> SEQ ID NO 7
<211> LENGTH: 729
<212> TYPE: DNA
<213> ORGANISM: Artificial Sequence
<220> FEATURE:
<223> OTHER INFORMATION: SYNTHETIC HUMAN PARTIAL FUSION GENE
<220> FEATURE:
<221> NAME/KEY: N_region
<222> LOCATION: (1)..(69)
<223> OTHER INFORMATION: HUMAN IGA HINGE
<220> FEATURE:
<221> NAME/KEY: C_region
<222> LOCATION: (70)..(723)
<223> OTHER INFORMATION: HUMAN WILD TYPE IGG1 CH2 AND CH3, FC

<400> SEQUENCE: 7

```
gatcagccag ttccctcaac tccacctacc ccatctccct caactccacc taccccatct      60
ccctcatgcg cacctgaact cctgggggga ccgtcagtct tcctcttccc cccaaaaccc     120
aaggacaccc tcatgatctc ccggacccct gaggtcacat gcgtggtggt ggacgtgagc     180
cacgaagacc ctgaggtcaa gttcaactgg tacgtggacg gcgtggaggt gcataatgcc     240
aagacaaagc cgcgggagga gcagtacaac agcacgtacc gtgtggtcag cgtcctcacc     300
gtcctgcacc aggactggct gaatggcaag gagtacaagt gcaaggtctc caacaaagcc     360
ctcccagccc ccatcgagaa aacaatctcc aaagccaaag ggcagccccg agaaccacag     420
gtgtacaccc tgcccccatc ccgggatgag ctgaccaaga accaggtcag cctgacctgc     480
ctggtcaaag gcttctatcc cagcgacatc gccgtggagt gggagagcaa tgggcagccg     540
gagaacaact acaagaccac gcctcccgtg ctggactccg acggctcctt cttcctctac     600
agcaagctca ccgtggacaa gagcaggtgg cagcagggga acgtcttctc atgctccgtg     660
atgcatgagg ctctgcacaa ccactacacg cagaagagcc tctccctgtc tccgggtaaa     720
tgatctaga                                                             729
```

<210> SEQ ID NO 8
<211> LENGTH: 825
<212> TYPE: DNA
<213> ORGANISM: Artificial Sequence
<220> FEATURE:
<223> OTHER INFORMATION: SYNTHETIC MOUSE SCFV FUSION GENE
<220> FEATURE:
<221> NAME/KEY: misc_feature
<222> LOCATION: (13)..(72)
<223> OTHER INFORMATION: LIGHT CHAIN LEADER PEPTIDE
<220> FEATURE:
<221> NAME/KEY: V_region
<222> LOCATION: (73)..(405)
<223> OTHER INFORMATION: LIGHT CHAIN VARIABLE DOMAIN FOR MOUSE ANTI-
      HUMAN CD19: HD37
<220> FEATURE:
<221> NAME/KEY: misc_feature
<222> LOCATION: (406)..(450)
<223> OTHER INFORMATION: SYNTHETIC (GLY4SER)3 LINKER PEPTIDE
<220> FEATURE:
<221> NAME/KEY: V_region
<222> LOCATION: (454)..(825)
<223> OTHER INFORMATION: HEAVY CHAIN VARIABLE DOMAIN FOR MOUSE ANTI-
      HUMAN CD19: HD37

<400> SEQUENCE: 8

```
aagcttgccg ccatggagac agacacactc ctgctatggg tgctgctgct ctggttcca      60 ggctccactg gtgacattgt gctgacccaa tctccagctt ctttggctgt gtctctaggg     120
cagagggcca ccatctcctg caaggccagc caaagtgttg attatgatgg tgatagttat     180
ttgaactggt accaacagat tccaggacag ccacccaaac tcctcatcta tgatgcatcc     240
aatctagttt ctgggatccc acccaggttt agtggcagtg gtctgggac agacttcacc      300 ctcaacatcc atcctgtgga aaggtggat gctgcaacct atcactgtca gcaaagtact      360
gaggatccgt ggacgttcgg tggaggcacc aagctggaaa tcaaaggtgg cggtggctcg     420
ggcggtggtg gtcgggtgg cggcggatcg tcacaggttc agctgcagca gtctggggct     480
gagctggtga ggcctgggtc ctcagtgaag atttcctgca aggcttctgg ctatgcattc     540
agtagctact ggatgaactg ggtgaagcag aggcctggac agggtcttga gtggattgga     600
cagatttggc ctggagatgg tgatactaac tacaatgaa agttcaaggg taaagccact      660
ctgactgcag acgaatcctc cagcacagcc tacatgcaac tcagcagcct agcatctgag     720
```

```
gactctgcgg tctatttctg tgcaagacgg gagactacga cggtaggccg ttattactat      780
gctatggact actggggtca aggaacctca gtcaccgtct cctca                     825
```

<210> SEQ ID NO 9
<211> LENGTH: 795
<212> TYPE: DNA
<213> ORGANISM: Artificial Sequence
<220> FEATURE:
<223> OTHER INFORMATION: SYNTHETIC MOUSE SCFV FUSION GENE
<220> FEATURE:
<221> NAME/KEY: misc_feature
<222> LOCATION: (13)..(72)
<223> OTHER INFORMATION: LIGHT CHAIN LEADER PEPTIDE SEQUENCE
<220> FEATURE:
<221> NAME/KEY: V_region
<222> LOCATION: (73)..(393)
<223> OTHER INFORMATION: LIGHT CHAIN VARIABLE DOMAIN FOR MOUSE ANTI-
      HUMAN CD37: G28-1
<220> FEATURE:
<221> NAME/KEY: misc_feature
<222> LOCATION: (394)..(441)
<223> OTHER INFORMATION: SYNTHETIC LINKER PEPTIDE ENCODED (GLY4SER)3
<220> FEATURE:
<221> NAME/KEY: V_region
<222> LOCATION: (442)..(795)
<223> OTHER INFORMATION: HEAVY CHAIN VARIABLE DOMAIN FOR MOUSE ANTI-
      HUMAN CD37: G28-1

<400> SEQUENCE: 9

```
aagcttgccg ccatggtatc cacagctcag ttccttgggt tgctgctgct gtggcttaca      60
ggtggcagat gtgacatcca gatgactcag tctccagcct ccctatctgc atctgtggga     120
gagactgtca ccatcacatg tcgaacaagt gaaaatgttt acagttattt ggcttggtat     180
cagcagaaac agggaaaatc tcctcagctc ctggtctctt ttgcaaaaac cttagcagaa     240
ggtgtgccat caaggttcag tggcagtgga tcaggcacac agttttctct gaagatcagc     300
agcctgcagc ctgaagattc tggaagttat ttctgtcaac atcattccga taatccgtgg     360
acgttcggtg gaggcaccga actggagatc aaaggtggcg gtggctcggg cggtggtggg     420
tcgggtggcg gcggatcgtc agcggtccag ctgcagcagt ctggacctga gctggaaaag     480
cctggcgctt cagtgaagat ttcctgcaag gcttctggtt actcattcac tggctacaat     540
atgaactggg tgaagcagaa taatggaaag agccttgagt ggattggaaa tattgatcct     600
tattatggtg gtactaccta caaccggaag ttcaagggca aggccacatt gactgtagac     660
aaatcctcca gcacagccta catgcagctc aagagtctga catctgagga ctctgcagtc     720
tattactgtg caagatcggt cggccctatg gactactggg gtcaaggaac ctcagtcacc     780
gtctcttctg atcag                                                      795
```

<210> SEQ ID NO 10
<211> LENGTH: 824
<212> TYPE: DNA
<213> ORGANISM: Artificial Sequence
<220> FEATURE:
<223> OTHER INFORMATION: SYNTHETIC MOUSE FUSION GENE
<220> FEATURE:
<221> NAME/KEY: sig_peptide
<222> LOCATION: (1)..(61)
<223> OTHER INFORMATION: native light chain leader peptide
<220> FEATURE:
<221> NAME/KEY: V_region
<222> LOCATION: (62)..(397)
<223> OTHER INFORMATION: LIGHT CHAIN VARIABLE DOMAIN FOR MOUSE ANTI-
      HUMAN CD22: G28-7
<220> FEATURE:
<221> NAME/KEY: misc_feature
<222> LOCATION: (398)..(445)

<223> OTHER INFORMATION: (gly4ser)3 linker peptide
<220> FEATURE:
<221> NAME/KEY: V_region
<222> LOCATION: (445)..(818)
<223> OTHER INFORMATION: HEAVY CHAIN VARIABLE DOMAIN FOR MOUSE ANTI-
HUMAN CD22: G28-7
<220> FEATURE:
<221> NAME/KEY: misc_feature
<222> LOCATION: (819)..(824)
<223> OTHER INFORMATION: BclI restriction site

<400> SEQUENCE: 10

```
atggagtcac attcccaggt ctttctctcc ctgctgctct gggtatctgg tacctgtggg      60
aacattatga tgacacagtc gccatcatct ctggctgtgt cagcaggaga aaaggtcact     120
atgaactgta agtccagtca aagtgttttc tacagttcaa atcagaggaa ttatttggcc     180
tggtatcagc agaaaccagg gcagtctccc aaattgctga tctactgggc atctactagg    240
gaatctggtg tccctgatcg cttcacaggc agtggatccg ggacagactt tactcttacc    300
atcagcagtg tacatactga agacctggca gtttattact gtcatcaatt cctctcttcg    360
tggacgttcg gtggaggcac caagctggaa atcaaaggcg tggtggttc gggtggtggt     420 ggttcgggtg gcggcggatc ttctcaggtc caactgcagc agcctggggc tgaactggtg    480
aagcctggga cttcagtgaa gctgtcctgc aaggcctctg ctacaccttt accaactac    540 tggatggtct gggtgaagca gacgcctgga gaaggccttg agtggattgg agaaattatt    600
cctagcaacg gtcgtactaa atacaatgag aagttcaaga gcaaggccac actgactgca    660
gacaaatcct cccgcacagc ctacatgcaa ctcagcagcc tggcatctga ggactctgcg    720
gtctattatt gtgcaagaga gatgtccatt attactacgg tactgactcc cggtttgctt    780
actggggcca agggactctg gtcactgtct ctgcagcctg atca                      824
```

<210> SEQ ID NO 11
<211> LENGTH: 266
<212> TYPE: PRT
<213> ORGANISM: Mus musculus
<220> FEATURE:
<221> NAME/KEY: INIT_MET
<222> LOCATION: (1)..(1)
<220> FEATURE:
<221> NAME/KEY: SIGNAL
<222> LOCATION: (1)..(22)
<220> FEATURE:
<221> NAME/KEY: DOMAIN
<222> LOCATION: (23)..(128)
<223> OTHER INFORMATION: LIGHT CHAIN VARIABLE DOMAIN FOR MOUSE ANTI-
HUMAN CD20
<220> FEATURE:
<221> NAME/KEY: SITE
<222> LOCATION: (129)..(144)
<223> OTHER INFORMATION: ASP-(GLY3SER)-(GLY4SER)2-SER LINKER PEPTIDE
<220> FEATURE:
<221> NAME/KEY: DOMAIN
<222> LOCATION: (145)..(266)
<223> OTHER INFORMATION: HEAVY CHAIN VARIABLE DOMAIN FOR MOUSE ANTI-
HUMAN CD20

<400> SEQUENCE: 11

```
Met Asp Phe Gln Val Gln Ile Phe Ser Phe Leu Leu Ile Ser Ala Ser
1               5                   10                  15

Val Ile Ile Ala Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60
```

```
Pro Lys Pro Trp Ile Tyr Ala Pro Ser Asn Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Gly Ser Gly Gly Gly Gly Ser Ser
130                 135                 140

Gln Ala Tyr Leu Gln Gln Ser Gly Ala Glu Leu Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Ser Thr Ala Tyr
210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp
                260                 265

<210> SEQ ID NO 12
<211> LENGTH: 271
<212> TYPE: PRT
<213> ORGANISM: Mus musculus
<220> FEATURE:
<221> NAME/KEY: SITE
<222> LOCATION: (1)..(271)
<223> OTHER INFORMATION: MOUSE ANTI-HUMAN CD19 SCFV

<400> SEQUENCE: 12

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Lys Ala Ser Gln Ser
            35                  40                  45

Val Asp Tyr Asp Gly Asp Ser Tyr Leu Asn Trp Tyr Gln Gln Ile Pro
        50                  55                  60

Gly Gln Pro Pro Lys Leu Leu Ile Tyr Asp Ala Ser Asn Leu Val Ser
65                  70                  75                  80

Gly Ile Pro Pro Arg Phe Ser Gly Ser Gly Ser Gly Thr Asp Phe Thr
                85                  90                  95

Leu Asn Ile His Pro Val Glu Lys Val Asp Ala Ala Thr Tyr His Cys
            100                 105                 110

Gln Gln Ser Thr Glu Asp Pro Trp Thr Phe Gly Gly Gly Thr Lys Leu
        115                 120                 125

Glu Ile Lys Gly Gly Gly Gly Ser Gly Gly Gly Gly Ser Gly Gly Gly
130                 135                 140

Gly Ser Ser Gln Val Gln Leu Gln Gln Ser Gly Ala Glu Leu Val Arg
```

-continued

```
                145                 150                 155                 160
Pro Gly Ser Ser Val Lys Ile Ser Cys Lys Ala Ser Gly Tyr Ala Phe
                    165                 170                 175

Ser Ser Tyr Trp Met Asn Trp Val Lys Gln Arg Pro Gly Gln Gly Leu
                    180                 185                 190

Glu Trp Ile Gly Gln Ile Trp Pro Gly Asp Gly Asp Thr Asn Tyr Asn
                    195                 200                 205

Gly Lys Phe Lys Gly Lys Ala Thr Leu Thr Ala Asp Glu Ser Ser Ser
                    210                 215                 220

Thr Ala Tyr Met Gln Leu Ser Ser Leu Ala Ser Glu Asp Ser Ala Val
225                 230                 235                 240

Tyr Phe Cys Ala Arg Arg Glu Thr Thr Thr Val Gly Arg Tyr Tyr Tyr
                    245                 250                 255

Ala Met Asp Tyr Trp Gly Gln Gly Thr Ser Val Thr Val Ser Ser
                    260                 265                 270

<210> SEQ ID NO 13
<211> LENGTH: 259
<212> TYPE: PRT
<213> ORGANISM: Mus musculus
<220> FEATURE:
<221> NAME/KEY: SITE
<222> LOCATION: (1)..(259)
<223> OTHER INFORMATION: MOUSE ANTI-HUMAN CD37 SCFV

<400> SEQUENCE: 13

Met Val Ser Thr Ala Gln Phe Leu Gly Leu Leu Leu Leu Trp Leu Thr
1               5                   10                  15

Gly Gly Arg Cys Asp Ile Gln Met Thr Gln Ser Pro Ala Ser Leu Ser
                    20                  25                  30

Ala Ser Val Gly Glu Thr Val Thr Ile Thr Cys Arg Thr Ser Glu Asn
                    35                  40                  45

Val Tyr Ser Tyr Leu Ala Trp Tyr Gln Gln Lys Gln Gly Lys Ser Pro
                    50                  55                  60

Gln Leu Leu Val Ser Phe Ala Lys Thr Leu Ala Glu Gly Val Pro Ser
65                  70                  75                  80

Arg Phe Ser Gly Ser Gly Ser Gly Thr Gln Phe Ser Leu Lys Ile Ser
                    85                  90                  95

Ser Leu Gln Pro Glu Asp Ser Gly Ser Tyr Phe Cys Gln His His
                    100                 105                 110

Asp Asn Pro Trp Thr Phe Gly Gly Gly Thr Glu Leu Glu Ile Lys Gly
                    115                 120                 125

Gly Gly Gly Ser Gly Gly Gly Gly Ser Gly Gly Gly Gly Ser Ser Ala
                    130                 135                 140

Val Gln Leu Gln Gln Ser Gly Pro Glu Leu Glu Lys Pro Gly Ala Ser
145                 150                 155                 160

Val Lys Ile Ser Cys Lys Ala Ser Gly Tyr Ser Phe Thr Gly Tyr Asn
                    165                 170                 175

Met Asn Trp Val Lys Gln Asn Asn Gly Lys Ser Leu Glu Trp Ile Gly
                    180                 185                 190

Asn Ile Asp Pro Tyr Tyr Gly Gly Thr Thr Tyr Asn Arg Lys Phe Lys
                    195                 200                 205

Gly Lys Ala Thr Leu Thr Val Asp Lys Ser Ser Ser Thr Ala Tyr Met
                    210                 215                 220

Gln Leu Lys Ser Leu Thr Ser Glu Asp Ser Ala Val Tyr Tyr Cys Ala
225                 230                 235                 240
```

-continued

```
Arg Ser Val Gly Pro Met Asp Tyr Trp Gly Gln Gly Thr Ser Val Thr
                245                 250                 255

Val Ser Ser

<210> SEQ ID NO 14
<211> LENGTH: 272
<212> TYPE: PRT
<213> ORGANISM: Mus musculus
<220> FEATURE:
<221> NAME/KEY: SITE
<222> LOCATION: (1)..(272)
<223> OTHER INFORMATION: MOUSE ANTI-HUMAN CD22 SCFV

<400> SEQUENCE: 14

Met Glu Ser His Ser Gln Val Phe Leu Ser Leu Leu Leu Trp Val Ser
1               5                   10                  15

Gly Thr Cys Gly Asn Ile Met Met Thr Gln Ser Pro Ser Ser Leu Ala
                20                  25                  30

Val Ser Ala Gly Glu Lys Val Thr Met Asn Cys Lys Ser Ser Gln Ser
            35                  40                  45

Val Phe Tyr Ser Ser Asn Gln Arg Asn Tyr Leu Ala Trp Tyr Gln Gln
        50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val His Thr Glu Asp Leu Ala Val Tyr
                100                 105                 110

Tyr Cys His Gln Phe Leu Ser Ser Trp Thr Phe Gly Gly Gly Thr Lys
            115                 120                 125

Leu Glu Ile Lys Gly Gly Gly Gly Ser Gly Gly Gly Gly Ser Gly Gly
        130                 135                 140

Gly Gly Ser Ser Gln Val Gln Leu Gln Gln Pro Gly Ala Glu Leu Val
145                 150                 155                 160

Lys Pro Gly Thr Ser Val Lys Leu Ser Cys Lys Ala Ser Gly Tyr Thr
                165                 170                 175

Phe Thr Asn Tyr Trp Met Val Trp Val Lys Gln Thr Pro Gly Glu Gly
                180                 185                 190

Leu Glu Trp Ile Gly Glu Ile Ile Pro Ser Asn Gly Arg Thr Lys Tyr
            195                 200                 205

Asn Glu Lys Phe Lys Ser Lys Ala Thr Leu Thr Ala Asp Lys Ser Ser
        210                 215                 220

Arg Thr Ala Tyr Met Gln Leu Ser Ser Leu Ala Ser Glu Asp Ser Ala
225                 230                 235                 240

Val Tyr Tyr Cys Ala Arg Glu Met Ser Ile Ile Thr Thr Val Leu Thr
                245                 250                 255

Pro Gly Leu Leu Thr Gly Ala Lys Gly Leu Trp Ser Leu Ser Leu Gln
                260                 265                 270

<210> SEQ ID NO 15
<211> LENGTH: 499
<212> TYPE: PRT
<213> ORGANISM: Artificial Sequence
<220> FEATURE:
<223> OTHER INFORMATION: MOUSE-HUMAN HYBRID FUSION PROTEIN
<220> FEATURE:
<221> NAME/KEY: SITE
<222> LOCATION: (1)..(265)
<223> OTHER INFORMATION: MOUSE ANTI-HUMAN CD20 SCFV: 2H7
<220> FEATURE:
```

<221> NAME/KEY: DOMAIN
<222> LOCATION: (266)..(499)
<223> OTHER INFORMATION: HUMAN IGG1 WILD TYPE HINGE, CH2, CH3 FC

<400> SEQUENCE: 15

```
Met Asp Phe Gln Val Gln Ile Phe Ser Phe Leu Leu Ile Ser Ala Ser
 1               5                  10                  15

Val Ile Ile Ala Arg Gly Gln Ile Val Leu Ser Gln Ser Pro Ala Ile
             20                  25                  30

Leu Ser Ala Ser Pro Gly Glu Lys Val Thr Met Thr Cys Arg Ala Ser
         35                  40                  45

Ser Ser Val Ser Tyr Met His Trp Tyr Gln Gln Lys Pro Gly Ser Ser
 50                  55                  60

Pro Lys Pro Trp Ile Tyr Ala Pro Ser Asn Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Gly Ser Gly Gly Gly Gly Ser Ser
130                 135                 140

Gln Ala Tyr Leu Gln Gln Ser Gly Ala Glu Leu Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Ser Thr Ala Tyr
210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp Gln Glu Pro Lys Ser Cys
            260                 265                 270

Asp Lys Thr His Thr Cys Pro Pro Cys Pro Ala Pro Glu Leu Leu Gly
        275                 280                 285

Gly Pro Ser Val Phe Leu Phe Pro Pro Lys Pro Lys Asp Thr Leu Met
290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
370                 375                 380

Glu Lys Thr Ile Ser Lys Ala Lys Gly Gln Pro Arg Glu Pro Gln Val
385                 390                 395                 400
```

```
Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
                435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys

<210> SEQ ID NO 16
<211> LENGTH: 499
<212> TYPE: PRT
<213> ORGANISM: Artificial Sequence
<220> FEATURE:
<223> OTHER INFORMATION: MOUSE-HUMAN HYBRID FUSION PROTEIN
<220> FEATURE:
<221> NAME/KEY: SITE
<222> LOCATION: (1)..(265)
<223> OTHER INFORMATION: 2H7 SCFV TARGETED TO HUMAN CD20
<220> FEATURE:
<221> NAME/KEY: DOMAIN
<222> LOCATION: (265)..(499)
<223> OTHER INFORMATION: HINGE CYSTEINES MUTATED TO SERINES (AMINO
      ACIDS 272, 278, 281)
      PROLINE IN CH2 MUTATED TO SERINE (AMINO ACID 290)

<400> SEQUENCE: 16

Met Asp Phe Gln Val Gln Ile Phe Ser Phe Leu Leu Ile Ser Ala Ser
1               5                   10                  15

Val Ile Ile Ala Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Gly Ser Gly Gly Gly Gly Ser Ser
    130                 135                 140

Gln Ala Tyr Leu Gln Gln Ser Gly Ala Glu Leu Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205
```

```
Lys Gly Lys Ala Thr Leu Thr Val Asp Lys Ser Ser Thr Ala Tyr
            210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp Gln Glu Pro Lys Ser Ser
                260                 265                 270

Asp Lys Thr His Thr Ser Pro Pro Ser Pro Ala Pro Glu Leu Leu Gly
            275                 280                 285

Gly Ser Ser Val Phe Leu Phe Pro Pro Lys Pro Lys Asp Thr Leu Met
290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
                340                 345                 350

Arg Val Val Ser Val Leu Thr Val Leu His Gln Asp Trp Leu Asn Gly
                355                 360                 365

Lys Glu Tyr Lys Cys Lys Val Ser Asn Lys Ala Leu Pro Ala Pro Ile
370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
                420                 425                 430

Trp Glu Ser Asn Gly Gln Pro Glu Asn Asn Tyr Lys Thr Thr Pro Pro
                435                 440                 445

Val Leu Asp Ser Asp Gly Ser Phe Phe Leu Tyr Ser Lys Leu Thr Val
            450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys

<210> SEQ ID NO 17
<211> LENGTH: 499
<212> TYPE: PRT
<213> ORGANISM: Artificial Sequence
<220> FEATURE:
<223> OTHER INFORMATION: MOUSE-HUMAN HYBRID FUSION PROTEIN
<220> FEATURE:
<221> NAME/KEY: SITE
<222> LOCATION: (1)..(265)
<223> OTHER INFORMATION: MOUSE ANTI-HUMAN CD20 SCFV: 2H7
<220> FEATURE:
<221> NAME/KEY: DOMAIN
<222> LOCATION: (266)..(499)
<223> OTHER INFORMATION: HINGE CYSTEINES MUTATED TO SERINES (AMINO
      ACIDS 272, 278, 281)
      CH2 AND CH3 DOMAINS ARE WILD TYPE IN SEQUENCE

<400> SEQUENCE: 17

Met Asp Phe Gln Val Gln Ile Phe Ser Phe Leu Leu Ile Ser Ala Ser
1               5                   10                  15

Val Ile Ile Ala Arg Gly Gln Ile Val Leu Ser Gln Ser Pro Ala Ile
```

-continued

```
                20                  25                  30
Leu Ser Ala Ser Pro Gly Glu Lys Val Thr Met Thr Cys Arg Ala Ser
            35                  40                  45
Ser Ser Val Ser Tyr Met His Trp Tyr Gln Gln Lys Pro Gly Ser Ser
        50                  55                  60
Pro Lys Pro Trp Ile Tyr Ala Pro Ser Asn Leu Ala Ser Gly Val Pro
65                  70                  75                  80
Ala Arg Phe Ser Gly Ser Gly Ser Gly Thr Ser Tyr Ser Leu Thr Ile
                85                  90                  95
Ser Arg Val Glu Ala Glu Asp Ala Ala Thr Tyr Tyr Cys Gln Gln Trp
            100                 105                 110
Ser Phe Asn Pro Pro Thr Phe Gly Ala Gly Thr Lys Leu Glu Leu Lys
        115                 120                 125
Asp Gly Gly Gly Ser Gly Gly Gly Ser Gly Gly Gly Ser
130                 135                 140
Gln Ala Tyr Leu Gln Gln Ser Gly Ala Glu Leu Val Arg Pro Gly Ala
145                 150                 155                 160
Ser Val Lys Met Ser Cys Lys Ala Ser Gly Tyr Thr Phe Thr Ser Tyr
                165                 170                 175
Asn Met His Trp Val Lys Gln Thr Pro Arg Gln Gly Leu Glu Trp Ile
            180                 185                 190
Gly Ala Ile Tyr Pro Gly Asn Gly Asp Thr Ser Tyr Asn Gln Lys Phe
        195                 200                 205
Lys Gly Lys Ala Thr Leu Thr Val Asp Lys Ser Ser Thr Ala Tyr
        210                 215                 220
Met Gln Leu Ser Ser Leu Thr Ser Glu Asp Ser Ala Val Tyr Phe Cys
225                 230                 235                 240
Ala Arg Val Val Tyr Tyr Ser Asn Ser Tyr Trp Tyr Phe Asp Val Trp
                245                 250                 255
Gly Thr Gly Thr Thr Val Thr Val Ser Asp Gln Glu Pro Lys Ser Ser
            260                 265                 270
Asp Lys Thr His Thr Ser Pro Pro Ser Pro Ala Pro Glu Leu Leu Gly
        275                 280                 285
Gly Pro Ser Val Phe Leu Phe Pro Pro Lys Pro Lys Asp Thr Leu Met
290                 295                 300
Ile Ser Arg Thr Pro Glu Val Thr Cys Val Val Val Asp Val Ser His
305                 310                 315                 320
Glu Asp Pro Glu Val Lys Phe Asn Trp Tyr Val Asp Gly Val Glu Val
                325                 330                 335
His Asn Ala Lys Thr Lys Pro Arg Glu Glu Gln Tyr Asn Ser Thr Tyr
            340                 345                 350
Arg Val Val Ser Val Leu Thr Val Leu His Gln Asp Trp Leu Asn Gly
        355                 360                 365
Lys Glu Tyr Lys Cys Lys Val Ser Asn Lys Ala Leu Pro Ala Pro Ile
        370                 375                 380
Glu Lys Thr Ile Ser Lys Ala Lys Gly Gln Pro Arg Glu Pro Gln Val
385                 390                 395                 400
Tyr Thr Leu Pro Pro Ser Arg Asp Glu Leu Thr Lys Asn Gln Val Ser
                405                 410                 415
Leu Thr Cys Leu Val Lys Gly Phe Tyr Pro Ser Asp Ile Ala Val Glu
            420                 425                 430
Trp Glu Ser Asn Gly Gln Pro Glu Asn Asn Tyr Lys Thr Thr Pro Pro
        435                 440                 445
```

```
Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys

<210> SEQ ID NO 18
<211> LENGTH: 505
<212> TYPE: PRT
<213> ORGANISM: Artificial Sequence
<220> FEATURE:
<223> OTHER INFORMATION: MOUSE-HUMAN FUSION PROTEIN
<220> FEATURE:
<221> NAME/KEY: SITE
<222> LOCATION: (1)..(265)
<223> OTHER INFORMATION: MOUSE ANTI-HUMAN CD20 SCFV: 2H7
<220> FEATURE:
<221> NAME/KEY: DOMAIN
<222> LOCATION: (266)..(288)
<223> OTHER INFORMATION: WILD TYPE IGA HINGE
<220> FEATURE:
<221> NAME/KEY: DOMAIN
<222> LOCATION: (289)..(505)
<223> OTHER INFORMATION: HUMAN IGG1 CH2 AND CH3 DOMAINS, WILD TYPE
      SEQUENCE

<400> SEQUENCE: 18

Met Asp Phe Gln Val Gln Ile Phe Ser Phe Leu Leu Ile Ser Ala Ser
1               5                   10                  15

Val Ile Ile Ala Arg Gly Gln Ile Val Leu Ser Gln Ser Pro Ala Ile
                20                  25                  30

Leu Ser Ala Ser Pro Gly Glu Lys Val Thr Met Thr Cys Arg Ala Ser
            35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
                100                 105                 110

Ser Phe Asn Pro Pro Thr Phe Gly Ala Gly Thr Lys Leu Glu Leu Lys
            115                 120                 125

Asp Gly Gly Gly Ser Gly Gly Gly Gly Ser Gly Gly Gly Gly Ser Ser
130                 135                 140

Gln Ala Tyr Leu Gln Gln Ser Gly Ala Glu Leu Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Ser Thr Ala Tyr
210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
```

```
                    245                 250                 255
Gly Thr Gly Thr Thr Val Thr Val Ser Asp Gln Pro Val Pro Ser Thr
                260                 265                 270
Pro Pro Thr Pro Ser Pro Ser Thr Pro Pro Thr Pro Ser Pro Ser Cys
            275                 280                 285
Ala Pro Glu Leu Leu Gly Gly Pro Ser Val Phe Leu Phe Pro Pro Lys
        290                 295                 300
Pro Lys Asp Thr Leu Met Ile Ser Arg Thr Pro Glu Val Thr Cys Val
305                 310                 315                 320
Val Val Asp Val Ser His Glu Asp Pro Glu Val Lys Phe Asn Trp Tyr
                325                 330                 335
Val Asp Gly Val Glu Val His Asn Ala Lys Thr Lys Pro Arg Glu Glu
                340                 345                 350
Gln Tyr Asn Ser Thr Tyr Arg Val Val Ser Val Leu Thr Val Leu His
            355                 360                 365
Gln Asp Trp Leu Asn Gly Lys Glu Tyr Lys Cys Lys Val Ser Asn Lys
        370                 375                 380
Ala Leu Pro Ala Pro Ile Glu Lys Thr Ile Ser Lys Ala Lys Gly Gln
385                 390                 395                 400
Pro Arg Glu Pro Gln Val Tyr Thr Leu Pro Pro Ser Arg Asp Glu Leu
                405                 410                 415
Thr Lys Asn Gln Val Ser Leu Thr Cys Leu Val Lys Gly Phe Tyr Pro
            420                 425                 430
Ser Asp Ile Ala Val Glu Trp Glu Ser Asn Gly Gln Pro Glu Asn Asn
        435                 440                 445
Tyr Lys Thr Thr Pro Pro Val Leu Asp Ser Asp Gly Ser Phe Phe Leu
    450                 455                 460
Tyr Ser Lys Leu Thr Val Asp Lys Ser Arg Trp Gln Gln Gly Asn Val
465                 470                 475                 480
Phe Ser Cys Ser Val Met His Glu Ala Leu His Asn His Tyr Thr Gln
                485                 490                 495
Lys Ser Leu Ser Leu Ser Pro Gly Lys
            500                 505

<210> SEQ ID NO 19
<211> LENGTH: 234
<212> TYPE: PRT
<213> ORGANISM: Homo sapiens
<220> FEATURE:
<221> NAME/KEY: DOMAIN
<222> LOCATION: (1)..(234)
<223> OTHER INFORMATION: MUTANT IGG1 HINGE (AMINO ACIDS 7, 13, 16)
      WILD TYPE CH2 AND CH3 DOMAINS
      ALTERNATIVE CARBOXY TERMINUS OF SCFVIG FUSION PROTEINS

<400> SEQUENCE: 19

Asp Gln Glu Pro Lys Ser Ser Asp Lys Thr His Thr Ser Pro Pro Ser
1               5                   10                  15
Pro Ala Pro Glu Leu Leu Gly Gly Pro Ser Val Phe Leu Phe Pro Pro
                20                  25                  30
Lys Pro Lys Asp Thr Leu Met Ile Ser Arg Thr Pro Glu Val Thr Cys
            35                  40                  45
Val Val Val Asp Val Ser His Glu Asp Pro Glu Val Lys Phe Asn Trp
        50                  55                  60
Tyr Val Asp Gly Val Glu Val His Asn Ala Lys Thr Lys Pro Arg Glu
65                  70                  75                  80
Glu Gln Tyr Asn Ser Thr Tyr Arg Val Val Ser Val Leu Thr Val Leu
```

```
                    85                  90                  95
His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
            115                 120                 125

Gln Pro Arg Glu Pro Gln Val Tyr Thr Leu Pro Pro Ser Arg Asp Glu
        130                 135                 140

Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
                180                 185                 190

Leu Tyr Ser Lys Leu Thr Val Asp Lys Ser Arg Trp Gln Gln Gly Asn
            195                 200                 205

Val Phe Ser Cys Ser Val Met His Glu Ala Leu His Asn His Tyr Thr
        210                 215                 220

Gln Lys Ser Leu Ser Leu Ser Pro Gly Lys
225                 230

<210> SEQ ID NO 20
<211> LENGTH: 240
<212> TYPE: PRT
<213> ORGANISM: Homo sapiens
<220> FEATURE:
<221> NAME/KEY: SITE
<222> LOCATION: (1)..(23)
<223> OTHER INFORMATION: ALTERNATIVE CARBOXY TERMINUS OF SCFVIG FUSION
      PROTEINS
<220> FEATURE:
<221> NAME/KEY: DOMAIN
<222> LOCATION: (24)..(240)
<223> OTHER INFORMATION: HUMAN IGG1 WILD TYPE CH2 AND CH3 FC

<400> SEQUENCE: 20

Asp Gln Pro Val Pro Ser Thr Pro Thr Pro Ser Pro Ser Thr Pro
1               5                   10                  15

Pro Thr Pro Ser Pro Ser Cys Ala Pro Glu Leu Leu Gly Gly Pro Ser
            20                  25                  30

Val Phe Leu Phe Pro Pro Lys Pro Lys Asp Thr Leu Met Ile Ser Arg
        35                  40                  45

Thr Pro Glu Val Thr Cys Val Val Val Asp Val Ser His Glu Asp Pro
50                  55                  60

Glu Val Lys Phe Asn Trp Tyr Val Asp Gly Val Glu Val His Asn Ala
65                  70                  75                  80

Lys Thr Lys Pro Arg Glu Glu Gln Tyr Asn Ser Thr Tyr Arg Val Val
                85                  90                  95

Ser Val Leu Thr Val Leu His Gln Asp Trp Leu Asn Gly Lys Glu Tyr
            100                 105                 110

Lys Cys Lys Val Ser Asn Lys Ala Leu Pro Ala Pro Ile Glu Lys Thr
        115                 120                 125

Ile Ser Lys Ala Lys Gly Gln Pro Arg Glu Pro Gln Val Tyr Thr Leu
    130                 135                 140

Pro Pro Ser Arg Asp Glu Leu Thr Lys Asn Gln Val Ser Leu Thr Cys
145                 150                 155                 160

Leu Val Lys Gly Phe Tyr Pro Ser Asp Ile Ala Val Glu Trp Glu Ser
                165                 170                 175

Asn Gly Gln Pro Glu Asn Asn Tyr Lys Thr Thr Pro Pro Val Leu Asp
```

180                 185                 190
Ser Asp Gly Ser Phe Phe Leu Tyr Ser Lys Leu Thr Val Asp Lys Ser
            195                 200                 205

Arg Trp Gln Gln Gly Asn Val Phe Ser Cys Ser Val Met His Glu Ala
    210                 215                 220

Leu His Asn His Tyr Thr Gln Lys Ser Leu Ser Leu Ser Pro Gly Lys
225                 230                 235                 240

<210> SEQ ID NO 21
<211> LENGTH: 1470
<212> TYPE: DNA
<213> ORGANISM: Artificial Sequence
<220> FEATURE:
<223> OTHER INFORMATION: MOUSE-HUMAN HYBRID
<220> FEATURE:
<221> NAME/KEY: misc_feature
<222> LOCATION: (1)..(808)
<223> OTHER INFORMATION: MOUSE ANTI-HUMAN CD20 SCFV
<220> FEATURE:
<221> NAME/KEY: misc_feature
<222> LOCATION: (814)..(1455)
<223> OTHER INFORMATION: HUMAN EXTRACELLULAR DOMAIN LONG FORM, CD154

<400> SEQUENCE: 21

```
aagcttgccg ccatggattt tcaagtgcag attttcagct tcctgctaat cagtgcttca      60
gtcataattg ccagaggaca aattgttctc tcccagtctc cagcaatcct gtctgcatct     120
ccaggggaga aggtcacaat gacttgcagg gccagctcaa gtgtaagtta catgcactgg     180
taccagcaga agccaggatc ctcccccaaa ccctggattt atgccccatc caacctggct     240
tctggagtcc ctgctcgctt cagtggcagt gggtctggga cctcttactc tctcacaatc     300
agcagagtgg aggctgaaga tgctgccact tattactgcc agcagtggag ttttaaccca     360
cccacgttcg gtgctgggac caagctggag ctgaaagatg gcggtggctc gggcggtggt     420
ggatctggag gaggtgggag ctctcaggct tatctacagc agtctgggGC tgagctggtg     480
aggcctgggg cctcagtgaa gatgtcctgc aaggcttctg gctacacatt taccagttac     540
aatatgcact gggtaaagca gacacctaga cagggcctgg aatggattgg agctatttat     600
ccaggaaatg gtgatacttc ctacaatcag aagttcaagg gcaaggccac actgactgta     660
gacaaatcct ccagcacagc ctacatgcag ctcagcagcc tgacatctga agactctgcg     720
gtctatttct gtgcaagagt ggtgtactat agtaactctt actggtactt cgatgtctgg     780
ggcacaggga ccacggtcac cgtctctgat ccaagaaggt tggacaagat agaagatgaa     840
aggaatcttc atgaagattt tgtattcatg aaaacgatac agagatgcaa cacaggagaa     900
agatccttat ccttactgaa ctgtgaggag attaaaagcc agtttgaagg ctttgtgaag     960
gatataatgt taaacaaaga ggagacgaag aaagaaaaca gctttgaaat gcaaaaaggt    1020
gatcagaatc ctcaaattgc ggcacatgtc ataagtgagg ccagcagtaa aacaacatct    1080
gtgttacagt gggctgaaaa aggatactac accatgagca caacttggt aaccctggaa    1140
aatgggaaac agctgaccgt taaaagacaa ggactctatt atatctatgc ccaagtcacc    1200
ttctgttcca atcgggaagc ttcgagtcaa gctccattta tagccagcct ctgcctaaag    1260
tcccccggta gattcgagag aatcttactc agagctgcaa atacccacag ttccgccaaa    1320
ccttgcgggc aacaatccat tcacttggga ggagtatttg aattgcaacc aggtgcttcg    1380
gtgtttgtca atgtgactga tccaagccaa gtgagccatg gcactggctt cacgtccttt    1440
ggcttactca aactcgagtg ataatctaga                                     1470
```

```
<210> SEQ ID NO 22
<211> LENGTH: 1290
<212> TYPE: DNA
<213> ORGANISM: Artificial Sequence
<220> FEATURE:
<223> OTHER INFORMATION: MOUSE-HUMAN HYBRID
<220> FEATURE:
<221> NAME/KEY: misc_feature
<222> LOCATION: (13)..(808)
<223> OTHER INFORMATION: MOUSE ANTI-HUMAN CD20 SCFV
<220> FEATURE:
<221> NAME/KEY: misc_feature
<222> LOCATION: (814)..(1275)
<223> OTHER INFORMATION: HUMAN EXTRACELLULAR DOMAIN, SHORT FORM, CD154

<400> SEQUENCE: 22
aagcttgccg ccatggattt tcaagtgcag attttcagct tcctgctaat cagtgcttca      60
gtcataattg ccagaggaca aattgttctc tcccagtctc cagcaatcct gtctgcatct     120
ccaggggaga aggtcacaat gacttgcagg gccagctcaa gtgtaagtta catgcactgg     180
taccagcaga agccaggatc ctcccccaaa ccctggattt atgccccatc caacctggct     240
tctggagtcc ctgctcgctt cagtggcagt gggtctggga cctcttactc tctcacaatc     300
agcagagtgg aggctgaaga tgctgccact tattactgcc agcagtggag ttttaaccca     360
cccacgttcg gtgctgggac caagctggag ctgaaagatg cggtggctc gggcggtggt      420 ggatctggag gagtgggag ctctcaggct tatctacagc agtctggggc tgagctggtg      480
aggcctgggg cctcagtgaa gatgtcctgc aaggcttctg gctacacatt taccagttac     540
aatatgcact gggtaaagca gacacctaga cagggcctgg aatggattgg agctatttat     600
ccaggaaatg gtgatacttc ctacaatcag aagttcaagg gcaaggccac actgactgta     660
gacaaatcct ccagcacagc ctacatgcag ctcagcagcc tgacatctga agactctgcg     720
gtctatttct gtgcaagagt ggtgtactat agtaactctt actggtactt cgatgtctgg     780
ggcacaggga ccacggtcac cgtctctgat ccagaaaaca gctttgaaat gcaaaaaggt     840
gatcagaatc ctcaaattgc ggcacatgtc ataagtgagg ccagcagtaa acaacatct      900 gtgttacagt gggctgaaaa aggatactac accatgagca caacttggt aaccctggaa      960 aatgggaaac agctgaccgt taaaagacaa ggactctatt atatctatgc ccaagtcacc     1020
ttctgttcca atcgggaagc ttcgagtcaa gctccattta tagccagcct ctgcctaaag     1080
tcccccggta gattcgagag aatcttactc agagctgcaa atacccacag ttccgccaaa     1140
ccttgcgggc aacaatccat tcacttggga ggagtatttg aattgcaacc aggtgcttcg     1200
gtgtttgtca atgtgactga tccaagccaa gtgagccatg gcactggctt cacgtccttt     1260
ggcttactca aactcgagtg ataatctaga                                     1290

<210> SEQ ID NO 23
<211> LENGTH: 43
<212> TYPE: DNA
<213> ORGANISM: Artificial Sequence
<220> FEATURE:
<223> OTHER INFORMATION: OLIGONUCLEOTIDE

<400> SEQUENCE: 23
gtcaagcttg ccgccatgga ttttcaagtg cagatttttc agc                       43

<210> SEQ ID NO 24
<211> LENGTH: 74
<212> TYPE: DNA
<213> ORGANISM: Artificial Sequence
<220> FEATURE:
<223> OTHER INFORMATION: OLIGONUCLEOTIDE
```

-continued

<400> SEQUENCE: 24
gtcgtcgagc tcccacctcc tccagatcca ccaccgcccg agccaccgcc acctttcagc    60
tccagcttgg tccc    74

<210> SEQ ID NO 25
<211> LENGTH: 37
<212> TYPE: DNA
<213> ORGANISM: Artificial Sequence
<220> FEATURE:
<223> OTHER INFORMATION: OLIGONUCLEOTIDE

<400> SEQUENCE: 25
gctgctgagc tctcaggctt atctacagca agtctgg    37

<210> SEQ ID NO 26
<211> LENGTH: 32
<212> TYPE: DNA
<213> ORGANISM: Artificial Sequence
<220> FEATURE:
<223> OTHER INFORMATION: OLIGONUCLEOTIDE

<400> SEQUENCE: 26
gttgtctgat cagagacggt gaccgtggtc cc    32

<210> SEQ ID NO 27
<211> LENGTH: 34
<212> TYPE: DNA
<213> ORGANISM: Artificial Sequence
<220> FEATURE:
<223> OTHER INFORMATION: OLIGONUCLEOTIDE

<400> SEQUENCE: 27
gttgtcggat ccagaaaaca gctttgaaat gcaa    34

<210> SEQ ID NO 28
<211> LENGTH: 44
<212> TYPE: DNA
<213> ORGANISM: Artificial Sequence
<220> FEATURE:
<223> OTHER INFORMATION: OLIGONUCLEOTIDE

<400> SEQUENCE: 28
gttgtttcta gattatcact cgagtttgag taagccaaag gacg    44

<210> SEQ ID NO 29
<211> LENGTH: 35
<212> TYPE: DNA
<213> ORGANISM: Artificial Sequence
<220> FEATURE:
<223> OTHER INFORMATION: OLIGONUCLEOTIDE

<400> SEQUENCE: 29
gttgtcggat ccaagaaggt tggacaagat agaag    35

<210> SEQ ID NO 30
<211> LENGTH: 23
<212> TYPE: DNA
<213> ORGANISM: Artificial Sequence
<220> FEATURE:
<223> OTHER INFORMATION: OLIGONUCLEOTIDE

<400> SEQUENCE: 30
gtctatataa gcagagctct ggc    23

<210> SEQ ID NO 31
<211> LENGTH: 25
<212> TYPE: DNA
<213> ORGANISM: Artificial Sequence
<220> FEATURE:
<223> OTHER INFORMATION: OLIGONUCLEOTIDE

<400> SEQUENCE: 31
cgaggctgat cagcgagctc tagca                                         25

<210> SEQ ID NO 32
<211> LENGTH: 25
<212> TYPE: DNA
<213> ORGANISM: Artificial Sequence
<220> FEATURE:
<223> OTHER INFORMATION: OLIGONUCLEOTIDE

<400> SEQUENCE: 32
ccgcaatttg aggattctga tcacc                                         25

<210> SEQ ID NO 33
<211> LENGTH: 482
<212> TYPE: PRT
<213> ORGANISM: Artificial Sequence
<220> FEATURE:
<223> OTHER INFORMATION: MOUSE-HUMAN HYBRID FUSION PROTEIN
<220> FEATURE:
<221> NAME/KEY: SITE
<222> LOCATION: (1)..(266)
<223> OTHER INFORMATION: MOUSE ANTI-HUMAN CD20 SCFV
<220> FEATURE:
<221> NAME/KEY: DOMAIN
<222> LOCATION: (268)..(481)
<223> OTHER INFORMATION: EXTRACELLULAR DOMAIN, LONG FORM, HUMAN CD154

<400> SEQUENCE: 33

Met Asp Phe Gln Val Gln Ile Phe Ser Phe Leu Leu Ile Ser Ala Ser
1               5                   10                  15

Val Ile Ile Ala Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Gly Ser Gly Gly Gly Gly Ser Ser
    130                 135                 140

Gln Ala Tyr Leu Gln Gln Ser Gly Ala Glu Leu Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

-continued

```
Lys Gly Lys Ala Thr Leu Thr Val Asp Lys Ser Ser Ser Thr Ala Tyr
            210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp Pro Arg Arg Leu Asp Lys
                260                 265                 270

Ile Glu Asp Glu Arg Asn Leu His Glu Asp Phe Val Phe Met Lys Thr
            275                 280                 285

Ile Gln Arg Cys Asn Thr Gly Glu Arg Ser Leu Ser Leu Leu Asn Cys
290                 295                 300

Glu Glu Ile Lys Ser Gln Phe Glu Gly Phe Val Lys Asp Ile Met Leu
305                 310                 315                 320

Asn Lys Glu Glu Thr Lys Lys Glu Asn Ser Phe Glu Met Gln Lys Gly
                325                 330                 335

Asp Gln Asn Pro Gln Ile Ala Ala His Val Ile Ser Glu Ala Ser Ser
            340                 345                 350

Lys Thr Thr Ser Val Leu Gln Trp Ala Glu Lys Gly Tyr Tyr Thr Met
                355                 360                 365

Ser Asn Asn Leu Val Thr Leu Glu Asn Gly Lys Gln Leu Thr Val Lys
370                 375                 380

Arg Gln Gly Leu Tyr Tyr Ile Tyr Ala Gln Val Thr Phe Cys Ser Asn
385                 390                 395                 400

Arg Glu Ala Ser Ser Gln Ala Pro Phe Ile Ala Ser Leu Cys Leu Lys
                405                 410                 415

Ser Pro Gly Arg Phe Glu Arg Ile Leu Leu Arg Ala Ala Asn Thr His
            420                 425                 430

Ser Ser Ala Lys Pro Cys Gly Gln Gln Ser Ile His Leu Gly Gly Val
            435                 440                 445

Phe Glu Leu Gln Pro Gly Ala Ser Val Phe Val Asn Val Thr Asp Pro
            450                 455                 460

Ser Gln Val Ser His Gly Thr Gly Phe Thr Ser Phe Gly Leu Leu Lys
465                 470                 475                 480

Leu Glu
```

<210> SEQ ID NO 34
<211> LENGTH: 422
<212> TYPE: PRT
<213> ORGANISM: Artificial Sequence
<220> FEATURE:
<223> OTHER INFORMATION: MOUSE-HUMAN HYBRID FUSION PROTEIN
<220> FEATURE:
<221> NAME/KEY: SITE
<222> LOCATION: (1)..(266)
<223> OTHER INFORMATION: MOUSE ANTI-HUMAN SCFV
<220> FEATURE:
<221> NAME/KEY: DOMAIN
<222> LOCATION: (268)..(421)<223> EXTRACELLULAR DOMAIN, SHORT FORM,
    HUMAN CD154

<400> SEQUENCE: 34

```
Met Asp Phe Gln Val Gln Ile Phe Ser Phe Leu Leu Ile Ser Ala Ser
1               5                   10                  15

Val Ile Ile Ala Arg Gly Gln Ile Val Leu Ser Gln Ser Pro Ala Ile
                20                  25                  30

Leu Ser Ala Ser Pro Gly Glu Lys Val Thr Met Thr Cys Arg Ala Ser
            35                  40                  45
```

Ser Ser Val Ser Tyr Met His Trp Tyr Gln Gln Lys Pro Gly Ser Ser
 50                  55                  60

Pro Lys Pro Trp Ile Tyr Ala Pro Ser Asn Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Arg Val Glu Ala Glu Asp Ala Ala Thr Tyr Tyr Cys Gln Gln Trp
             100                 105                 110

Ser Phe Asn Pro Pro Thr Phe Gly Ala Gly Thr Lys Leu Glu Leu Lys
         115                 120                 125

Asp Gly Gly Gly Ser Gly Gly Gly Ser Gly Gly Gly Gly Ser Ser
130                 135                 140

Gln Ala Tyr Leu Gln Gln Ser Gly Ala Glu Leu Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Thr Ala Tyr
210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp Pro Glu Asn Ser Phe Glu
            260                 265                 270

Met Gln Lys Gly Asp Gln Asn Pro Gln Ile Ala Ala His Val Ile Ser
        275                 280                 285

Glu Ala Ser Ser Lys Thr Thr Ser Val Leu Gln Trp Ala Glu Lys Gly
290                 295                 300

Tyr Tyr Thr Met Ser Asn Asn Leu Val Thr Leu Glu Asn Gly Lys Gln
305                 310                 315                 320

Leu Thr Val Lys Arg Gln Gly Leu Tyr Tyr Ile Tyr Ala Gln Val Thr
                325                 330                 335

Phe Cys Ser Asn Arg Glu Ala Ser Ser Gln Ala Pro Phe Ile Ala Ser
            340                 345                 350

Leu Cys Leu Lys Ser Pro Gly Arg Phe Glu Arg Ile Leu Leu Arg Ala
        355                 360                 365

Ala Asn Thr His Ser Ser Ala Lys Pro Cys Gly Gln Gln Ser Ile His
370                 375                 380

Leu Gly Gly Val Phe Glu Leu Gln Pro Gly Ala Ser Val Phe Val Asn
385                 390                 395                 400

Val Thr Asp Pro Ser Gln Val Ser His Gly Thr Gly Phe Thr Ser Phe
                405                 410                 415

Gly Leu Leu Lys Leu Glu
            420

<210> SEQ ID NO 35
<211> LENGTH: 63
<212> TYPE: DNA
<213> ORGANISM: Homo sapiens
<220> FEATURE:
<221> NAME/KEY: N_region
<222> LOCATION: (1)..(63)

<223> OTHER INFORMATION: PORTION OF HUMAN IGA HINGE DOMAIN CONTAINING
      ONLY 1 CYSTEINE

<400> SEQUENCE: 35
ccagttccct caactccacc tacccatct ccctcaactc cacctacccc atctccctca    60
tgc                                                                63

<210> SEQ ID NO 36
<211> LENGTH: 21
<212> TYPE: PRT
<213> ORGANISM: Homo sapiens

<400> SEQUENCE: 36

Pro Val Pro Ser Thr Pro Pro Thr Pro Ser Pro Ser Thr Pro Pro Thr
1               5                   10                  15

Pro Ser Pro Ser Cys
            20

<210> SEQ ID NO 37
<211> LENGTH: 763
<212> TYPE: DNA
<213> ORGANISM: Homo sapiens
<220> FEATURE:
<221> NAME/KEY: misc_feature
<222> LOCATION: (1)..(6)
<223> OTHER INFORMATION: BCLI SITE FOR FUSION TO AMIN TERMINAL SCFVS
<220> FEATURE:
<221> NAME/KEY: N_region
<222> LOCATION: (8)..(752)
<223> OTHER INFORMATION: WILD TYPE IGA HINGE, CH2, CH3 DOMAINS
      TRUNCATED TO REMOVE SECRETORY COMPONENT ATTACHMENT

<400> SEQUENCE: 37
tgatcagcca gttccctcaa ctccacctac cccatctccc tcaactccac ctaccccatc    60
tccctcatgc tgccaccccc gactgtcact gcaccgaccg ccctcgagg acctgctctt   120 aggttcagaa gcgatcctca cgtgcacact gaccggctg agagatgcct caggtgtcac   180
cttcacctgg acgccctcaa gtgggaagag cgctgttcaa ggaccacctg accgtgacct   240
ctgtggctgc tacagcgtgt ccagtgtcct gccgggctgt gccgagccat ggaaccatgg   300
gaagaccttc acttgcactg ctgcctaccc cgagtccaag accccgctaa ccgccaccct   360
ctcaaaatcc ggaaacacat tccggcccga ggtccacctg ctgccgccgc cgtcggagga   420
gctggccctg aacgagctgg tgacgctgac gtgcctggca cgtggcttca gccccaagga   480
tgtgctggtt cgctggctgc aggggtcaca ggagctgccc cgcgagaagt acctgacttg   540
ggcatcccgg caggagccca gccagggcac caccaccttc gctgtgacca gcatactgcg   600
cgtggcagcc gaggactgga gaaggggga cccttctcc tgcatggtgg ccacgaggc    660 cctgccgctg gccttcacac agaagaccat cgaccgcttg gcgggtaaac ccacccatgt   720
caatgtgtct gttgtcatgg cggaggtgga ctgataatct aga                     763

<210> SEQ ID NO 38
<211> LENGTH: 250
<212> TYPE: PRT
<213> ORGANISM: Homo sapiens
<220> FEATURE:
<221> NAME/KEY: DOMAIN
<222> LOCATION: (3)..(250)
<223> OTHER INFORMATION: TRUNCATED FORM, REMOVAL OF LAST THREE AMINO
      ACIDS THAT MEDIATE ATTACHMENT TO SECRETORY COMPONEN

<400> SEQUENCE: 38

Asp Gln Pro Val Pro Ser Thr Pro Pro Thr Pro Ser Pro Ser Thr Pro

-continued

```
 1               5              10             15
Pro Thr Pro Ser Pro Ser Cys Cys His Pro Arg Leu Ser Leu His Arg
            20              25              30
Pro Ala Leu Glu Asp Leu Leu Leu Gly Ser Glu Ala Ile Leu Thr Cys
            35              40              45
Thr Leu Thr Gly Leu Arg Asp Ala Ser Gly Val Thr Phe Thr Trp Thr
        50              55              60
Pro Ser Ser Gly Lys Ser Ala Val Gln Gly Pro Pro Asp Arg Asp Leu
65              70              75              80
Cys Gly Cys Tyr Ser Val Ser Ser Val Leu Pro Gly Cys Ala Glu Pro
            85              90              95
Trp Asn His Gly Lys Thr Phe Thr Cys Thr Ala Ala Tyr Pro Glu Ser
            100             105             110
Lys Thr Pro Leu Thr Ala Thr Leu Ser Lys Ser Gly Asn Thr Phe Arg
            115             120             125
Pro Glu Val His Leu Leu Pro Pro Ser Glu Glu Leu Ala Leu Asn
            130             135             140
Glu Leu Val Thr Leu Thr Cys Leu Ala Arg Gly Phe Ser Pro Lys Asp
145             150             155             160
Val Leu Val Arg Trp Leu Gln Gly Ser Gln Glu Leu Pro Arg Glu Lys
            165             170             175
Tyr Leu Thr Trp Ala Ser Arg Gln Glu Pro Ser Gln Gly Thr Thr Thr
            180             185             190
Phe Ala Val Thr Ser Ile Leu Arg Val Ala Ala Glu Asp Trp Lys Lys
            195             200             205
Gly Asp Thr Phe Ser Cys Met Val Gly His Glu Ala Leu Pro Leu Ala
            210             215             220
Phe Thr Gln Lys Thr Ile Asp Arg Leu Ala Gly Lys Pro Thr His Val
225             230             235             240
Asn Val Ser Val Val Met Ala Glu Val Asp
            245             250
```

BINDING DOMAIN-IMMUNOGLOBULIN FUSION PROTEINS

CROSS REFERENCE TO RELATED APPLICATIONS

This application is a continuation of U.S. application Ser. No. 10/053,530, filed Jan. 17, 2002, now pending, which claims the benefit of priority of U.S. Provisional Application No. 60/367,358 (formerly U.S. application Ser. No. 09/765,208, filed Jan. 17, 2001), the contents of which are incorporated by reference in their entirety.

BACKGROUND OF THE INVENTION

The present invention relates generally to immunologically active, recombinant binding proteins, and in particular, to molecularly engineered binding domain-immunoglobulin fusion proteins, including single chain Fv-immunoglobulin fusion proteins. The present invention also relates to compositions and methods for treating malignant conditions and B-cell disorders, including diseases characterized by autoantibody production.

An immunoglobulin molecule is composed of two identical light chains and two identical heavy chains that are joined into a macromolecular complex by interchain disulfide bonds. Intrachain disulfide bonds join different areas of the same polypeptide chain, which results in the formation of loops that along with adjacent amino acids constitute the immunoglobulin domains. Each light chain and each heavy chain has a single variable region that shows considerable variation in amino acid composition from one antibody to another. The light chain variable region, $V_L$, associates with the variable region of a heavy chain, $V_H$, to form the antigen binding site of the immunoglobulin, Fv. Light chains have a single constant region domain and heavy chains have several constant region domains. Classes IgG, IgA, and IgD have three constant region domains, which are designated CH1, CH2, and CH3, and the IgM and IgE classes have four constant region domains.

The heavy chains of immunoglobulins can be divided into three functional regions: Fd, hinge, and Fc. The Fd region comprises the $V_H$ and CH1 domains and in combination with the light chain forms Fab. The Fc fragment is generally considered responsible for the effector functions of an immunoglobulin, such as, complement fixation and binding to Fc receptors. The hinge region, found in IgG, IgA, and IgD classes, acts as a flexible spacer, allowing the Fab portion to move freely in space. In contrast to the constant regions, the hinge domains are structurally diverse, varying in both sequence and length among immunoglobulin classes and subclasses. For example, three human IgG subclasses, IgG1, IgG2, and IgG4, have hinge regions of 12-15 amino acids while IgG3 comprises approximately 62 amino acids, including 21 proline residues and 11 cysteine residues. According to crystallographic studies, the hinge can be further subdivided functionally into three regions: the upper hinge, the core, and the lower hinge (Shin et al., *Immunological Reviews* 130:87 (1992)). The upper hinge includes amino acids from the carboxyl end of CH1 to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the CH2 domain and includes residues in CH2. (Id.) The core hinge region of human IgG1 contains the sequence, Cys-Pro-Pro-Cys, which when disulfide bonds are formed results in a cyclic octapeptide believed to act as a pivot, thus conferring flexibility. The hinge region may also contain carbohydrate attachment sites. For example, IgA1 contains five carbohydrate sites within a 17 amino acid segment of the hinge region, conferring exception resistance of the hinge to intestinal proteases, considered an advantageous property for a secretory immunoglobulin.

Conformational changes permitted by the structure and flexibility of the hinge region may affect the effector functions of the Fc portion of the antibody. Three general categories of effector functions associated with the Fc region include (1) activation of the classical complement cascade, (2) interaction with effector cells, and (3) compartmentalization of immunoglobulins. The different human IgG subclasses vary in their relative efficacy to activate and amplify the steps of the complement cascade. In general, IgG1 and IgG3 most effectively fix complement, IgG2 is less effective, and IgG4 does not activate complement. Complement activation is initiated by binding of C1q, a subunit of the first component C1 in the cascade, to an antigen-antibody complex. Even though the binding site for C1q is located in the CH2 domain of the antibody, the hinge region influences the ability of the antibody to activate the cascade. For example, recombinant immunoglobulins lacking a hinge region are unable to activate complement. (Id.) Without the flexibility conferred by the hinge region, the Fab portion of the antibody bound to the antigen may not be able to adopt the conformation required to permit C1q to bind to CH2. (See id.) Studies have indicated that hinge length and segmental flexibility correlate with complement activation; however, the correlation is not absolute. Human IgG3 molecules with altered hinge regions that are as rigid as IgG4 still effectively activate the cascade.

Lack of the hinge region also affects the ability of human IgG immunoglobulins to bind Fc receptors on immune effector cells. Binding of an immunoglobulin to an Fc receptor facilitates antibody-dependent cellular cytotoxicity (ADCC), which is presumed to be an important means to eliminate tumor cells. The human IgG Fc receptor family is divided into three groups, FcγRI (CD64), which is capable of binding IgG with high affinity, FcγRII (CD32), and FcγRIII (CD16), both of which are low affinity receptors. The molecular interaction between each of the three receptors and an immunoglobulin has not been defined precisely, but experiments indicate that residues in the hinge proximal region of the CH2 domain are important to the specificity of the interaction between the antibody and the Fc receptor. In addition, IgG1 myeloma proteins and recombinant IgG3 chimeric antibodies that lack a hinge region are unable to bind FcγRI, likely because accessibility to CH2 is decreased. (Shin et al., *Intern. Rev. Immunol.* 10:177, 178-79 (1993)).

Monoclonal antibody technology and genetic engineering methods have led to rapid development of immunoglobulin molecules for diagnosis and treatment of human diseases. Protein engineering has been applied to improve the affinity of an antibody for its cognate antigen, to diminish problems related to immunogenicity, and to alter an antibody's effector functions. The domain structure of immunoglobulins is amenable to engineering, in that the antigen binding domains and the domains conferring effector functions may be exchanged between immunoglobulin classes and subclasses.

In addition, smaller immunoglobulin molecules have been constructed to overcome problems associated with whole immunoglobulin therapy. Single chain Fv (scFv) comprise the heavy chain variable domain joined via a short linker peptide to the light chain variable domain (Huston et al. *Proc. Natl. Acad. Sci. USA*, 85: 5879-83, 1988). Because of the small size of scFv molecules, they exhibit very rapid clearance from plasma and tissues and more effective penetration into tissues than whole immunoglobulin. An anti-tumor scFv showed more rapid tumor penetration and more even distribution through the tumor mass than the corresponding chimeric antibody (Yokota et al., *Cancer Res.* 52, 3402-08 (1992)). Fusion of an scFv to another molecule, such as a toxin, takes advantage of the specific antigen-binding activity and the small size of an scFv to deliver the toxin to a target tissue. (Chaudary et al., *Nature* 339:394 (1989); Batra et al., *Mol. Cell. Biol.* 11:2200 (1991)).

Despite the advantages that scFv molecules bring to serotherapy, several drawbacks to this therapeutic approach exist. While rapid clearance of scFv may reduce toxic effects in normal cells, such rapid clearance may prevent delivery of a minimum effective dose to the target tissue. Manufacturing adequate amounts of scFv for administration to patients has been challenging due to difficulties in expression and isolation of scFv that adversely affect the yield. During expression, scFv molecules lack stability and often aggregate due to pairing of variable regions from different molecules. Furthermore, production levels of scFv molecules in mammalian expression systems are low, limiting the potential for efficient manufacturing of scFv molecules for therapy (Davis et al, *J. Biol. Chem.* 265:10410-18 (1990); Traunecker et al., *EMBO J.* 10: 3655-59 (1991)). Strategies for improving production have been explored, including addition of glycosylation sites to the variable regions (Jost, C. R. U.S. Pat. No. 5,888,773, Jost et al, *J. Biol. Chem.* 269: 26267-73 (1994)).

Conjugation or fusion of toxins to scFV provides a very potent molecule, but dosing is limited by toxicity from the toxin molecule. Toxic effects include elevation of liver enzymes and vascular leak syndrome. In addition, immunotoxins are highly immunogenic, and host antibodies generated against the toxin limit its potential for repeated treatment.

An additional disadvantage to using scFv for therapy is the lack of effector function. An scFv without the cytolytic functions, ADCC and complement dependent-cytotoxicity (CDC), associated with the constant region of an immunoglobulin may be ineffective for treating disease. Even though development of scFv technology began over 12 years ago, currently no scFv products are approved for therapy.

The benefit of antibody constant region-associated effector functions to treatment of a disease has prompted development of fusion proteins in which nonimmunoglobulin sequences are substituted for the antibody variable region. For example, CD4, the T cell surface protein recognized by HIV, was recombinantly fused to an immunoglobulin Fc effector domain. (See Sensel et al., *Chem. Immunol.* 65:129-158 (1997)). The biological activity of such a molecule will depend in part on the class or subclass of the constant region chosen. An IL-2-IgG1 fusion protein effected complement-mediated lysis of IL-2 receptor-bearing cells. (See id.). Use of immunoglobulin constant regions to construct these and other fusion proteins may also confer improved pharmacokinetic properties.

Diseases and disorders thought to be amenable to some type of immunoglobulin therapy include cancer and immune system disorders. Cancer includes a broad range of diseases, affecting approximately one in four individuals worldwide. Rapid and unregulated proliferation of malignant cells is a hallmark of many types of cancer, including hematological malignancies. Patients with a hematologic malignant condition have benefited most from advances in cancer therapy in the past two decades (Multani et al., *J. Clin. Oncology* 16: 3691-3710, 1998). Although remission rates have increased, most patients still relapse and succumb to their disease. Barriers to cure with cytotoxic drugs include tumor cell resistance and the high toxicity of chemotherapy, which prevents optimal dosing in many patients. New treatments based on targeting with molecules that specifically bind to a malignant cell, including monoclonal antibodies (mAbs), can improve effectiveness without increasing toxicity.

Since mAbs were first described in 1975 (Kohler et al., *Nature* 256:495-97 (1975)), many patients have been treated with mAbs to antigens expressed on tumor cells. These studies have yielded important lessons regarding the selection of target antigens suitable for therapy. First and most importantly, the target antigen should not be expressed by crucial normal tissues. Fortunately, hematologic malignant cells express many antigens that are not expressed on stem cells or other essential cells. Treatment of a hematologic malignant condition that depletes both normal and malignant cells of hematological origin has been acceptable because regeneration of normal cells from progenitors occurs after therapy has ended. Second, the target antigen should be expressed on all clonogenic populations of tumor cells, and expression should persist despite the selective pressure from immunoglobulin therapy. Thus, the choice of surface idiotype for therapy of B cell malignancy has been limited by the outgrowth of tumor cell variants with altered surface idiotype expression even though the antigen exhibits a high degree of tumor selectivity (Meeker et al., *N. Engl. J. Med.* 312:1658-65 (1985)). Third, the selected antigen must traffic properly after an immunoglobulin binds to it. Shedding or internalization of a target antigen after an immunoglobulin binds to the antigen may allow tumor cells to escape destruction, thus limiting the effectiveness of serotherapy. Fourth, binding of an immunoglobulin to target antigens that transmit activation signals may result in improved functional responses in tumor cells that lead to growth arrest and apoptosis. While all of these properties are important, the triggering of apoptosis after an immunoglobulin binds to the antigen may be a critical factor in achieving successful serotherapy.

Antigens that have been tested as targets for serotherapy of B and T cell malignancies include Ig idiotype (Brown et al., *Blood* 73:651-61 (1989)), CD19 (Hekman et al., *Cancer Immunol. Immunother.* 32:364-72 (1991); Vlasveld et al., *Cancer Immunol. Immunother.* 40: 37-47 (1995)), CD20 (Press et al., *Blood* 69: 584-91 (1987); Maloney et al., *J. Clin. Oncol.* 15:3266-74, (1997)) CD21 (Scheinberg et. al., *J. Clin. Oncol.* 8:792-803, (1990)), CD5 (Dillman et. al., *J. Biol. Respn. Mod.* 5:394-410 (1986)), and CD52 (CAMPATH) (Pawson et al., *J. Clin. Oncol.* 15:2667-72, (1997)). Of these, the most success has been obtained using CD20 as a target for therapy of B cell lymphomas. Each of the other targets has been limited by the biological properties of the antigen. For example, surface idiotype can be altered through somatic mutation, allowing tumor cell escape. CD5, CD21, and CD19 are rapidly internalized after mAb binding, allowing tumor cells to escape destruction unless mAbs are conjugated with toxin molecules. CD22 is expressed on only a subset of B cell lymphomas, while CD52 is expressed on both T cells and B cells and generates immunosuppression from T cell depletion.

CD20 fulfills the basic criteria described above for selection of an appropriate target antigen for therapy of a B cell malignant condition. Treatment of patients with low grade or follicular B cell lymphoma using chimeric CD20 mAb induces partial or complete responses in many patients (McLaughlin et al, *Blood* 88:90a (abstract, suppl. 1) (1996);

Maloney et al, *Blood* 90: 2188-95 (1997)). However, tumor relapse commonly occurs within six months to one year. Therefore, further improvements in serotherapy are needed to induce more durable responses in low grade B cell lymphoma, and to allow effective treatment of high grade lymphoma and other B cell diseases.

One approach to improving CD20 serotherapy has been to target radioisotopes to B cell lymphomas using mAbs specific for CD20. While the effectiveness of therapy is increased, associated toxicity from the long in vivo half-life of the radioactive antibody increased also, sometimes requiring that the patient undergo stem cell rescue (Press et al., *N. Eng. J. Med.* 329: 1219-1224, 1993; Kaminski et al., *N. Eng. J. Med.* 329: 459-65 (1993)). MAbs to CD20 have been cleaved with proteases to yield F(ab')$_2$ or Fab fragments prior to attachment of the radioisotope. This improves penetration of the radioisotope conjugate into the tumor, and shortens the in vivo half-life, thus reducing the toxicity to normal tissues. However, the advantages of effector functions, including complement fixation and ADCC, that are provided by the Fc region of the CD20 mAb are lost. Therefore, for improved delivery of radioisotopes, a strategy is needed to make a CD20 mAb derivative that retains Fc-dependent effector functions but which is smaller in size, thereby increasing tumor penetration and shortening mAb half-life.

CD20 was the first human B cell lineage-specific surface molecule identified by a monoclonal antibody, but the function of CD20 in B cell biology is still incompletely understood. CD20 is a non-glycosylated, hydrophobic 35 kDa phosphoprotein that has both amino and carboxy ends in the cytoplasm (Einfeld et al, *EMBO J.* 7:711-17 (1988)). Natural ligands for CD20 have not been identified. CD20 is expressed by all normal mature B cells, but is not expressed by precursor B cells.

CD20 mAbs deliver signals to normal B cells that affect viability and growth (Clark et al., *Proc. Natl. Acad. Sci. USA* 83:4494-98 (1986)). Recent data has shown that extensive cross-linking of CD20 can induce apoptosis of B lymphoma cell lines (Shan et al., *Blood* 91:1644-52 (1998)). Cross-linking of CD20 on the cell surface increases the magnitude and kinetics of signal transduction, which was detected by measuring phosphorylation of cellular substrates on tyrosine residues (Deans et al., *J. Immunol.* 146:846-53 (1993)). Importantly, apoptosis of Ramos B lymphoma cells was also be induced by cross-linking of CD20 mAbs by addition of Fc-receptor positive cells (Shan et al., *Blood* 91: 1644-52 (1998)). Therefore, in addition to cellular depletion by complement and ADCC mechanisms, Fc-receptor binding by CD20 mAbs in vivo could promote apoptosis of malignant B cells by CD20 cross-linking. This theory is consistent with experiments showing that effectiveness of CD20 therapy of human lymphoma in a SCID mouse model was dependent upon Fc-receptor binding by the CD20 mAb (Funakoshi et al., *J. Immunotherapy* 19:93-101 (1996)).

The CD20 polypeptide contains four transmembrane domains (Einfeld et al., *EMBO J.* 7: 711-17, (1988); Stamenkovic et al., *J. Exp. Med.* 167:1975-80 (1988); Tedder et. al., *J. Immunol.* 141:4388-4394 (1988)). The multiple membrane spanning domains prevent CD20 internalization after antibody binding. This property of CD20 was recognized as an important feature for effective therapy of B cell malignancies when a murine CD20 mAb, 1F5, was injected into patients with B cell lymphoma, resulting in significant depletion of malignant cells and partial clinical responses (Press et al., *Blood* 69: 584-91 (1987)).

Because normal mature B cells also express CD20, normal B cells are depleted during CD20 antibody therapy (Reff, M. E. et al, *Blood* 83: 435-445, 1994). However, after treatment is completed, normal B cells are regenerated from CD20 negative B cell precursors; therefore, patients treated with anti-CD20 therapy do not experience significant immunosuppression. Depletion of normal B cells may be beneficial in diseases that involve inappropriate production of autoantibodies or other diseases where B cells may play a role. A chimeric mAb specific for CD20, consisting of heavy and light chain variable regions of mouse origin fused to human IgG1 heavy chain and human kappa light chain constant regions, retained binding to CD20 and the ability to mediate ADCC and to fix complement (Liu et al., *J. Immunol.* 139: 3521-26 (1987); Robinson et al., U.S. Pat. No. 5,500,362). This work led to development of a chimeric CD20 mAb, Rituximab™, currently approved by the U.S. Food and Drug Administration for approval for therapy of B cell lymphomas. While clinical responses are frequently observed after treatment with Rituximab™, patients often relapse after about 6-12 months.

High doses of Rituximab™ are required for intravenous injection because the molecule is large, approximately 150 kDa, and diffusion is limited into the lymphoid tissues where many tumor cells reside. The mechanism of anti-tumor activity of Rituximab™ is thought to be a combination of several activities, including ADCC, fixation of complement, and triggering of signals in malignant B cells that promote apoptosis. The large size of Rituximab™ prevents optimal diffusion of the molecule into lymphoid tissues that contain malignant B cells, thereby limiting these anti-tumor activities. As discussed above, cleavage of CD20 mAbs with proteases into Fab or F(ab')$_2$ fragments makes them smaller and allows better penetration into lymphoid tissues, but the effector functions important for anti-tumor activity are lost. While CD20 mAb fragments may be more effective than intact antibody for delivery of radioisotopes, it would be desirable to construct a CD20 mAb derivative that retains the effector functions of the Fc portion, but is smaller in size, facilitating better tumor penetration and resulting in a shorter half-life.

CD20 is expressed by malignant cells of B cell origin, including B cell lymphoma and chronic lymphocytic leukemia (CLL). CD20 is not expressed by malignancies of pre-B cells, such as acute lymphoblastic leukemia. CD20 is therefore a good target for therapy of B cell lymphoma, CLL, and other diseases in which B cells are involved in the disease activity. Other B cell disorders include autoimmune diseases in which autoantibodies are produced during the differentiation of B cells into plasma cells. Examples of B cell disorders include autoimmune thyroid disease, including Graves' disease and Hashimoto's thyroiditis, rheumatoid arthritis, systemic lupus erythematosus (SLE), Sjogrens syndrome, immune thrombocytopenic purpura (ITP), multiple sclerosis (MS), myasthenia gravis (MG), psoriasis, scleroderma, and inflammatory bowel disease, including Crohn's disease and ulcerative colitis.

From the foregoing, a clear need is apparent for improved compositions and methods to treat malignant conditions and B cell disorders. The compositions and methods of the present invention overcome the limitations of the prior art by providing a binding domain-immunoglobulin fusion protein comprising a binding domain polypeptide that is fused to an immunoglobulin hinge region polypeptide, which is fused to an immunoglobulin heavy chain CH2 constant region polypeptide fused to an immunoglobulin heavy chain CH3 constant region polypeptide, wherein the binding domain-immunoglobulin fusion protein is capable of mediating ADCC or complement fixation. Furthermore, the compositions and methods offer other related advantages.

SUMMARY OF THE INVENTION

It is an aspect of the present invention to provide a binding domain-immunoglobulin fusion protein, comprising (a) a binding domain polypeptide that is fused to an immunoglobulin hinge region polypeptide, wherein said hinge region polypeptide is selected from the group consisting of (i) a mutated hinge region polypeptide that contains no cysteine residues and that is derived from a wild-type immunoglobulin hinge region polypeptide having one or more cysteine residues, (ii) a mutated hinge region polypeptide that contains one cysteine residue and that is derived from a wild-type immunoglobulin hinge region polypeptide having two or more cysteine residues, (iii) a wild-type human IgA hinge region polypeptide, (iv) a mutated human IgA hinge region polypeptide that contains no cysteine residues and that is derived from a wild-type human IgA region polypeptide, and (v) a mutated human IgA hinge region polypeptide that contains one cysteine residue and that is derived from a wild-type human IgA region polypeptide; (b) an immunoglobulin heavy chain CH2 constant region polypeptide that is fused to the hinge region polypeptide; and (c) an immunoglobulin heavy chain CH3 constant region polypeptide that is fused to the CH2 constant region polypeptide, wherein: (1) the binding domain-immunoglobulin fusion protein is capable of at least one immunological activity selected from the group consisting of antibody dependent cell-mediated cytotoxicity and complement fixation, and (2) the binding domain polypeptide is capable of specifically binding to an antigen. In one embodiment the immunoglobulin hinge region polypeptide is a mutated hinge region polypeptide and exhibits a reduced ability to dimerize, relative to a wild-type human immunoglobulin G hinge region polypeptide. In another embodiment the binding domain polypeptide comprises at least one immunoglobulin variable region polypeptide that is an immunoglobulin light chain variable region polypeptide or an immunoglobulin heavy chain variable region polypeptide. In a further embodiment the immunoglobulin variable region polypeptide is derived from a human immunoglobulin.

In another embodiment the binding domain Fv-immunoglobulin fusion protein binding domain polypeptide comprises (a) at least one immunoglobulin light chain variable region polypeptide; (b) at least one immunoglobulin heavy chain variable region polypeptide; and (c) at least one linker peptide that is fused to the polypeptide of (a) and to the polypeptide of (b). In a further embodiment the immunoglobulin light chain variable region and heavy chain variable region polypeptides are derived from human immunoglobulins.

In another embodiment at least one of the immunoglobulin heavy chain CH2 constant region polypeptide and the immunoglobulin heavy chain CH3 constant region polypeptide is derived from a human immunoglobulin heavy chain. In another embodiment the immunoglobulin heavy chain constant region CH2 and CH3 polypeptides are of an isotype selected from human IgG and human IgA. In another embodiment the antigen is selected from the group consisting of CD19, CD20, CD37, CD40 and L6. In certain further embodiments of the above described fusion protein, the linker polypeptide comprises at least one polypeptide having as an amino acid sequence Gly-Gly-Gly-Gly-Ser, and in certain other embodiments the linker polypeptide comprises at least three repeats of a polypeptide having as an amino acid sequence Gly-Gly-Gly-Gly-Ser. In certain embodiments the immunoglobulin hinge region polypeptide comprises a human IgA hinge region polypeptide. In certain embodiments the binding domain polypeptide comprises a CD154 extracellular domain. In certain embodiments the binding domain polypeptide comprises a CD154 extracellular domain and at least one immunoglobulin variable region polypeptide.

In other embodiments the invention provides an isolated polynucleotide encoding any of the above described binding domain-immunoglobulin fusion proteins, and in related embodiments the invention provides a recombinant expression construct comprising such a polynucleotide, and in certain further embodiments the invention provides a host cell transformed or transfected with such a recombinant expression construct. In another embodiment the invention provides a method of producing a binding domain-immunoglobulin fusion protein, comprising the steps of (a) culturing the host cell as just described, under conditions that permit expression of the binding domain-immunoglobulin fusion protein; and (b) isolating the binding domain-immunoglobulin fusion protein from the host cell culture.

The present invention also provides in certain embodiments a pharmaceutical composition comprising a binding domain-immunoglobulin fusion protein as described above, in combination with a physiologically acceptable carrier. In another embodiment there is provided a method of treating a subject having or suspected of having a malignant condition or a B-cell disorder, comprising administering to a patient a therapeutically effective amount of an above described binding domain-immunoglobulin fusion protein. In certain further embodiments the malignant condition or B-cell disorder is a B-cell lymphoma or a disease characterized by autoantibody production, and in certain other further embodiments the malignant condition or B-cell disorder is rheumatoid arthritis, myasthenia gravis, Grave's disease, type I diabetes mellitus, multiple sclerosis or an autoimmune disease.

These and other aspects of the present invention will become apparent upon reference to the following detailed description and attached drawings. All references disclosed herein are hereby incorporated by reference in their entireties as if each was incorporated individually.

BRIEF DESCRIPTION OF THE DRAWINGS

FIGS. 1A-1B show DNA and deduced amino acid sequences (SEQ ID NO:15) of 2H7scFv-Ig, a binding domain-immunoglobulin fusion protein capable of specifically binding CD20.

FIG. 4 shows complement fixation (FIG. 4A) and mediation of antibody-dependent cellular cytotoxicity (ADCC, FIG. 4B)) by 2H7scFv-Ig.

FIG. 5 shows the effect of simultaneous ligation of CD20 and CD40 on growth of normal B cells.

FIGS. 6A-6B show the effect of simultaneous ligation of CD20 and CD40 on CD95 expression (6A) and induction of apoptosis in a B lymphoblastoid cell line (6B).

FIG. 7 shows DNA and deduced amino acid sequences of 2H7scFv-CD 154L2 (FIG. 7A-7B, SEQ ID NOS: 21 and 33) and 2H7scFv-CD154 S4 (FIG. 7C-7D, SEQ ID NOS: 22 and 34) binding domain-immunoglobulin fusion proteins capable of specifically binding CD20 and CD40.

DETAILED DESCRIPTION OF THE INVENTION

Figure 2:
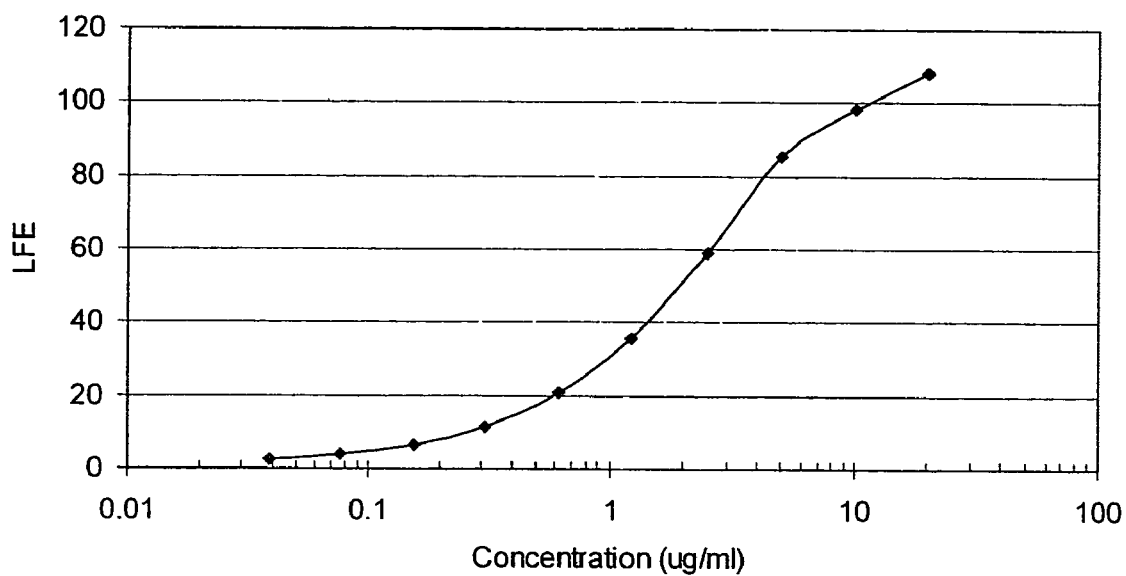
FIG. 2 shows production levels of 2H7 scFv-Ig by transfected, stable CHO lines and generation of a standard curve by binding of purified 2H7 scFv-Ig to CHO cells expressing CD20.

The present invention is directed to binding domain-immunoglobulin fusion proteins and to related compositions and methods, which will be useful in immunotherapeutic and immunodiagnostic applications, and which offer certain advantages over antigen-specific polypeptides of the prior art. The fusion proteins of the present invention are preferably single polypeptide chains that comprise, in pertinent part, the following fused domains: a binding domain polypeptide, an immunoglobulin hinge region polypeptide, an immunoglobulin heavy chain CH2 constant region polypeptide, and an immunoglobulin heavy chain CH3 constant region polypeptide. In particularly preferred embodiments, the polypeptide domains of which the binding domain-immunoglobulin fusion protein is comprised are, or are derived from, polypeptides that are the products of human gene sequences, but the invention need not be so limited and may in fact relate to binding domain-immunoglobulin fusion proteins as provided herein that are derived from any natural or artificial source, including genetically engineered and/or mutated polypeptides.

The present invention relates in part to the surprising observation that the binding domain-immunoglobulin fusion proteins described herein are capable of immunological activity. More specifically, these proteins retain the ability to participate in well known immunological effector activities including antibody dependent cell mediated cytotoxicity (ADCC, e.g., subsequent to antigen binding on a cell surface, engagement and induction of cytotoxic effector cells bearing appropriate Fc receptors, such as natural killer (NK) cells bearing FcRγIII, under appropriate conditions) and/or complement fixation in complement dependent cytotoxicity (CDC, e.g., subsequent to antigen binding on a cell surface, recruitment and activation of cytolytic proteins that are components of the blood complement cascade ), despite having structures that would not be expected to be capable of promoting such effector activities. As described in greater detail below, ADCC and CDC are unexpected functions for monomeric proteins comprising immunoglobulin heavy chain regions, which are favored by the structures selected for the subject fusion proteins, and particularly by the selection of hinge region polypeptides that are compromised in their ability to form interchain, homodimeric disulfide bonds.

Another advantage afforded by the present invention is a binding domain-immunoglobulin fusion polypeptide that can be produced in substantial quantities that are typically greater than those routinely attained with single-chain antibody constructs of the prior art. In preferred embodiments, the binding domain-immunoglobulin fusion polypeptides of the present invention are recombinantly expressed in mammalian expression systems, which offer the advantage of providing polypeptides that are stable in vivo (e.g., under physiological conditions). According to non-limiting theory, such stability may derive in part from posttranslational modifications, and specifically glycosylation, of the fusion proteins. Production of the present binding domain-immunoglobulin fusion proteins via recombinant mammalian expression has been attained in static cell cultures at a level of greater than 50 mg protein per liter culture supernatant and has been routinely observed in such cultures at 10-50 mg/l, such that preferably at least 10-50 mg/l may be produced under static culture conditions; also contemplated are enhanced production of the fusion proteins using art-accepted scale-up methodologies such as "fed batch" (i.e., non-static) production, where yields of at least 5-500 mg/l, and in some instances at least 0.5-1 gm/l, depending on the particular protein product, are obtained.

A binding domain polypeptide according to the present invention may be any polypeptide that possesses the ability to specifically recognize and bind to a cognate biological molecule or complex of more than one molecule or assembly or aggregate, whether stable or transient, of such a molecule, which includes a protein, polypeptide, peptide, amino acid, or derivative thereof; a lipid, fatty acid or the like, or derivative thereof; a carbohydrate, saccharide or the like or derivative thereof, a nucleic acid, nucleotide, nucleoside, purine, pyrimidine or related molecule, or derivative thereof, or the like; or any combination thereof such as, for example, a glycoprotein, a glycopeptide, a glycolipid, a lipoprotein, a proteolipid; or any other biological molecule that may be present in a biological sample. Biological samples may be provided by obtaining a blood sample, biopsy specimen, tissue explant, organ culture, biological fluid or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines and the like. In certain preferred embodiments of the invention, the subject or biological source may be suspected of having or being at risk for having a malignant condition or a B-cell disorder as provided herein, which in certain further preferred embodiments may be an autoimmune disease, and in certain other preferred embodiments of the invention the subject or biological source may be known to be free of a risk or presence of such disease.

A binding domain polypeptide may therefore be any naturally occurring or recombinantly produced binding partner for a cognate biological molecule as provided herein that is a target structure of interest, herein referred to as an "antigen" but intended according to the present disclosure to encompass any target biological molecule to which it is desirable to have the subject invention fusion protein specifically bind. Binding domain-immunoglobulin fusion proteins are defined to be "immunospecific" or capable of specifically binding if they bind a desired target molecule such as an antigen as provided herein, with a $K_a$ of greater than or equal to about $10^4$ $M^{-1}$, preferably of greater than or equal to about $10^5$ $M^{-1}$, more preferably of greater than or equal to about $10^6$ $M^{-1}$ and still more preferably of greater than or equal to about $10^7$ $M^{-1}$. Affinities of binding domain-immunoglobulin fusion proteins according to the present invention can be readily determined using conventional techniques, for example those described by Scatchard et al., *Ann. N.Y. Acad. Sci.* 51:660 (1949). Such determination of fusion protein binding to target antigens of interest can also be performed using any of a number of known methods for identifying and obtaining proteins that specifically interact with other proteins or polypeptides, for example, a yeast two-hybrid screening system such as that described in U.S. Pat. No. 5,283,173 and U.S. Pat. No. 5,468,614, or the equivalent.

Preferred embodiments of the subject invention binding domain-immunoglobulin fusion protein comprise binding domains that include at least one immunoglobulin variable region polypeptide, such as all or a portion or fragment of a heavy chain or a light chain V-region, provided it is capable of specifically binding an antigen or other desired target structure of interest as described herein. In other preferred embodiments the binding domain comprises a single chain immunoglobulin-derived Fv product, which may include all or a portion of at least one immunoglobulin light chain V-region and all or a portion of at least one immunoglobulin heavy chain V-region, and which further comprises a linker fused to the V-regions; preparation and testing such constructs are described in greater detail herein and are well known in the art. Other binding domain polypeptides may comprise any protein or portion thereof that retains the ability to specifically bind an antigen as provided herein, including non-immunoglobulins. Accordingly the invention contemplates fusion proteins comprising binding domain polypeptides that are derived from polypeptide ligands such as hormones, cytokines, chemokines, and the like; cell surface or soluble receptors for such polypeptide ligands; lectins; intercellular adhesion receptors such as specific leukocyte integrins, selectins, immunoglobulin gene superfamily members, intercellular adhesion molecules (ICAM-1, -2, -3) and the like; histocompatibility antigens; etc.

Examples of cell surface receptors that may provide a binding domain polypeptide, and that may also be selected as the target molecule or antigen to which a binding domain-Ig fusion protein of the present invention desirably binds, include the following, or the like: HER1 (e.g., GenBank Accession Nos. U48722, SEG_HEGFREXS, KO3193), HER2 (Yoshino et al., 1994 *J. Immunol.* 152:2393; Disis et al., 1994 *Canc. Res.* 54:16; see also, e.g., GenBank Acc. Nos. X03363, M17730, SEG_HUMHER20), HER3 (e.g., GenBank Acc. Nos. U29339, M34309), HER4 (Plowman et al., 1993 *Nature* 366:473; see also e.g., GenBank Acc. Nos. L07868, T64105), epidermal growth factor receptor (EGFR) (e.g., GenBank Acc. Nos. U48722, SEG_HEGFREXS, K03193), vascular endothelial cell growth factor(e.g., GenBank No. M32977), vascular endothelial cell growth factor receptor (e.g., GenBank Acc. Nos. AF022375, 1680143, U48801, X62568), insulin-like growth factor-I (e.g., GenBank Acc. Nos. X00173, X56774, X56773, X06043, see also European Patent No. GB 2241703), insulin-like growth factor-II (e.g., GenBank Acc. Nos. X03562, X00910, SEG_HUMGFIA, SEG_HUMGFI2, M17863, M17862), transferrin receptor (Trowbridge and Omary, 1981 *Proc. Nat. Acad. USA* 78:3039; see also e.g., GenBank Acc. Nos. X01060, M11507), estrogen receptor (e.g., GenBank Acc. Nos. M38651, X03635, X99101, U47678, M12674), progesterone receptor (e.g., GenBank Acc. Nos. X51730, X69068, M15716), follicle stimulating hormone receptor (FSH-R) (e.g., GenBank Acc. Nos. Z34260, M65085), retinoic acid receptor (e.g., GenBank Acc. Nos. L12060, M60909, X77664, X57280, X07282, X06538), MUC-1 (Barnes et al., 1989 *Proc. Nat. Acad. Sci. USA* 86:7159; see also e.g., GenBank Acc. Nos. SEG_MUSMUCIO, M65132, M64928) NY-ESO-1 (e.g., GenBank Acc. Nos. AJ003149, U87459), NA 17-A (e.g., European Patent No. WO 96/40039), Melan-A/MART-1 (Kawakami et al., 1994 *Proc. Nat. Acad. Sci. USA* 91:3515; see also e.g., GenBank Acc. Nos. U06654, U06452), tyrosinase (Topalian et al., 1994 *Proc. Nat. Acad. Sci. USA* 91:9461; see also e.g., GenBank Acc. Nos. M26729, SEG_HUMTYR0, see also Weber et al., *J. Clin. Invest* (1998) 102:1258), Gp-100 (Kawakami et al., 1994 *Proc. Nat. Acad. Sci. USA* 91:3515; see also e.g., GenBank Acc. No. S73003, see also European Patent No. EP 668350; Adema et al., 1994 *J. Biol. Chem.* 269:20126), MAGE (van den Bruggen et al., 1991 *Science* 254:1643; see also e.g, GenBank Acc. Nos. U93163, AF064589, U66083, D32077, D32076, D32075, U10694, U10693, U10691, U10690, U10689, U10688, U10687, U10686, U10685, L18877, U10340, U10339, L18920, U03735, M77481), BAGE (e.g., GenBank Acc. No. U19180, see also U.S. Pat. Nos. 5,683,886 and 5,571,711), GAGE (e.g., GenBank Acc. Nos. AF055475, AF055474, AF055473, U19147, U19146, U19145, U19144, U19143, U19142), any of the CTA class of receptors including in particular HOM-MEL-40 antigen encoded by the SSX2 gene (e.g., GenBank Acc. Nos. X86175, U90842, U90841, X86174), carcinoembyonic antigen (CEA, Gold and Freedman, 1985 *J. Exp. Med.* 121:439; see also e.g., GenBank Acc. Nos. SEG_HUMCEA, M59710, M59255, M29540), and PyLT (e.g., GenBank Acc. Nos. J02289, J02038).

Additional cell surface receptors that may be sources of binding domain polypeptides or that may be cognate antigens include the following, or the like: CD2 (e.g., GenBank Acc. Nos. Y00023, SEG_HUMCD2, M16336, M16445, SEG_MUSCD2, M14362), 4-1BB (CDw137, Kwon et al., 1989 *Proc. Nat. Acad. Sci. USA* 86:1963, 4-1BB ligand (Goodwin et al., 1993 *Eur. J. Immunol.* 23:2361; Melero et al., 1998 *Eur. J Immunol.* 3:116), CD5 (e.g., GenBank Acc. Nos. X78985, X89405), CD10 (e.g., GenBank Acc. Nos. M81591, X76732) CD27 (e.g., GenBank Acc. Nos. M63928, L24495, L08096), CD28 (June et al., 1990 *Immunol. Today* 11:211; see also, e.g., GenBank Acc. Nos. J02988, SEG_HUMCD28, M34563), CTLA-4 (e.g., GenBank Acc. Nos. L15006, X05719, SEG_HUMIGCTL), CD40 (e.g., GenBank Acc. Nos. M83312, SEG_MUSC040A0, Y10507, X67878, X96710, U15637, L07414), interferon-γ (IFN-γ; see, e.g., Farrar et al. 1993 *Ann. Rev. Immunol.* 11:571 and references cited therein, Gray et al. 1982 *Nature* 295:503, Rinderknecht et al. 1984 *J. Biol. Chem.* 259:6790, DeGrado et al. 1982 *Nature* 300:379), interleukin-4 (IL-4; see, e.g., 53rd *Forum in Immunology*, 1993 *Research in Immunol.* 144:553-643; Banchereau et al., 1994 in *The Cytokine Handbook*, 2nd ed., A. Thomson, ed., Academic Press, NY, p. 99; Keegan et al., 1994 *J Leukocyt. Biol.* 55:272, and references cited therein), interleukin-17 (IL-17) (e.g., GenBank Acc. Nos. U32659, U43088) and interleukin-17 receptor (IL-17R) (e.g., GenBank Acc. Nos. U31993, U58917). Notwithstanding the foregoing, the present invention expressly does not encompass any immunoglobulin fusion protein that is disclosed in U.S. Pat. No. 5,807,734, U.S. Pat. No. 5,795,572 or U.S. Pat. No. 5,807,734.

Additional cell surface receptors that may be sources of binding domain polypeptides or that may be cognate antigens include the following, or the like: CD59 (e.g., GenBank Acc. Nos. SEG_HUMCD590, M95708, M34671), CD48 (e.g., GenBank Acc. Nos. M59904), CD58/LFA-3 (e.g., GenBank Acc. No. A25933, Y00636, E12817; see also JP 1997075090-A), CD72 (e.g., GenBank Acc. Nos. AA311036, S40777, L35772), CD70 (e.g., GenBank Acc. Nos. Y13636, S69339), CD80/B7.1 (Freeman et al., 1989 *J. Immunol.* 43:2714; Freeman et al., 1991 *J. Exp. Med.* 174:625; see also e.g., GenBank Acc. Nos. U33208, I683379), CD86/B7.2 (Freeman et al., 1993 *J. Exp. Med.* 178:2185, Boriello et al., 1995 *J. Immunol.* 155:5490; see also, e.g., GenBank Acc. Nos. AF099105, SEG_MMB72G, U39466, U04343, SEG_HSB725, L25606, L25259), CD40 ligand (e.g., GenBank Acc. Nos. SEG_HUMCD40L, X67878, X65453, L07414), IL-17 (e.g., GenBank Acc. Nos. U32659, U43088), CD43 (e.g., GenBank Acc. Nos. X52075, J04536) and VLA-4 ($\alpha_4\beta_7$) (e.g., GenBank Acc. Nos. L12002, X16983, L20788, U97031, L24913, M68892, M95632). The following cell surface receptors are typically associated with B cells: CD19 (e.g., GenBank Acc. Nos. SEG_HUMCD19WO, M84371, SEG_MUSCD19W, M62542), CD20 (e.g., GenBank Acc. Nos. SEG_HUMCD20, M62541), CD22 (e.g., GenBank Acc. Nos. I680629, Y10210, X59350, U62631, X52782, L16928), CD30 ligand (e.g., GenBank Acc. Nos. L09753, M83554), CD37 (e.g., GenBank Acc. Nos. SEG_MMCD37X, X14046, X53517), CD106 (VCAM-1) (e.g., GenBank Acc. Nos. X53051, X67783, SEG_MMVCAM1C, see also U.S. Pat. No. 5,596,090), CD54 (ICAM-1) (e.g., GenBank Acc. Nos. X84737, S82847, X06990, J03132, SEG_MUSICAM0), interleukin-12 (see, e.g., Reiter et al, 1993 *Crit. Rev. Immunol.* 13:1, and references cited therein). Accessory cell agents may also include any of the following cell surface receptors typically associated with dendritic cells: CD83 (e.g., GenBank Acc. Nos. AF001036, AL021918), DEC-205 (e.g., GenBank Acc. Nos. AF011333, U19271).

An immunoglobulin hinge region polypeptide, as discussed above, includes any hinge peptide or polypeptide that occurs naturally, as an artificial peptide or as the result of genetic engineering and that is situated in an immunoglobulin heavy chain polypeptide between the amino acid residues responsible for forming intrachain immunoglobulin-domain disulfide bonds in CH1 and CH2 regions; hinge region polypeptides for use in the present invention may also include a mutated hinge region polypeptide. Accordingly, an immunoglobulin hinge region polypeptide may be derived from, or may be a portion or fragment of (i.e., one or more amino acids in peptide linkage, typically 5-65 amino acids, preferably 10-50, more preferably 15-35, still more preferably 18-32, still more preferably 20-30, still more preferably 21, 22, 23, 24, 25, 26, 27, 28 or 29 amino acids) an immunoglobulin polypeptide chain region classically regarded as having hinge function, as described above, but a hinge region polypeptide for use in the instant invention need not be so restricted and may include amino acids situated (according to structural criteria for assigning a particular residue to a particular domain that may vary, as known in the art) in an adjoining immunoglobulin domain such as a CH1 domain or a CH2 domain, or in the case of certain artificially engineered immunoglobulin constructs, an immunoglobulin variable region domain.

Wild-type immunoglobulin hinge region polypeptides include any naturally occurring hinge region that is located between the constant region domains, CH1 and CH2, of an immunoglobulin. The wild-type immunoglobulin hinge region polypeptide is preferably a human immunoglobulin hinge region polypeptide, preferably comprising a hinge region from a human IgG immunoglobulin, and more preferably, a hinge region polypeptide from a human IgG1 isotype. As is known to the art, despite the tremendous overall diversity in immunoglobulin amino acid sequences, immunoglobulin primary structure exhibits a high degree of sequence conservation in particular portions of immunoglobulin polypeptide chains, notably with regard to the occurrence of cysteine residues which, by virtue of their sulfyhydryl groups, offer the potential for disulfide bond formation with other available sulfydryl groups. Accordingly, in the context of the present invention wild-type immunoglobulin hinge region polypeptides may be regarded as those that feature one or more highly conserved (e.g., prevalent in a population in a statistically significant manner) cysteine residues, and in certain preferred embodiments a mutated hinge region polypeptide may be selected that contains zero or one cysteine residue and that is derived from such a wild-type hinge region.

A mutated immunoglobulin hinge region polypeptide may comprise a hinge region that has its origin in an immunoglobulin of a species, of an immunoglobulin isotype or class, or of an immunoglobulin subclass that is different from that of the CH2 and CH3 domains. For instance, in certain embodiments of the invention, the binding domain-immunoglobulin fusion protein may comprise a binding domain polypeptide that is fused to an immunoglobulin hinge region polypeptide comprising a wild-type human IgA hinge region polypeptide, or a mutated human IgA hinge region polypeptide that contains zero or only one cysteine residues, as described herein. Such a hinge region polypeptide may be fused to an immunoglobulin heavy chain CH2 region polypeptide from a different Ig isotype or class, for example an IgG subclass, which in certain preferred embodiments will be the IgG1 subclass.

For example, and as described in greater detail below, in certain embodiments of the present invention an immunoglobulin hinge region polypeptide is selected which is derived from a wild-type human IgA hinge region that naturally comprises three cysteines, where the selected hinge region polypeptide is truncated relative to the complete hinge region such that only one of the cysteine residues remains (e.g., SEQ ID NO:36). Similarly, in certain other embodiments of the invention, the binding domain-immunoglobulin fusion protein comprises a binding domain polypeptide that is fused to an immunoglobulin hinge region polypeptide comprising a mutated hinge region polypeptide in which the number of cysteine residues is reduced by amino acid substitution or deletion. A mutated hinge region polypeptide may thus be derived from a wild-type immunoglobulin hinge region that contains one or more cysteine residues. In certain embodiments, a mutated hinge region polypeptide may contain zero or only one cysteine residue, wherein the mutated hinge region polypeptide is derived from a wild type immunoglobulin hinge region that contains, respectively, one or more or two or more cysteine residues. In the mutated hinge region polypeptide, the cysteine residues of the wild-type immunoglobulin hinge region are preferably substituted with amino acids that are incapable of forming a disulfide bond. In one embodiment of the invention, the mutated hinge region polypeptide is derived from a human IgG wild-type hinge region polypeptide, which may include any of the four human IgG isotype subclasses, IgG1, IgG2, IgG3 or IgG4. In certain preferred embodiments, the mutated hinge region polypeptide is derived from a human IgG1 wild-type hinge region polypeptide. By way of example, a mutated hinge region polypeptide derived from a human IgG1 wild-type hinge region polypeptide may comprise mutations at two of the three cysteine residues in the wild-type immunoglobulin hinge region, or mutations at all three cysteine residues.

The cysteine residues that are present in a wild-type immunoglobulin hinge region and that are removed by mutagenesis according to particularly preferred embodiments of the present invention include cysteine residues that form, or that are capable of forming, interchain disulfide bonds. Without wishing to be bound by theory, the present invention contemplates that mutation of such hinge region cysteine residues, which are believed to be involved in formation of interchain disulfide bridges, reduces the ability of the subject invention binding domain-immunoglobulin fusion protein to dimerize (or form higher oligomers) via interchain disulfide bond formation, while surprisingly not ablating the ability of the fusion protein to promote antibody dependent cell-mediated cytotoxicity (ADCC) or to fix complement. In particular, the Fc receptors (FcR) which mediate ADCC (e.g., FcRIII, CD16) exhibit low affinity for immunoglobulin Fc domains, suggesting that functional binding of Fc to FcR requires avidity stabilization of the Fc-FcR complex by virtue of the dimeric structure of heavy chains in a conventional antibody, and/or FcR aggregation and cross-linking by a conventional Ab Fc structure. (Sonderman et al., 2000 *Nature* 406:267; Radaev et al., 2001 *J. Biol. Chem.* 276:16469; Radaev et al., 2001 *J. Biol. Chem.* 276:16478; Koolwijk et al., 1989 *J. Immunol.* 143:1656; Kato et al., 2000 *Immunol. Today* 21:310.) Hence, the binding domain-immunoglobulin fusion proteins of the present invention provide the advantages associated with single-chain immunoglobulin fusion proteins while also unexpectedly retaining immunological activity. Similarly, the ability to fix complement is typically associated with immunoglobulins that are dimeric with respect to heavy chain constant regions such as those that comprise Fc, while the binding domain-immunoglobulin fusion proteins of the present invention exhibit the unexpected ability to fix complement.

As noted above, binding domain-immunoglobulin fusion proteins are believed, according to non-limiting theory, to be compromised in their ability to dimerize, and further according to theory, this property is a consequence of a reduction in the number of cysteine residues that are present in the immunoglobulin hinge region polypeptide selected for inclusion in the construction of the fusion protein. Determination of the relative ability of a polypeptide to dimerize is well within the knowledge of the relevant art, where any of a number of established methodologies may be applied to detect protein dimerization (see, e.g., Scopes, *Protein Purification: Principles and Practice,* 1987 Springer-Verlag, New York). For example, biochemical separation techniques for resolving proteins on the basis of molecular size (e.g., gel electrophoresis, gel filtration chromatography, analytical ultracentrifugation, etc.), and/or comparison of protein physicochemical properties before and after introduction of sulfhydryl-active (e.g., iodoacetamide, N-ethylmaleimide) or disulfide-reducing (e.g., 2-mercaptoethanol, dithiothreitol) agents, or other equivalent methodologies, may all be employed for determining a degree of polypeptide dimerization or oligomerization, and for determining possible contribution of disulfide bonds to such potential quaternary structure. In certain embodiments, the invention relates to a binding domain-immunoglobulin fusion protein that exhibits a reduced (i.e., in a statistically significant manner relative to an appropriate IgG-derived control) ability to dimerize, relative to a wild-type human immunoglobulin G hinge region polypeptide as provided herein. Accordingly, those familiar with the art will be able readily to determine whether a particular fusion protein displays such reduced ability to dimerize.

Compositions and methods for preparation of immunoglobulin fusion proteins are well known in the art, as described for example, in U.S. Pat. No. 5,892,019, which discloses recombinant antibodies that are the products of a single encoding polynucleotide but which are not binding domain-immunoglobulin fusion proteins according to the present invention.

Figure 11:
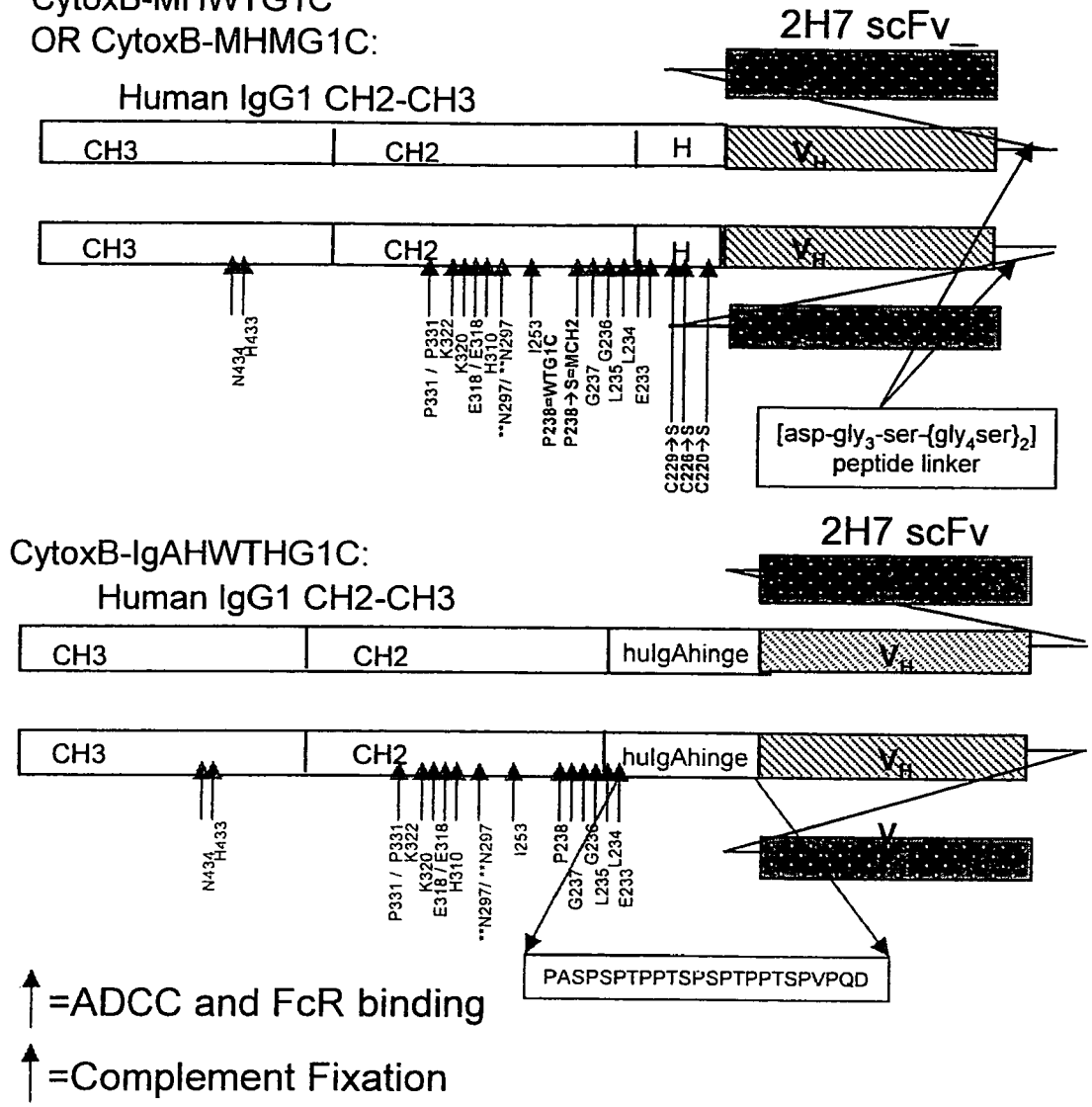
FIG. 11 depicts schematic representations of the structures of 2H7ScFv-Ig fusion proteins (SEQ ID NOS:17, 16, AND 18) referred to as CytoxB or CytoxB derivatives: CytoxB-MHWTG1C (2H7 ScFv, mutant hinge, wild-type human IgG1 Fc domain), CytoxB-MHMG1C (2H7 ScFv, mutant hinge, mutated human IgG1 Fc domain) and CytoxB-IgAHWTHG1C (2H7 ScFv, human IgA-derived hinge, wild-type human IgG1 Fc domain) respectively. Arrows indicate position numbers of amino acid residues believed to contribute to FcR binding and ADCC activity (heavy arrows), and to complement fixation (light arrows). Note absence of interchain disulfide bonds.

For an immunoglobulin fusion protein of the invention which is intended for use in humans, the constant regions will typically be of human sequence origin, to minimize a potential anti-human immune response and to provide appropriate effector functions. Manipulation of sequences encoding antibody constant regions is described in the PCT publication of Morrison and Oi, WO 89/07142. In particularly preferred embodiments, the CH1 domain is deleted and the carboxyl end of the binding domain, or where the binding domain comprises two immunoglobulin variable region polypeptides, the second (i.e., more proximal to the C-terminus) variable region is joined to the amino terminus of CH2 through the hinge region. A schematic diagram depicting the structures of two exemplary binding domain-immunoglobulin fusion proteins is shown in FIG. 11, where it should be noted that in particularly preferred embodiments no interchain disulfide bonds are present, and in other embodiments a restricted number of interchain disulfide bonds may be present relative to the number of such bonds that would be present if wild-type hinge region polypeptides were instead present, and that in other embodiments the fusion protein comprises a mutated hinge region polypeptide that exhibits a reduced ability to dimerize, relative to a wild-type human IgG hinge region polypeptide. Thus, the isolated polynucleotide molecule codes for a single chain immunoglobulin fusion protein having a binding domain that provides specific binding affinity for a selected antigen.

As noted above, in certain embodiments the binding protein-immunoglobulin fusion protein comprises at least one immunoglobulin variable region polypeptide, which may be a light chain or a heavy chain variable region polypeptide, and in certain embodiments the fusion protein comprises at least one such light chain V-region and one such heavy chain V-region and at least one linker peptide that is fused to each of the V-regions. Construction of such binding domains, for example single chain Fv domains, is well known in the art and is described in greater detail in the Examples below, and has been described, for example, in U.S. Pat. Nos. 5,892,019 and references cited therein; selection and assembly of single-chain variable regions and of linker polypeptides that may be fused to each of a heavy chain-derived and a light chain-derived V region (e.g., to generate a binding domain that comprises a single-chain Fv polypeptide) is also known to the art and described herein and, for example, in U.S. Pat. Nos. 5,869,620, U.S. Pat. No. 4,704,692 and U.S. Pat. No. 4,946,778. In certain embodiments all or a portion of an immunoglobulin sequence that is derived from a non-human source may be "humanized" according to recognized procedures for generating humanized antibodies, i.e., immunoglobulin sequences into which human Ig sequences are introduced to reduce the degree to which a human immune system would perceive such proteins as foreign (see, e.g., U.S. Pat. Nos. 5,693,762; 5,585,089; 4,816,567; 5,225,539; 5,530,101; and references cited therein)

Once a binding domain-immunoglobulin fusion protein as provided herein has been designed, DNAs encoding the polypeptide may be synthesized via oligonucleotide synthesis as described, for example, in Sinha et al., *Nucleic Acids Res.*, 12, 4539-4557 (1984); assembled via PCR as described, for example in Innis, Ed., *PCR Protocols*, Academic Press (1990) and also in Better et al. *J. Biol. Chem.* 267, 16712-16118 (1992); cloned and expressed via standard procedures as described, for example, in Ausubel et al., Eds., *Current Protocols in Molecular Biology*, John Wiley & Sons, New York (1989) and also in Robinson et al., *Hum. Antibod. Hybridomas*, 2, 84-93 (1991); and tested for specific antigen binding activity, as described, for example, in Harlow et al., Eds., *Antibodies: A Laboratory Manual*, Chapter 14, Cold Spring Harbor Laboratory, Cold Spring Harbor (1988) and Munson et al., *Anal. Biochem.*, 107, 220-239 (1980).

The preparation of single polypeptide chain binding molecules of the Fv region, single-chain Fv molecules, is described in U.S. Pat. No. 4,946,778, which is incorporated herein by reference. In the present invention, single-chain Fv-like molecules are synthesized by encoding a first variable region of the heavy or light chain, followed by one or more linkers to the variable region of the corresponding light or heavy chain, respectively. The selection of appropriate linker (s) between the two variable regions is described in U.S. Pat. No. 4,946,778. An exemplary linker described herein is (Gly-Gly-Gly-Gly-Ser)$_3$. The linker is used to convert the naturally aggregated but chemically separate heavy and light chains into the amino terminal antigen binding portion of a single polypeptide chain, wherein this antigen binding portion will fold into a structure similar to the original structure made of two polypeptide chains and thus retain the ability to bind to the antigen of interest. The nucleotide sequences encoding the variable regions of the heavy and light chains, joined by a sequence encoding a linker, are joined to a nucleotide sequence encoding antibody constant regions. The constant regions are those which permit the resulting polypeptide to form interchain disulfide bonds to form a dimer, and which contain desired effector functions, such as the ability to mediate antibody-dependent cellular cytotoxicity (ADCC). For an immunoglobulin-like molecule of the invention which is intended for use in humans, the constant regions will typically be substantially human to minimize a potential anti-human immune response and to provide appropriate effector functions. Manipulation of sequences encoding antibody constant regions is described in the PCT publication of Morrison and Oi, WO 89/07142, which is incorporated herein by reference. In preferred embodiments, the CH1 domain is deleted and the carboxyl end of the second variable region is joined to the amino terminus of CH2 through the hinge region. The Cys residue of the hinge which makes a disulfide bond with a corresponding Cys of the light chain, to hold the heavy and light chains of the native antibody molecule, can be deleted or, preferably, is substituted with, e.g., a Pro residue or the like.

As described above, the present invention provides recombinant expression constructs capable of directing the expression of binding domain-immunoglobulin fusion proteins as provided herein. The amino acids, which occur in the various amino acid sequences referred to herein, are identified according to their well known three letter or one letter abbreviations. The nucleotides, which occur in the various DNA sequences or fragments thereof referred herein, are designated with the standard single letter designations used routinely in the art. A given amino acid sequence may also encompass similar amino acid sequences having only minor changes, for example by way of illustration and not limitation, covalent chemical modifications, insertions, deletions and substitutions, which may further include conservative substitutions. Amino acid sequences that are similar to one another may share substantial regions of sequence homology. In like fashion, nucleotide sequences may encompass substantially similar nucleotide sequences having only minor changes, for example by way of illustration and not limitation, covalent chemical modifications, insertions, deletions and substitutions, which may further include silent mutations owing to degeneracy of the genetic code. Nucleotide sequences that are similar to one another may share substantial regions of sequence homology.

The presence of a malignant condition in a subject refers to the presence of dysplastic, cancerous and/or transformed cells in the subject, including, for example neoplastic, tumor, non-contact inhibited or oncogenically transformed cells, or the like. In preferred embodiments contemplated by the present invention, for example, such cancer cells are malignant hematopoietic cells, such as transformed cells of lymphoid lineage and in particular, B-cell lymphomas and the like; cancer cells may in certain preferred embodiments also be epithelial cells such as carcinoma cells. The invention also contemplates B-cell disorders, which may include certain malignant conditions that affect B-cells (e.g., B-cell lymphoma) but which is not intended to be so limited, and which is also intended to encompass autoimmune diseases and in particular, diseases, disorders and conditions that are characterized by autoantibody production.

Autoantibodies are antibodies that react with self antigens. Autoantibodies are detected in several autoimmune diseases (i.e., a disease, disorder or condition wherein a host immune system generates an inappropriate anti-"self" immune reaction) where they are involved in disease activity. The current treatments for these autoimmune diseases are immunosuppressive drugs that require continuing administration, lack specificity, and cause significant side effects. New approaches that can eliminate autoantibody production with minimal toxicity will address an unmet medical need for a spectrum of diseases that affect many people. The subject invention binding domain-immunoglobulin fusion protein is designed for improved penetration into lymphoid tissues. Depletion of B lymphocytes interrupts the autoantibody production cycle, and allows the immune system to reset as new B lymphocytes are produced from precursors in the bone marrow.

A number of diseases have been identified for which beneficial effects are believed, according to non-limiting theory, to result from B cell depletion therapy; a brief description of several exemplars of these diseases follows.

Autoimmune thyroid disease includes Graves' disease and Hashimoto's thyroiditis. In the United States alone, there are about 20 million people who have some form of autoimmune thyroid disease. Autoimmune thyroid disease results from the production of autoantibodies that either stimulate the thyroid to cause hyperthyroidism (Graves' disease) or destroy the thyroid to cause hypothyroidism (Hashimoto's thyroiditis). Stimulation of the thyroid is caused by autoantibodies that bind and activate the thyroid stimulating hormone (TSH) receptor. Destruction of the thyroid is caused by autoantibodies that react with other thyroid antigens.

Current therapy for Graves' disease includes surgery, radioactive iodine, or antithyroid drug therapy. Radioactive iodine is widely used, since antithyroid medications have significant side effects and disease recurrence is high. Surgery is reserved for patients with large goiters or where there is a need for very rapid normalization of thyroid function. There are no therapies that target the production of autoantibodies responsible for stimulating the TSH receptor. Current therapy for Hashimoto's thyroiditis is levothyroxine sodium, and therapy is usually lifelong because of the low likelihood of remission. Suppressive therapy has been shown to shrink goiters in Hashimoto's thryoiditis, but no therapies that reduce autoantibody production to target the disease mechanism are known.

Rheumatoid arthritis (RA) is a chronic disease characterized by inflammation of the joints, leading to swelling, pain, and loss of function. RA effects an estimated 2.5 million people in the United States. RA is caused by a combination of events including an initial infection or injury, an abnormal immune response, and genetic factors. While autoreactive T cells and B cells are present in RA, the detection of high levels of antibodies that collect in the joints, called rheumatoid factor, is used in the diagnosis of RA. Current therapy for RA includes many medications for managing pain and slowing the progression of the disease. No therapy has been found that can cure the disease. Medications include nonsteroidal anti-inflammatory drugs (NSAIDS), and disease modifying anti-rheumatic drugs (DMARDS). NSAIDS are effective in benign disease, but fail to prevent the progression to joint destruction and debility in severe RA. Both NSAIDS and DMARDS are associated with signficant side effects. Only one new DMARD, Leflunomide, has been approved in over 10 years. Leflunomide blocks production of autoantibodies, reduces inflammation, and slows progression of RA. However, this drug also causes severe side effects including nausea, diarrhea, hair loss, rash, and liver injury.

Systemic Lupus Erythematosus (SLE) is an autoimmune disease caused by recurrent injuries to blood vessels in multiple organs, including the kidney, skin, and joints. SLE effects over 500,000 people in the United States. In patients with SLE, a faulty interaction between T cells and B cells results in the production of autoantibodies that attack the cell nucleus. These include anti-double stranded DNA and anti-Sm antibodies. Autoantibodies that bind phospholipids are also found in about half of SLE patients, and are responsible for blood vessel damage and low blood counts. Immune complexes accumulate the kidneys, blood vessels, and joints of SLE patients, where they cause inflammation and tissue damage. No treatment for SLE has been found to cure the disease. NSAIDS and DMARDS are used for therapy depending upon the severity of the disease. Plasmapheresis with plasma exchange to remove autoantibodies can cause temporary improvement in SLE patients. There is general agreement that autoantibodies are responsible for SLE, so new therapies that deplete the B cell lineage, allowing the immune system to reset as new B cells are generated from precursors, offer hope for long lasting benefit in SLE patients.

Sjogrens syndrome is an autoimmune disease characterized by destruction of the body's moisture producing glands. Sjogrens syndrome is one of the most prevalent autoimmune disorders, striking up to 4 million people in the United States. About half of people with Sjogren's also have a connective tissue disease, such as rheumatoid arthritis, while the other half have primary Sjogren's with no other concurrent autoimmune disease. Autoantibodies, including anti-nuclear antibodies, rheumatoid factor, anti-fodrin, and anti-muscarinic receptor are often present in patients with Sjogrens syndrome. Conventional therapy includes corticosteroids.

Immune Thrombocytopenic purpura (ITP) is caused by autoantibodies that bind to blood platelets and cause their destruction. Some cases of ITP are caused by drugs, and others are associated with infection, pregnancy, or autoimmune disease such as SLE. About half of all cases are classified as "idiopathic", meaning the cause is unknown. The treatment of ITP is determined by the severity of the symptoms. In some cases, no therapy is needed. In most cases, immunosuppressive drugs, including corticosteroids or intravenous infusions of immune globulin to deplete T cells. Another treatment that usually results in an increased number of platelets is removal of the spleen, the organ that destroys antibody-coated platelets. More potent immunosuppressive drugs, including cyclosporine, cyclophosphamide, or azathioprine are used for patients with severe cases. Removal of autoantibodies by passage of patients' plasma over a Protein A column is used as a second line treatment in patients with severe disease.

Multiple Sclerosis (MS) is an autoimmune disease characterized by inflammation of the central nervous system and destruction of myelin, which insulates nerve cell fibers in the brain, spinal cord, and body. Although the cause of MS is unknown, it is widely believed that autoimmune T cells are primary contributors to the pathogenesis of the disease. However, high levels of antibodies are present in the cerebral spinal fluid of patients with MS, and some theories predict that the B cell response leading to antibody production is important for mediating the disease. No B cell depletion therapies have been studies in patients with MS. There is no cure for MS. Current therapy is corticosteroids, which can reduce the duration and severity of attacks, but do not affect the course of MS over time. New biotechnology interferon (IFN) therapies for MS have recently been approved.

Myasthenia Gravis (MG) is a chronic autoimmune neuromuscular disorder that is characterized by weakness of the voluntary muscle groups. MG effects about 40,000 people in the United States. MG is caused by autoantibodies that bind to acetylcholine receptors expressed at neuromuscular junctions. The autoantibodies reduce or block acetylcholine receptors, preventing the transmission of signals from nerves to muscles. There is no known cure for MG. Common treatments include immunosuppression with corticosteroids, cyclosporine, cyclophosphamide, or azathioprine. Surgical removal of the thymus is often used to blunt the autoimmune response. Plasmapheresis, used to reduce autoantibody levels in the blood, is effective in MG, but is short-lived because the production of autoantibodies continues. Plasmapheresis is usually reserved for severe muscle weakness prior to surgery.

Psoriasis effects approximately five million people. Autoimmune inflammation in the skin. Psoriasis associated with arthritis in 30% (psoriatic arthritis). Many treatments, including steroids, UV light retenoids, vitamin D derivatives, cyclosporine, methotrexate.

Scleroderma is a chronic autoimmune disease of the connective tissue that is also known as systemic sclerosis. Scleroderma is characterized by an overproduction of collagen, resulting in a thickening of the skin. Approximately 300,000 people in the United States have scleroderma.

Inflammatory Bowel Disease including Crohn's disease and Ulcerative colitis, are autoimmune diseases of the digestive system.

The present invention further relates to constructs encoding binding domain-immunoglobulin fusion proteins, and in particular to methods for administering recombinant constructs encoding such proteins that may be expressed, for example, as fragments, analogs and derivatives of such polypeptides. The terms "fragment," "derivative" and "analog" when referring to binding domain-immunoglobulin fusion polypeptides or fusion proteins, refers to any binding domain-immunoglobulin fusion polypeptide or fusion protein that retains essentially the same biological function or activity as such polypeptide. Thus, an analog includes a proprotein which can be activated by cleavage of the proprotein portion to produce an active binding domain-immunoglobulin fusion polypeptide.

A fragment, derivative or analog of an binding domain-immunoglobulin fusion polypeptide or fusion protein, including binding domain-immunoglobulin fusion polypeptides or fusion proteins encoded by the cDNAs referred to herein, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which additional amino acids are fused to the binding domain-immunoglobulin fusion polypeptide, including amino acids that are employed for detection or specific functional alteration of the binding domain-immunoglobulin fusion polypeptide or a proprotein sequence. Such fragments, derivatives and analogs are deemed to be within the scope of those skilled in the art from the teachings herein.

The polypeptides of the present invention include binding domain-immunoglobulin fusion polypeptides and fusion proteins having binding domain polypeptide amino acid sequences that are identical or similar to sequences known in the art, or fragments or portions thereof. For example by way of illustration and not limitation, the human CD154 molecule extracellular domain is contemplated for use according to the instant invention, as are polypeptides having at least 70% similarity (preferably a 70% identity) and more preferably 90% similarity (more preferably a 90% identity) to the reported polypeptide and still more preferably a 95% similarity (still more preferably a 95% identity) to the reported polypeptides and to portions of such polypeptides, wherein such portions of a binding domain-immunoglobulin fusion polypeptide generally contain at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide. Fragments or portions of the nucleic acids encoding polypeptides of the present invention may be used to synthesize full-length nucleic acids of the present invention. As used herein, "% identity" refers to the percentage of identical amino acids situated at corresponding amino acid residue positions when two or more polypeptide are aligned and their sequences analyzed using a gapped BLAST algorithm (e.g., Altschul et al., 1997 *Nucl. Ac. Res.* 25:3389) which weights sequence gaps and sequence mismatches according to the default weightings provided by the National Institutes of Health/NCBI database (National Center for Biotechnology Information, National Library of Medicine, Building 38A, Bethesda, Md. 20894).

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acids could be part of a vector and/or such nucleic acids or polypeptides could be part of a composition, and still be isolated in that such vector or composition is not part of its natural environment.

The term "gene" means the segment of DNA involved in producing a polypeptide chain; it includes regions preceding and following the coding region "leader and trailer" as well as intervening sequences (introns) between individual coding segments (exons).

As described herein, the invention provides binding domain-immunoglobulin fusion proteins encoded by nucleic acids that have the binding domain coding sequence fused in frame to an additional immunoglobulin domain encoding sequence to provide for expression of a binding domain polypeptide sequence fused to an additional functional polypeptide sequence that permits, for example by way of illustration and not limitation, detection, functional alteration, isolation and/or purification of the fusion protein. Such fusion proteins may permit functional alteration of a binding domain by containing additional immunoglobulin-derived polypeptide sequences that influence behavior of the fusion product, for example (and as described above) by reducing the availability of sufhydryl groups for participation in disulfide bond formation, and by conferring the ability to potentiate ADCC and/or CDC.

Modification of the polypeptide may be effected by any means known to those of skill in this art. The preferred methods herein rely on modification of DNA encoding the fusion protein and expression of the modified DNA. DNA encoding one of the binding domain-immunoglobulin fusions discussed above may be mutagenized using standard methodologies, including those described below. For example, cysteine residues that may otherwise facilitate multimer formation or promote particular molecular conformations can be deleted from a polypeptide or replaced, e.g., cysteine residues that are responsible for aggregate formation. If necessary, the identity of cysteine residues that contribute to aggregate formation may be determined empirically, by deleting and/or replacing a cysteine residue and ascertaining whether the resulting protein aggregates in solutions containing physiologically acceptable buffers and salts. In addition, fragments of binding domain-immunoglobulin fusions may be constructed and used. As noted above, the counterreceptor/ligand binding domains for many candidate binding domain-immunoglobulin fusion have been delineated, such that one having ordinary skill in the art may readily select appropriate polypeptide domains for inclusion in the encoded products of the instant expression constructs.

Conservative substitutions of amino acids are well-known and may be made generally without altering the biological activity of the resulting binding domain-immunoglobulin fusion protein molecule. For example, such substitutions are generally made by interchanging within the groups of polar residues, charged residues, hydrophobic residues, small residues, and the like. If necessary, such substitutions may be determined empirically merely by testing the resulting modified protein for the ability to bind to the appropriate cell surface receptors in in vitro biological assays, or to bind to appropriate antigens or desired target molecules.

The present invention further relates to nucleic acids which hybridize to binding domain-immunoglobulin fusion protein encoding polynucleotide sequences as provided herein, or their complements, as will be readily apparent to those familiar with the art, if there is at least 70%, preferably at least 90%, and more preferably at least 95% identity between the sequences. The present invention particularly relates to nucleic acids which hybridize under stringent conditions to the binding domain-immunoglobulin fusion encoding nucleic acids referred to herein. As used herein, the term "stringent conditions" means hybridization will occur only if there is at least 95% and preferably at least 97% identity between the sequences. The nucleic acids which hybridize to binding domain-immunoglobulin fusion encoding nucleic acids referred to herein, in preferred embodiments, encode polypeptides which retain substantially the same biological function or activity as the binding domain-immunoglobulin fusion polypeptides encoded by the cDNAs of the references cited herein.

As used herein, to "hybridize" under conditions of a specified stringency is used to describe the stability of hybrids formed between two single-stranded nucleic acid molecules. Stringency of hybridization is typically expressed in conditions of ionic strength and temperature at which such hybrids are annealed and washed. Typically "high", "medium" and "low" stringency encompass the following conditions or equivalent conditions thereto: high stringency: 0.1×SSPE or SSC, 0.1% SDS, 65° C.; medium stringency: 0.2×SSPE or SSC, 0.1% SDS, 50° C.; and low stringency: 1.0×SSPE or SSC, 0.1% SDS, 50° C. As known to those having ordinary skill in the art, variations in stringency of hybridization conditions may be achieved by altering the time, temperature and/or concentration of the solutions used for prehybridization, hybridization and wash steps, and suitable conditions may also depend in part on the particular nucleotide sequences of the probe used, and of the blotted, proband nucleic acid sample. Accordingly, it will be appreciated that suitably stringent conditions can be readily selected without undue experimentation where a desired selectivity of the probe is identified, based on its ability to hybridize to one or more certain proband sequences while not hybridizing to certain other proband sequences.

The nucleic acids of the present invention, also referred to herein as polynucleotides, may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. A coding sequence which encodes an binding domain-immunoglobulin fusion polypeptide for use according to the invention may be identical to the coding sequence known in the art for any given binding domain-immunoglobulin fusion, or may be a different coding sequence, which, as a result of the redundancy or degeneracy of the genetic code, encodes the same binding domain-immunoglobulin fusion polypeptide.

The nucleic acids which encode binding domain-immunoglobulin fusion polypeptides for use according to the invention may include, but are not limited to: only the coding sequence for the binding domain-immunoglobulin fusion polypeptide; the coding sequence for the binding domain-immunoglobulin fusion polypeptide and additional coding sequence; the coding sequence for the binding domain-immunoglobulin fusion polypeptide (and optionally additional coding sequence) and non-coding sequence, such as introns or non-coding sequences 5' and/or 3' of the coding sequence for the binding domain-immunoglobulin fusion polypeptide, which for example may further include but need not be limited to one or more regulatory nucleic acid sequences that may be a regulated or regulatable promoter, enhancer, other transcription regulatory sequence, repressor binding sequence, translation regulatory sequence or any other regulatory nucleic acid sequence. Thus, the term "nucleic acid encoding" or "polynucleotide encoding" a binding domain-immunoglobulin fusion protein encompasses a nucleic acid which includes only coding sequence for a binding domain-immunoglobulin fusion polypeptide as well as a nucleic acid which includes additional coding and/or non-coding sequence(s).

Nucleic acids and oligonucleotides for use as described herein can be synthesized by any method known to those of skill in this art (see, e.g., WO 93/01286, U.S. application Ser. No. 07/723,454, now abandoned U.S. Pat. No. 5,218,088; U.S. Pat. No. 5,175,269; U.S. Pat. No. 5,109,124). Identification of oligonucleotides and nucleic acid sequences for use in the present invention involves methods well known in the art. For example, the desirable properties, lengths and other characteristics of useful oligonucleotides are well known. In certain embodiments, synthetic oligonucleotides and nucleic acid sequences may be designed that resist degradation by endogenous host cell nucleolytic enzymes by containing such linkages as: phosphorothioate, methylphosphonate, sulfone, sulfate, ketyl, phosphorodithioate, phosphoramidate, phosphate esters, and other such linkages that have proven useful in antisense applications (see, e.g., Agrwal et al., Tetrehedron Lett. 28:3539-3542 (1987); Miller et al., J. Am. Chem. Soc. 93:6657-6665 (1971); Stec et al., Tetrehedron Lett. 26:2191-2194 (1985); Moody et al., Nucl. Acids Res. 12:4769-4782 (1989); Uznanski et al., Nucl. Acids Res. (1989); Letsinger et al., Tetrahedron 40:137-143 (1984); Eckstein, Annu. Rev. Biochem. 54:367-402 (1985); Eckstein, Trends Biol. Sci. 14:97-100 (1989); Stein In: *Oligodeoxynucleotides. Antisense Inhibitors of Gene Expression*, Cohen, Ed, Macmillan Press, London, pp. 97-117 (1989); Jager et al., Biochemistry 27:7237-7246 (1988)).

In one embodiment, the present invention provides truncated components (e.g., binding domain polypeptide, hinge region polypeptide, linker, etc.) for use in a binding domain-immunoglobulin fusion protein, and in another embodiment the invention provides nucleic acids encoding a binding domain-immunoglobulin fusion protein having such truncated components. A truncated molecule may be any molecule that comprises less than a full length version of the molecule. Truncated molecules provided by the present invention may include truncated biological polymers, and in preferred embodiments of the invention such truncated molecules may be truncated nucleic acid molecules or truncated polypeptides. Truncated nucleic acid molecules have less than the full length nucleotide sequence of a known or described nucleic acid molecule, where such a known or described nucleic acid molecule may be a naturally occurring, a synthetic or a recombinant nucleic acid molecule, so long as one skilled in the art would regard it as a full length molecule. Thus, for example, truncated nucleic acid molecules that correspond to a gene sequence contain less than the full length gene where the gene comprises coding and non-coding sequences, promoters, enhancers and other regulatory sequences, flanking sequences and the like, and other functional and non-functional sequences that are recognized as part of the gene. In another example, truncated nucleic acid molecules that correspond to a mRNA sequence contain less than the full length mRNA transcript, which may include various translated and non-translated regions as well as other functional and non-functional sequences.

In other preferred embodiments, truncated molecules are polypeptides that comprise less than the full length amino acid sequence of a particular protein or polypeptide component. As used herein "deletion" has its common meaning as understood by those familiar with the art, and may refer to molecules that lack one or more of a portion of a sequence from either terminus or from a non-terminal region, relative to a corresponding full length molecule, for example, as in the case of truncated molecules provided herein. Truncated molecules that are linear biological polymers such as nucleic acid molecules or polypeptides may have one or more of a deletion from either terminus of the molecule or a deletion from a non-terminal region of the molecule, where such deletions may be deletions of 1-1500 contiguous nucleotide or amino acid residues, preferably 1-500 contiguous nucleotide or amino acid residues and more preferably 1-300 contiguous nucleotide or amino acid residues. In certain particularly preferred embodiments truncated nucleic acid molecules may have a deletion of 270-330 contiguous nucleotides. In certain other particularly preferred embodiments truncated polypeptide molecules may have a deletion of 80-140 contiguous amino acids.

The present invention further relates to variants of the herein referenced nucleic acids which encode fragments, analogs and/or derivatives of a binding domain-immunoglobulin fusion polypeptide. The variants of the nucleic acids encoding binding domain-immunoglobulin fusion may be naturally occurring allelic variants of the nucleic acids or non-naturally occurring variants. As is known in the art, an allelic variant is an alternate form of a nucleic acid sequence which may have at least one of a substitution, a deletion or an addition of one or more nucleotides, any of which does not substantially alter the function of the encoded binding domain-immunoglobulin fusion polypeptide.

Variants and derivatives of binding domain-immunoglobulin fusion may be obtained by mutations of nucleotide sequences encoding binding domain-immunoglobulin fusion polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making such alterations are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods BioTechniques*, January 1985, 12-19); Smith et al. (*Genetic Engineering: Principles and Methods*, Plenum Press, 1981); Kunkel (Proc. Natl. Acad. Sci. USA 82:488, 1985); Kunkel et al. (*Methods in Enzymol.* 154:367, 1987); and U.S. Pat. Nos. 4,518,584 and 4,737,462.

As an example, modification of DNA may be performed by site-directed mutagenesis of DNA encoding the protein combined with the use of DNA amplification methods using primers to introduce and amplify alterations in the DNA template, such as PCR splicing by overlap extension (SOE). Site-directed mutagenesis is typically effected using a phage vector that has single- and double-stranded forms, such as M13 phage vectors, which are well-known and commercially available. Other suitable vectors that contain a single-stranded phage origin of replication may be used (see, e.g., Veira et al., Meth. Enzymol. 15:3, 1987). In general, site-directed mutagenesis is performed by preparing a single-stranded vector that encodes the protein of interest (e.g., all or a component portion of a given binding domain-immunoglobulin fusion protein). An oligonucleotide primer that contains the desired mutation within a region of homology to the DNA in the single-stranded vector is annealed to the vector followed by addition of a DNA polymerase, such as *E. coli* DNA polymerase I (Klenow fragment), which uses the double stranded region as a primer to produce a heteroduplex in which one strand encodes the altered sequence and the other the original sequence. The heteroduplex is introduced into appropriate bacterial cells and clones that include the desired mutation are selected. The resulting altered DNA molecules may be expressed recombinantly in appropriate host cells to produce the modified protein.

Equivalent DNA constructs that encode various additions or substitutions of amino acid residues or sequences, or deletions of terminal or internal residues or sequences not needed for biological activity are also encompassed by the invention. For example, and as discussed above, sequences encoding Cys residues that are not desirable or essential for biological activity can be altered to cause the Cys residues to be deleted or replaced with other amino acids, preventing formation of incorrect intramolecular disulfide bridges upon renaturation.

Host organisms include those organisms in which recombinant production of binding domain-immunoglobulin fusion products encoded by the recombinant constructs of the present invention may occur, such as bacteria (for example, *E. coli*), yeast (for example, *Saccharomyces cerevisiae* and *Pichia pastoris*), insect cells and mammals, including in vitro and in vivo expression. Host organisms thus may include organisms for the construction, propagation, expression or other steps in the production of the compositions provided herein; hosts also include subjects in which immune responses take place, as described above. Presently preferred host organisms are *E. coli* bacterial strains, inbred murine strains and murine cell lines, and human cells, subjects and cell lines.

The DNA construct encoding the desired binding domain-immunoglobulin fusion is introduced into a plasmid for expression in an appropriate host. In preferred embodiments, the host is a bacterial host. The sequence encoding the ligand or nucleic acid binding domain is preferably codon-optimized for expression in the particular host. Thus, for example, if a human binding domain-immunoglobulin fusion is expressed in bacteria, the codons would be optimized for bacterial usage. For small coding regions, the gene can be synthesized as a single oligonucleotide. For larger proteins, splicing of multiple oligonucleotides, mutagenesis, or other techniques known to those in the art may be used. The sequences of nucleotides in the plasmids that are regulatory regions, such as promoters and operators, are operationally associated with one another for transcription. The sequence of nucleotides encoding a binding domain-immunoglobulin fusion protein may also include DNA encoding a secretion signal, whereby the resulting peptide is a precursor protein. The resulting processed protein may be recovered from the periplasmic space or the fermentation medium.

In preferred embodiments, the DNA plasmids also include a transcription terminator sequence. As used herein, a "transcription terminator region" is a sequence that signals transcription termination. The entire transcription terminator may be obtained from a protein-encoding gene, which may be the same or different from the inserted binding domain-immunoglobulin fusion encoding gene or the source of the promoter. Transcription terminators are optional components of the expression systems herein, but are employed in preferred embodiments.

The plasmids used herein include a promoter in operative association with the DNA encoding the protein or polypeptide of interest and are designed for expression of proteins in a suitable host as described above (e.g., bacterial, murine or human) depending upon the desired use of the plasmid (e.g., administration of a vaccine containing binding domain-immunoglobulin fusion encoding sequences). Suitable promoters for expression of proteins and polypeptides herein are widely available and are well known in the art. Inducible promoters or constitutive promoters that are linked to regulatory regions are preferred. Such promoters include, but are not limited to, the T7 phage promoter and other T7-like phage promoters, such as the T3, T5 and SP6 promoters, the trp, lpp, and lac promoters, such as the lacUV5, from *E. coli*; the P10 or polyhedrin gene promoter of baculovirus/insect cell expression systems (see, e.g., U.S. Pat. Nos. 5,243,041, 5,242,687, 5,266,317, 4,745,051, and 5,169,784) and inducible promoters from other eukaryotic expression systems. For expression of the proteins such promoters are inserted in a plasmid in operative linkage with a control region such as the lac operon.

Preferred promoter regions are those that are inducible and functional in *E. coli*. Examples of suitable inducible promoters and promoter regions include, but are not limited to: the *E. coli* lac operator responsive to isopropyl β-D-thiogalactopyranoside (IPTG; see Nakamura et al., *Cell* 18:1109-1117, 1979); the metallothionein promoter metal-regulatory-elements responsive to heavy-metal (e.g:, zinc) induction (see, e.g., U.S. Pat. No. 4,870,009 to Evans et al.); the phage T71ac promoter responsive to IPTG (see, e.g., U.S. Pat. No. 4,952, 496; and Studier et al., *Meth. Enzymol.* 185:60-89, 1990) and the TAC promoter.

The plasmids may optionally include a selectable marker gene or genes that are functional in the host. A selectable marker gene includes any gene that confers a phenotype on bacteria that allows transformed bacterial cells to be identified and selectively grown from among a vast majority of untransformed cells. Suitable selectable marker genes for bacterial hosts, for example, include the ampicillin resistance gene ($Amp^r$), tetracycline resistance gene ($Tc^r$) and the kanamycin resistance gene ($Kan^r$). The kanamycin resistance gene is presently preferred.

The plasmids may also include DNA encoding a signal for secretion of the operably linked protein. Secretion signals suitable for use are widely available and are well known in the art. Prokaryotic and eukaryotic secretion signals functional in *E. coli* may be employed. The presently preferred secretion signals include, but are not limited to, those encoded by the following *E. coli* genes: ompA, ompT, ompF, ompC, beta-lactamase, and alkaline phosphatase, and the like (von Heijne, *J. Mol. Biol.* 184:99-105, 1985). In addition, the bacterial pelB gene secretion signal (Lei et al., *J. Bacteriol.* 169:4379, 1987), the phoA secretion signal, and the cek2 functional in insect cell may be employed. The most preferred secretion signal is the *E. coli* ompA secretion signal. Other prokaryotic and eukaryotic secretion signals known to those of skill in the art may also be employed (see, e.g., von Heijne, *J. Mol. Biol.* 184:99-105, 1985). Using the methods described herein, one of skill in the art can substitute secretion signals that are functional in either yeast, insect or mammalian cells to secrete proteins from those cells.

Preferred plasmids for transformation of *E. coli* cells include the pET expression vectors (e.g., pET-11a, pET-12a-c, pET-15b; see U.S. Pat. No. 4,952,496; available from Novagen, Madison, Wis.). Other preferred plasmids include the pKK plasmids, particularly pKK 223-3, which contains the tac promoter (Brosius et al., *Proc. Natl. Acad. Sci.* 81:6929, 1984; Ausubel et al., *Current Protocols in Molecular Biology*; U.S. Pat. Nos. 5,122,463, 5,173,403, 5,187,153, 5,204,254, 5,212,058, 5,212,286, 5,215,907, 5,220,013, 5,223,483, and 5,229,279). Plasmid pKK has been modified by replacement of the ampicillin resistance gene with a kanamycin resistance gene. (Available from Pharmacia; obtained from pUC4K, see, e.g., Vieira et al. (*Gene* 19:259-268, 1982; and U.S. Pat. No. 4,719,179.) Baculovirus vectors, such as pBlueBac (also called pJVETL and derivatives thereof), particularly pBlueBac III (see, e.g., U.S. Pat. Nos. 5,278,050, 5,244,805, 5,243,041, 5,242,687, 5,266,317, 4,745,051, and 5,169,784; available from Invitrogen, San Diego) may also be used for expression of the polypeptides in insect cells. Other plasmids include the pIN-IIIompA plasmids (see U.S. Pat. No. 4,575,013; see also Duffaud et al., *Meth. Enz.* 153:492-507, 1987), such as pIN-IIIompA2.

Preferably, the DNA molecule is replicated in bacterial cells, preferably in *E. coli*. The preferred DNA molecule also includes a bacterial origin of replication, to ensure the maintenance of the DNA molecule from generation to generation of the bacteria. In this way, large quantities of the DNA molecule can be produced by replication in bacteria. Preferred bacterial origins of replication include, but are not limited to, the fl-ori and col E1 origins of replication. Preferred hosts contain chromosomal copies of DNA encoding T7 RNA polymerase operably linked to an inducible promoter, such as the lacUV promoter (see U.S. Pat. No. 4,952, 496). Such hosts include, but are not limited to, lysogens *E. coli* strains HMS 174(DE3)pLysS, BL21 (DE3)pLysS, HMS 174(DE3) and BL21 (DE3). Strain BL21(DE3) is preferred. The pLys strains provide low levels of T7 lysozyme, a natural inhibitor of T7 RNA polymerase.

The DNA molecules provided may also contain a gene coding for a repressor protein. The repressor protein is capable of repressing the transcription of a promoter that contains sequences of nucleotides to which the repressor protein binds. The promoter can be derepressed by altering the physiological conditions of the cell. For example, the alteration can be accomplished by adding to the growth medium a molecule that inhibits the ability to interact with the operator or with regulatory proteins or other regions of the DNA or by altering the temperature of the growth media. Preferred repressor proteins include, but are not limited to the *E. coli* lacI repressor responsive to IPTG induction, the temperature sensitive λ cI857 repressor, and the like. The *E. coli* lacI repressor is preferred.

In general, recombinant constructs of the subject invention will also contain elements necessary for transcription and translation. In particular, such elements are preferred where the recombinant expression construct containing nucleic acid sequences encoding binding domain-immunoglobulin fusion proteins is intended for expression in a host cell or organism. In certain embodiments of the present invention, cell type preferred or cell type specific expression of a cell binding domain-immunoglobulin fusion encoding gene may be achieved by placing the gene under regulation of a promoter. The choice of the promoter will depend upon the cell type to be transformed and the degree or type of control desired. Promoters can be constitutive or active and may further be cell type specific, tissue specific, individual cell specific, event specific, temporally specific or inducible. Cell-type specific promoters and event type specific promoters are preferred. Examples of constitutive or nonspecific promoters include the SV40 early promoter (U.S. Pat. No. 5,118,627), the SV40 late promoter (U.S. Pat. No. 5,118,627), CMV early gene promoter (U.S. Pat. No. 5,168,062), and adenovirus promoter. In addition to viral promoters, cellular promoters are also amenable within the context of this invention. In particular, cellular promoters for the so-called housekeeping genes are useful. Viral promoters are preferred, because generally they are stronger promoters than cellular promoters.

Promoter regions have been identified in the genes of many eukaryotes including higher eukaryotes, such that suitable promoters for use in a particular host can be readily selected by those skilled in the art.

Inducible promoters may also be used. These promoters include MMTV LTR (PCT WO 91/13160), inducible by dexamethasone; metallothionein promoter, inducible by heavy metals; and promoters with cAMP response elements, inducible by cAMP. By using an inducible promoter, the nucleic acid sequence encoding a binding domain-immunoglobulin fusion protein may be delivered to a cell by the subject invention expression construct and will remain quiescent until the addition of the inducer. This allows further control on the timing of production of the gene product.

Event-type specific promoters are active or up-regulated only upon the occurrence of an event, such as tumorigenicity or viral infection. The HIV LTR is a well known example of an event-specific promoter. The promoter is inactive unless the tat gene product is present, which occurs upon viral infection. Some event-type promoters are also tissue-specific.

Additionally, promoters that are coordinately regulated with a particular cellular gene may be used. For example, promoters of genes that are coordinately expressed may be used when expression of a particular binding domain-immunoglobulin fusion protein-encoding gene is desired in concert with expression of one or more additional endogenous or exogenously introduced genes. This type of promoter is especially useful when one knows the pattern of gene expression relevant to induction of an immune response in a particular tissue of the immune system, so that specific immunocompetent cells within that tissue may be activated or otherwise recruited to participate in the immune response.

In addition to the promoter, repressor sequences, negative regulators, or tissue-specific silencers may be inserted to reduce non-specific expression of binding domain-immunoglobulin fusion protein encoding genes in certain situations, such as, for example, a host that is transiently immunocompromised as part of a therapeutic strategy. Multiple repressor elements may be inserted in the promoter region. Repression of transcription is independent on the orientation of repressor elements or distance from the promoter. One type of repressor sequence is an insulator sequence. Such sequences inhibit transcription (Dunaway et al., *Mol Cell Biol* 17: 182-9, 1997; Gdula et al., *Proc Natl Acad Sci USA* 93:9378-83, 1996, Chan et al., *J Virol* 70: 5312-28, 1996; Scott and Geyer, *EMBO J* 14:6258-67, 1995; Kalos and Fournier, *Mol Cell Biol* 15:198-207, 1995; Chung et al., *Cell* 74: 505-14, 1993) and will silence background transcription.

Repressor elements have also been identified in the promoter regions of the genes for type II (cartilage) collagen, choline acetyltransferase, albumin (Hu et al., *J. Cell Growth Differ.* 3(9):577-588, 1992), phosphoglycerate kinase (PGK-2) (Misuno et al., *Gene* 119(2):293-297, 1992), and in the 6-phosphofructo-2-kinase/fructose-2, 6-bisphosphatase gene. (Lemaigre et al., *Mol. Cell Biol.* 11(2):1099-1106.) Furthermore, the negative regulatory element Tse-1 has been identified in a number of liver specific genes, and has been shown to block cAMP response element-(CRE) mediated induction of gene activation in hepatocytes. (Boshart et al., *Cell* 61(5):905-916, 1990).

In preferred embodiments, elements that increase the expression of the desired product are incorporated into the construct. Such elements include internal ribosome binding sites (IRES; Wang and Siddiqui, *Curr. Top. Microbiol. Immunol* 203:99, 1995; Ehrenfeld and Semler, *Curr. Top. Microbiol. Immunol.* 203:65, 1995; Rees et al., *Biotechniques* 20:102, 1996; Sugimoto et al., *Biotechnology* 12:694, 1994). IRES increase translation efficiency. As well, other sequences may enhance expression. For some genes, sequences especially at the 5' end inhibit transcription and/or translation. These sequences are usually palindromes that can form hairpin structures. Any such sequences in the nucleic acid to be delivered are generally deleted. Expression levels of the transcript or translated product are assayed to confirm or ascertain which sequences affect expression. Transcript levels may be assayed by any known method, including Northern blot hybridization, RNase probe protection and the like. Protein levels may be assayed by any known method, including ELISA, western blot, immunocytochemistry or other well known techniques.

Other elements may be incorporated into the binding domain-immunoglobulin fusion protein encoding constructs of the present invention. In preferred embodiments, the construct includes a transcription terminator sequence, including a polyadenylation sequence, splice donor and acceptor sites, and an enhancer. Other elements useful for expression and maintenance of the construct in mammalian cells or other eukaryotic cells may also be incorporated (e.g., origin of replication). Because the constructs are conveniently produced in bacterial cells, elements that are necessary for, or that enhance, propagation in bacteria are incorporated. Such elements include an origin of replication, a selectable marker and the like.

As provided herein, an additional level of controlling the expression of nucleic acids encoding binding domain-immunoglobulin fusion proteins delivered to cells using the constructs of the invention may be provided by simultaneously delivering two or more differentially regulated nucleic acid constructs. The use of such a multiple nucleic acid construct approach may permit coordinated regulation of an immune response such as, for example, spatiotemporal coordination that depends on the cell type and/or presence of another expressed encoded component. Those familiar with the art will appreciate that multiple levels of regulated gene expression may be achieved in a similar manner by selection of suitable regulatory sequences, including but not limited to promoters, enhancers and other well known gene regulatory elements.

The present invention also relates to vectors, and to constructs prepared from known vectors that include nucleic acids of the present invention, and in particular to "recombinant expression constructs" that include any nucleic acids encoding binding domain-immunoglobulin fusion proteins and polypeptides according to the invention as provided above; to host cells which are genetically engineered with vectors and/or constructs of the invention and to methods of administering expression constructs comprising nucleic acid sequences encoding such binding domain-immunoglobulin fusion polypeptides and fusion proteins of the invention, or fragments or variants thereof, by recombinant techniques. Binding domain-immunoglobulin fusion proteins can be expressed in virtually any host cell under the control of appropriate promoters, depending on the nature of the construct (e.g., type of promoter, as described above), and on the nature of the desired host cell (e.g., whether postmitotic terminally differentiated or actively dividing; e.g., whether the expression construct occurs in host cell as an episome or is integrated into host cell genome). Appropriate cloning and expression vectors for use with prokaryotic and eukaryotic hosts are described by Sambrook, et al., *Molecular Cloning: A Laboratory Manual*, Second Edition, Cold Spring Harbor, N.Y., (1989); as noted above, in particularly preferred embodiments of the invention, recombinant expression is conducted in mammalian cells that have been transfected or transformed with the subject invention recombinant expression construct.

Typically, the constructs are derived from plasmid vectors. A preferred construct is a modified pNASS vector (Clontech, Palo Alto, Calif.), which has nucleic acid sequences encoding an ampicillin resistance gene, a polyadenylation signal and a T7 promoter site. Other suitable mammalian expression vectors are well known (see, e.g., Ausubel et al., 1995; Sambrook et al., supra; see also, e.g., catalogues from Invitrogen, San Diego, Calif.; Novagen, Madison, Wis.; Pharmacia, Piscataway, N.J.; and others). Presently preferred constructs may be prepared that include a dihydrofolate reductase (DHFR) encoding sequence under suitable regulatory control, for promoting enhanced production levels of the binding domain-immunoglobulin fusion protei, which levels result from gene amplification following application of an appropriate selection agent (e.g., methetrexate).

Generally, recombinant expression vectors will include origins of replication and selectable markers permitting transformation of the host cell, and a promoter derived from a highly-expressed gene to direct transcription of a downstream structural sequence, as described above. The heterologous structural sequence is assembled in appropriate phase with translation initiation and termination sequences. Thus, for example, the binding domain-immunoglobulin fusion protein encoding nucleic acids as provided herein may be included in any one of a variety of expression vector constructs as a recombinant expression construct for expressing a binding domain-immunoglobulin fusion polypeptide in a host cell. In certain preferred embodiments the constructs are included in formulations that are administered in vivo. Such vectors and constructs include chromosomal, nonchromosomal and synthetic DNA sequences, e.g., derivatives of SV40; bacterial plasmids; phage DNA; yeast plasmids; vectors derived from combinations of plasmids and phage DNA, viral DNA, such as vaccinia, adenovirus, fowl pox virus, and pseudorabies, or replication deficient retroviruses as described below. However, any other vector may be used for preparation of a recombinant expression construct, and in preferred embodiments such a vector will be replicable and viable in the host.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 *Current Protocols in Molecular Biology*, Greene Publ. Assoc. Inc. & John Wiley & Sons, Inc., Boston, Mass.); Sambrook et al. (1989 *Molecular Cloning*, Second Ed., Cold Spring Harbor Laboratory, Plainview, N.Y.); Maniatis et al. (1982 Molecular Cloning, Cold Spring Harbor Laboratory, Plainview, N.Y.); Glover (Ed.) (1985 *DNA Cloning Vol. I and II*, IRL Press, Oxford, UK); Hames and Higgins (Eds.), (1985 *Nucleic Acid Hybridization*, IRL Press, Oxford, UK); and elsewhere.

The DNA sequence in the expression vector is operatively linked to at least one appropriate expression control sequences (e.g., a constitutive promoter or a regulated promoter) to direct mRNA synthesis. Representative examples of such expression control sequences include promoters of eukaryotic cells or their viruses, as described above. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a nucleic acid encoding an binding domain-immunoglobulin fusion polypeptide is described herein.

Transcription of the DNA encoding the polypeptides of the present invention by higher eukaryotes may be increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

As provided herein, in certain embodiments the vector may be a viral vector such as a retroviral vector. (Miller et al., 1989 *BioTechniques* 7:980; Coffin and Varmus, 1996 Retroviruses, Cold Spring Harbor Laboratory Press, NY.) For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

Retroviruses are RNA viruses which can replicate and integrate into the genome of a host cell via a DNA intermediate. This DNA intermediate, or provirus, may be stably integrated into the host cell DNA. According to certain embodiments of the present invention, an expression construct may comprise a retrovirus into which a foreign gene that encodes a foreign protein is incorporated in place of normal retroviral RNA. When retroviral RNA enters a host cell coincident with infection, the foreign gene is also introduced into the cell, and may then be integrated into host cell DNA as if it were part of the retroviral genome. Expression of this foreign gene within the host results in expression of the foreign protein.

Most retroviral vector systems which have been developed for gene therapy are based on murine retroviruses. Such retroviruses exist in two forms, as free viral particles referred to as virions, or as proviruses integrated into host cell DNA. The virion form of the virus contains the structural and enzymatic proteins of the retrovirus (including the enzyme reverse transcriptase), two RNA copies of the viral genome, and portions of the source cell plasma membrane containing viral envelope glycoprotein. The retroviral genome is organized into four main regions: the Long Terminal Repeat (LTR), which contains cis-acting elements necessary for the initiation and termination of transcription and is situated both 5' and 3' of the coding genes, and the three coding genes gag, pol, and env. These three genes gag, pol, and env encode, respectively, internal viral structures, enzymatic proteins (such as integrase), and the envelope glycoprotein (designated gp70 and p15e) which confers infectivity and host range specificity of the virus, as well as the "R" peptide of undetermined function.

Separate packaging cell lines and vector producing cell lines have been developed because of safety concerns regarding the uses of retroviruses, including their use in expression constructs as provided by the present invention. Briefly, this methodology employs the use of two components, a retroviral vector and a packaging cell line (PCL). The retroviral vector contains long terminal repeats (LTRs), the foreign DNA to be transferred and a packaging sequence (y). This retroviral vector will not reproduce by itself because the genes which encode structural and envelope proteins are not included within the vector genome. The PCL contains genes encoding the gag, pol, and env proteins, but does not contain the packaging signal "y". Thus, a PCL can only form empty virion particles by itself. Within this general method, the retroviral vector is introduced into the PCL, thereby creating a vector-producing cell line (VCL). This VCL manufactures virion particles containing only the retroviral vector's (foreign) genome, and therefore has previously been considered to be a safe retrovirus vector for therapeutic use.

"Retroviral vector construct" refers to an assembly which is, within preferred embodiments of the invention, capable of directing the expression of a sequence(s) or gene(s) of interest, such as binding domain-immunoglobulin fusion encoding nucleic acid sequences. Briefly, the retroviral vector construct must include a 5' LTR, a tRNA binding site, a packaging signal, an origin of second strand DNA synthesis and a 3' LTR. A wide variety of heterologous sequences may be included within the vector construct, including for example, sequences which encode a protein (e.g., cytotoxic protein, disease-associated antigen, immune accessory molecule, or replacement gene), or which are useful as a molecule itself (e.g., as a ribozyme or antisense sequence).

Retroviral vector constructs of the present invention may be readily constructed from a wide variety of retroviruses, including for example, B, C, and D type retroviruses as well as spumaviruses and lentiviruses (see, e.g., RNA Tumor Viruses, Second Edition, Cold Spring Harbor Laboratory, 1985). Such retroviruses may be readily obtained from depositories or collections such as the American Type Culture Collection ("ATCC"; Rockville, Md.), or isolated from known sources using commonly available techniques. Any of the above retroviruses may be readily utilized in order to assemble or construct retroviral vector constructs, packaging cells, or producer cells of the present invention given the disclosure provided herein, and standard recombinant techniques (e.g., Sambrook et al, *Molecular Cloning: A Laboratory Manual*, 2d ed., Cold Spring Harbor Laboratory Press, 1989; Kunkle, *PNAS* 82:488, 1985).

Suitable promoters for use in viral vectors generally may include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B 19 parvovirus promoters. The selection of a suitable promoter will be apparent to those skilled in the art from the teachings contained herein, and may be from among either regulated promoters or promoters as described above.

As described above, the retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, 1:5-14 (1990). The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the binding domain-immunoglobulin fusion polypeptides or fusion proteins. Such retroviral vector particles then may be employed, to transduce eukaryotic cells, either in vitro or in vivo. The transduced eukaryotic cells will express the nucleic acid sequence(s) encoding the binding domain-immunoglobulin fusion polypeptide or fusion protein. Eukaryotic cells which may be transduced include, but are not limited to, embryonic stem cells, as well as hematopoietic stem cells, hepatocytes, fibroblasts, circulating peripheral blood mononuclear and polymorphonuclear cells including myelomonocytic cells, lymphocytes, myoblasts, tissue macrophages, dendritic cells, Kupffer cells, lymphoid and reticuloendothelia cells of the lymph nodes and spleen, keratinocytes, endothelial cells, and bronchial epithelial cells.

As another example of an embodiment of the invention in which a viral vector is used to prepare the recombinant binding domain-immunoglobulin fusion expression construct, in one preferred embodiment, host cells transduced by a recombinant viral construct directing the expression of binding domain-immunoglobulin fusion polypeptides or fusion proteins may produce viral particles containing expressed binding domain-immunoglobulin fusion polypeptides or fusion proteins that are derived from portions of a host cell membrane incorporated by the viral particles during viral budding.

In another aspect, the present invention relates to host cells containing the above described recombinant binding domain-immunoglobulin fusion expression constructs. Host cells are genetically engineered (transduced, transformed or transfected) with the vectors and/or expression constructs of this invention which may be, for example, a cloning vector, a shuttle vector or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding binding domain-immunoglobulin fusion polypeptides or binding domain-immunoglobulin fusion proteins. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or 293 cells; adenoviruses; plant cells, or any suitable cell already adapted to in vitro propagation or so established de novo. The selection of an appropriate host is deemed to be within the scope of those skilled in the art from the teachings herein.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of binding domain-immunoglobulin fusion expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, or electroporation (Davis et al., 1986 *Basic Methods in Molecular Biology*).

The present invention binding domain-immunoglobulin fusion proteins may be formulated into pharmaceutical compositions for administration according to well known methodologies. Pharmaceutical compositions generally comprise one or more recombinant expression constructs, and/or expression products of such constructs, in combination with a pharmaceutically acceptable carrier, excipient or diluent. Such carriers will be nontoxic to recipients at the dosages and concentrations employed. For nucleic acid-based formulations, or for formulations comprising expression products of the subject invention recombinant constructs, about 0.01 µg/kg to about 100 mg/kg body weight will be administered, typically by the intradermal, subcutaneous, intramuscular or intravenous route, or by other routes. A preferred dosage is about 1 µg/kg to about 1 mg/kg, with about 5 µg/kg to about 200 µg/kg particularly preferred. It will be evident to those skilled in the art that the number and frequency of administration will be dependent upon the response of the host. "Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

The pharmaceutical compositions that contain one or more binding domain-immunoglobulin fusion protein encoding constructs (or their expressed products) may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intracavernous, intrathecal, intrameatal, intraurethral injection or infusion techniques. The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain, in addition to one or more binding domain-immunoglobulin fusion construct or expressed product, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

It may also be desirable to include other components in the preparation, such as delivery vehicles including but not limited to aluminum salts, water-in-oil emulsions, biodegradable oil vehicles, oil-in-water emulsions, biodegradable microcapsules, and liposomes. Examples of immunostimulatory substances (adjuvants) for use in such vehicles include N-acetylmuramyl-L-alanine-D-isoglutamine (MDP), lipopoly-saccharides (LPS), glucan, IL-12, GM-CSF, gamma interferon and IL-15.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable that the microsphere be larger than approximately 25 microns.

Pharmaceutical compositions may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilizate using appropriate excipient solutions (e.g., sucrose) as diluents.

As described above, the subject invention includes compositions capable of delivering nucleic acid molecules encoding binding domain-immunoglobulin fusion proteins. Such compositions include recombinant viral vectors (e.g., retroviruses (see WO 90/07936, WO 91/02805, WO 93/25234, WO 93/25698, and WO 94/03622), adenovirus (see Berkner, *Biotechniques* 6:616-627, 1988; Li et al., *Hum. Gene Ther.* 4:403-409, 1993; Vincent et al., *Nat. Genet.* 5:130-134, 1993; and Kolls et al., *Proc. Natl. Acad. Sci. USA* 91:215-219, 1994), pox virus (see U.S. Pat. No. 4,769,330; U.S. Pat. No. 5,017,487; and WO 89/01973)), recombinant expression construct nucleic acid molecules complexed to a polycationic molecule (see WO 93/03709), and nucleic acids associated with liposomes (see Wang et al., *Proc. Natl. Acad. Sci. USA* 84:7851, 1987). In certain embodiments, the DNA may be linked to killed or inactivated adenovirus (see Curiel et al., *Hum. Gene Ther.* 3:147-154, 1992; Cotton et al., *Proc. Natl. Acad. Sci. USA* 89:6094, 1992). Other suitable compositions include DNA-ligand (see Wu et al., *J. Biol. Chem.* 264:16985-16987, 1989) and lipid-DNA combinations (see Felgner et al., *Proc. Natl. Acad. Sci. USA* 84:7413-7417, 1989).

In addition to direct in vivo procedures, ex vivo procedures may be used in which cells are removed from a host, modified, and placed into the same or another host animal. It will be evident that one can utilize any of the compositions noted above for introduction of binding domain-immunoglobulin fusion proteins or of binding domain-immunoglobulin fusion protein encoding nucleic acid molecules into tissue cells in an ex vivo context. Protocols for viral, physical and chemical methods of uptake are well known in the art.

Accordingly, the present invention is useful for treating a patient having a B-cell disorder or a malignant condition, or for treating a cell culture derived from such a patient. As used herein, the term "patient" refers to any warm-blooded animal, preferably a human. A patient may be afflicted with cancer, such as B-cell lymphoma, or may be normal (i.e., free of detectable disease and infection). A "cell culture" is any preparation amenable to ex vivo treatment, for example a preparation containing immunocompetent cells or isolated cells of the immune system (including, but not limited to, T cells, macrophages, monocytes, B cells and dendritic cells). Such cells may be isolated by any of a variety of techniques well known to those of ordinary skill in the art (e.g., Ficoll-hypaque density centrifugation). The cells may (but need not) have been isolated from a patient afflicted with a B-cell disorder or a malignancy, and may be reintroduced into a patient after treatment.

A liquid composition intended for either parenteral or oral administration should contain an amount of binding domain-immunoglobulin fusion protein encoding construct or expressed product such that a suitable dosage will be obtained. Typically, this amount is at least 0.01 wt % of a binding domain-immunoglobulin fusion construct or expressed product in the composition. When intended for oral administration, this amount may be varied to be between 0.1 and about 70% of the weight of the composition. Preferred oral compositions contain between about 4% and about 50% of binding domain-immunoglobulin fusion construct or expressed product(s). Preferred compositions and preparations are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the binding domain-immunoglobulin fusion construct or expressed product of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

In the methods of the invention, the binding domain-immunoglobulin fusion encoding constructs or expressed product(s) may be administered through use of insert(s), bead(s), timed-release formulation(s), patch(es) or fast-release formulation(s).

The following Examples are offered by way of illustration and not by way of limitation.

EXAMPLES

Example 1

Cloning of the 2H7 Variable Regions and Construction and Sequencing of 2H7scFv-Ig This Example illustrates the cloning of cDNA molecules that encode the heavy chain and light chain variable regions of the monoclonal antibody 2H7. This Example also demonstrates the construction, sequencing, and expression of 2H7scFv-Ig.

Hybridoma cells expressing 2H7 monoclonal antibody that specifically bound to CD20 were provided by Ed Clark at the University of Washington, Seattle, Wash. Prior to harvesting, hybridoma cells were kept in log phase growth for several days in RPMI 1640 media (Life Technologies, Gaithersburg, Md.) supplemented with glutamine, pyruvate, DMEM non-essential amino acids, and penicillin-streptomycin. Cells were pelleted by centrifugation from the culture medium, and $2 \times 10^7$ cells were used to prepare RNA. RNA was isolated from the 2H7-producing hybridoma cells using the Pharmingen (San Diego, Calif.) total RNA isolation kit (Catalog #45520K) according to the manufacturer's instructions accompanying the kit. One microgram (1 µg) of total RNA was used as template to prepare cDNA by reverse transcription. The RNA and 300 ng random primers were combined and denatured at 72° C. for 10 minutes prior to addition of enzyme. Superscript II reverse transcriptase (Life Technologies) was added to the RNA plus primer mixture in a total volume of 25 µl in the presence of 5× second strand buffer and 0.1 M DTT provided with the enzyme. The reverse transcription reaction was allowed to proceed at 42° C. for one hour.

The 2H7 cDNA generated in the randomly primed reverse transcriptase reaction and V region specific primers were used to amplify by PCR the variable regions for the light and heavy chain of the 2H7 antibody. The V region specific primers were designed using the published sequence (Genbank accession numbers M17954 for $V_L$ and M17953 for $V_H$) as a guide. The two variable chains were designed with compatible end sequences so that an scFv could be assembled by ligation of the two V regions after amplification and restriction enzyme digestion.

A (gly$_4$ser)$_3$ peptide linker to be inserted between the two V regions was incorporated by adding the extra nucleotides to the antisense primer for the V$_L$ of 2H7. A Sac I restriction site was also introduced at the junction between the two V regions. The sense primer used to amplify the 2H7 V$_L$, that included a HindIII restriction site and the light chain leader peptide was 5'-gtc aag ctt gcc gcc atg gat ttt caa gtg cag att ttt cag c-3' (SEQ ID NO:23). The antisense primer was 5'-gtc gtc gag ctc cca cct cct cca gat cca cca ccg ccc gag cca ccg cca cct ttc agc tcc agc ttg gtc cc-3' (SEQ ID NO:24). The reading frame of the V region is indicated as a bold, underlined codon. The Hind III and SacI sites are indicated by underlined italicized sequences.

The V$_H$ domain was amplified without a leader peptide, but included a 5' SacI restriction site for fusion to the V$_L$ and a BclI restriction site at the 3' end for fusion to various tails, including the human IgG1 Fc domain and the truncated forms of CD40 ligand, CD154. The sense primer was 5'-gct gct gag ctc tca ggc tta tct aca gca agt ctg g-3' (SEQ ID NO:25). The SacI site is indicated in italicized and underlined font, and the reading frame of the codon for the first amino acid of the V$_H$ domain is indicated in bold, underlined type. The antisense primer was 5'-gtt gtc tga tca gag acg gtg acc gtg gtc cc-3' (SEQ ID NO:26). The BclI site is indicated in italicized, underlined type, and the last serine of the V$_H$ domain sequence is indicated in bold, underlined type.

The scFv-Ig was assembled by inserting the 2H7 scFv HindIII-BclI fragment into pUC19 containing the human IgG1 hinge, CH2, and CH3 regions, which was digested with restriction enzymes, HindIII and BclI. After ligation, the ligation products were transformed into DH5α bacteria. Positive clones were screened for the properly inserted fragments using the SacI site at the V$_L$-V$_H$ junction of 2H7 as a diagnostic site. The 2H7scFv-Ig cDNA was subjected to cycle sequencing on a PE 9700 thermocycler using a 25-cycle program by denaturing at 96° C. for 10 seconds, annealing at 50° C. for 30 seconds, and extending at 72° C. for 4 minutes. The sequencing primers were pUC forward and reverse primers and an internal primer that annealed to the CH2 domain human in the IgG constant region portion. Sequencing reactions were performed using the Big Dye Terminator Ready Sequencing Mix (PE-Applied Biosystems, Foster City, Calif.) according to the manufacturer's instructions. Samples were subsequently purified using Centrisep columns (Catalog #CS-901, Princeton Separations, Adelphia, N.J.), the eluates dried in a Savant vacuum dryer, denatured in Template Suppression Reagent (PE-ABI), and analyzed on an ABI 310 Genetic Analyzer (PE-Applied Biosystems). The sequence was edited, translated, and analyzed using Vector Nti version 6.0 (Informax, North Bethesda, Md.). FIG. 1 shows the cDNA and predicted amino acid sequence of the 2H7scFv-Ig construct.

Example 2

Expression of 2H7 ScFv-Ig in Stable CHO Cell Lines

This Example illustrates expression of 2H7scFv-Ig in a eukaryotic cell line and characterization of the expressed 2H7scFv-Ig by SDS-PAGE and by functional assays, including ADCC and complement fixation.

The 2H7scFv-Ig HindIII-XbaI (~1.6 kb) fragment with correct sequence was inserted into the mammalian expression vector pD18, and DNA from positive clones was amplified using QIAGEN plasmid preparation kits (QIAGEN, Valencia, Calif.). The recombinant plasmid DNA (100 µg) was then linearized in a nonessential region by digestion with AscI, purified by phenol extraction, and resuspended in tissue culture media, Excell 302 (Catalog #14312-79P, JRH Biosciences, Lenexa, Kans.). Cells for transfection, CHO DG44 cells, were kept in logarithmic growth, and 10$^7$ cells harvested for each transfection reaction. Linearized DNA was added to the CHO cells in a total volume of 0.8 ml for electroporation.

Stable production of the 2H7 scFv-Ig fusion protein (SEQ. ID NO:15) was achieved by electroporation of a selectable, amplifiable plasmid, pD18, containing the 2H7 scFv-Ig cDNA under the control of the CMV promoter, into Chinese Hamster Ovary (CHO) cells (all cell lines from American Type Culture Collection, Manassas, Va., unless otherwise noted). The 2H7 expression cassette was subcloned downstream of the CMV promoter into the vector multiple cloning site as a ~1.6 kb HindIII-XbaI fragment. The pD18 vector is a modified version of pcDNA3 encoding the DHFR selectable marker with an attenuated promoter to increase selection pressure for the plasmid. Plasmid DNA was prepared using Qiagen maxiprep kits, and purified plasmid was linearized at a unique AscI site prior to phenol extraction and ethanol precipitation. Salmon sperm DNA (Sigma-Aldrich, St. Louis, Mo.) was added as carrier DNA, and 100 µg each of plasmid and carrier DNA was used to transfect 10$^7$ CHO DG44 cells by electroporation. Cells were grown to logarithmic phase in Excell 302 media (JRH Biosciences) containing glutamine (4 mM), pyruvate, recombinant insulin, penicillin-streptomycin, and 2× DMEM nonessential amino acids (all from Life Technologies, Gaithersburg, Md.), hereafter referred to as "Excell 302 complete" media. Media for untransfected cells also contained HT (diluted from a 100× solution of hypoxanthine and thymidine) (Life Technologies). Media for transfections under selection contained varying levels of methotrexate (Sigma-Aldrich) as selective agent, ranging from 50 nM to 5 µM. Electroporations were performed at 275 volts, 950 µF. Transfected cells were allowed to recover overnight in non-selective media prior to selective plating in 96 well flat bottom plates (Costar) at varying serial dilutions ranging from 125 cells/well to 2000 cells/well. Culture media for cell cloning was Excell 302 complete, containing 100 nM methotrexate. Once clonal outgrowth was sufficient, serial dilutions of culture supernatants from master wells were screened for binding to CD20-CHO transfected cells. The clones with the highest production of the fusion protein were expanded into T25 and then T75 flasks to provide adequate numbers of cells for freezing and for scaling up production of the 2H7scFvIg. Production levels were further increased in cultures from three clones by progressive amplification in methotrexate containing culture media. At each successive passage of cells, the Excell 302 complete media contained an increased concentration of methotrexate, such that only the cells that amplified the DHFR plasmid could survive.

Supernatants were collected from CHO cells expressing the 2H7scFv-Ig, filtered through 0.2 µm PES express filters (Nalgene, Rochester, N.Y.) and were passed over a Protein A-agarose (IPA 300 crosslinked agarose) column (Repligen, Needham, Mass.). The column was washed with PBS, and then bound protein was eluted using 0.1 M citrate buffer, pH 3.0. Fractions were collected and eluted protein was neutralized using 1M Tris, pH 8.0, prior to dialysis overnight in PBS. Concentration of the purified 2H7scFv-Ig (SEQ ID NO: 15) was determined by absorption at 280 nm. An extinction coefficient of 1.77 was determined using the protein analysis tools in the Vector Nti Version 6.0 Software package (Informax, North Bethesda, Md.). This program uses the amino acid composition data to calculate extinction coefficients.

Production levels of 2H7scFv-Ig by transfected, stable CHO cells were analyzed by flow cytometry. Purified 2H7scFv-Ig to CHO cells was allowed to bind to CHO cells that expressed CD20 (CD20 CHO) and analyzed by flow cytometry using a fluorescein-conjugated anti-human IgG second step reagent (Catalog Numbers H10101 and H10501, CalTag, Burlingame, Calif.). FIG. 2 (top) shows a standard curve generated by titration of 2H7scFv-Ig binding to CD20 CHO. At each concentration of 2H7scFv-Ig, the mean brightness of the fluorescein signal in linear units is shown. Supernatants collected from T flasks containing stable CHO cell clones expressing 2H7scFv-Ig were then allowed to bind to CD20 CHO and the binding was analyzed by flow cytometry. The fluorescein signal generated by 2H7scFv-Ig contained in the supernatants was measured and the 2H7scFv-Ig concentration in the supernatants was calculated from the standard curve (FIG. 2, bottom).

Figure 3:
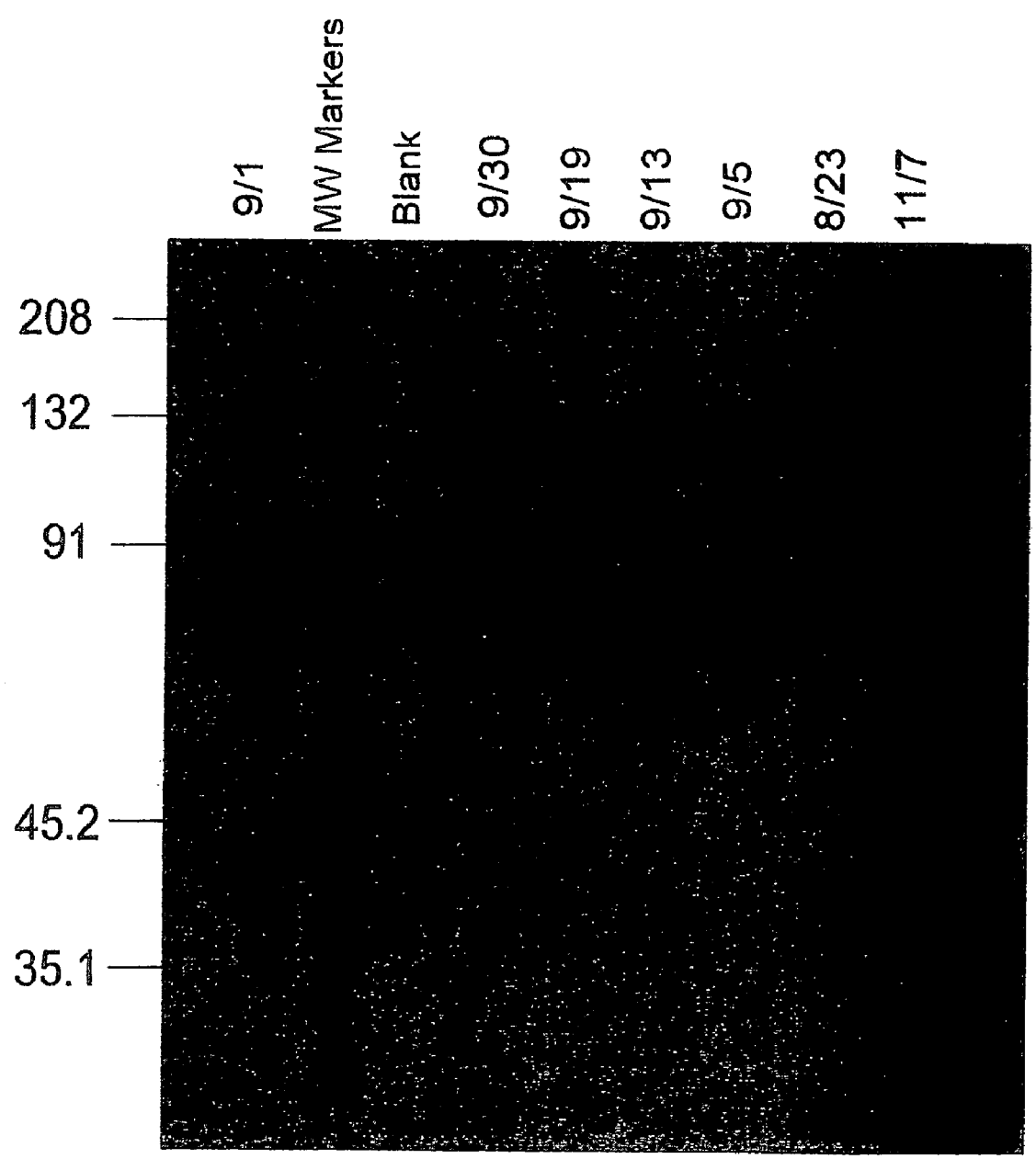
FIG. 3 shows SDS-PAGE analysis of multiple preparations of isolated 2H7scFv-Ig protein.

Purified 2H7scFv-Ig (SEQ ID NO:15) was analyzed by electrophoresis on SDS-Polyacrylamide gels. Samples of 2H7scFv-Ig, purified by independent Protein A Agarose column runs, were boiled in SDS sample buffer without reduction of disulfide bonds and applied to SDS 10% Tris-BIS gels (Catalog #NP0301, Novex, Carlsbad, Calif.). Twenty micrograms of each purified batch was loaded on the gels. The proteins were visualized after electrophoresis by Coomassie Blue staining (Pierce Gel Code Blue Stain Reagent, Catalog #24590, Pierce, Rockford, Ill.), and destaining in distilled water. Molecular weight markers were included on the same gel (Kaleidoscope Prestained Standards, Catalog #161-0324, Bio-Rad, Hercules, Calif.). The results are presented in FIG. 3. The numbers above the lanes designate independent purification batches. The molecular weights in kilodaltons of the size markers are indicated on the left side of the figure. Further experiments with alternative sample preparation conditions indicated that reduction of disulfide bonds by boiling the protein in SDS sample buffer containing DTT or 2-mercaptoethanol caused the 2H7scFv-Ig to aggregate.

Any number of other immunological parameters may be monitored using routine assays that are well known in the art. These may include, for example, antibody dependent cell-mediated cytotoxicity (ADCC) assays, secondary in vitro antibody responses, flow immunocytofluorimetric analysis of various peripheral blood or lymphoid mononuclear cell subpopulations using well established marker antigen systems, immunohistochemistry or other relevant assays. These and other assays may be found, for example, in Rose et al. (Eds.), *Manual of Clinical Laboratory Immunology*, 5th Ed., 1997 American Society of Microbiology, Washington, D.C.

The ability of 2H7scFv-Ig to kill CD20 positive cells in the presence of complement was tested using B cell lines Ramos and Bjab. Rabbit complement (Pel-Freez, Rogers, Ak.) was used in the assay at a final dilution of 1/10. Purified 2H7scFv-Ig was incubated with B cells and complement for 45 minutes at 37° C., followed by counting of live and dead cells by trypan blue exclusion. The results in FIG. 4A show that in the presence of rabbit complement, 2H7scFv-Ig lysed B cells expressing CD20.

The ability of 2H7scFv-Ig to kill CD20 positive cells in the presence of peripheral blood mononuclear cells (PBMC) was tested by measuring the release of $^{51}$Cr from labeled Bjab cells in a 4-hour assay using a 100:1 ratio of PBMC to Bjab cells. The results shown in FIG. 4B indicated that 2H7scFv-Ig can mediate antibody dependent cellular cytotoxicity (ADCC) because the release of $^{51}$Cr was higher in the presence of both PBMC and 2H7scFv-Ig than in the presence of either PBMC or 2H7scFv-Ig alone.

Example 3

Effect of Simultaneous Ligation of CD20 and CD40 on Growth of Normal B Cells, and on CD95 Expression, and Induction of Apoptosis This example illustrates the effect of cross-linking of CD20 and CD40 expressed on the cell surface on cell proliferation.

Dense resting B cells were isolated from human tonsil by a Percoll step gradient and T cells were removed by E-rosetting. Proliferation of resting, dense tonsillar B cells was measured by uptake of $^3$[H]-thymidine during the last 12 hours of a 4-day experiment. Proliferation was measured in quadruplicate cultures with means and standard deviations as shown. Murine anti-human CD20 mAb IF5 (anti-CD20) was used alone or was cross-linked with anti-murine κ mAb 187.1 (anti-CD20XL). CD40 activation was accomplished using soluble human CD154 fused with murine CD8 (CD 154) (Hollenbaugh et al., *EMBO J.* 11: 4212-21 (1992)), and CD40 cross-linking was accomplished using anti-murine CD8 mAb 53-6 (CD154XL). This procedure allowed simultaneous cross-linking of CD20 and CD40 on the cell surface. The results are presented in FIG. 5.

The effect of CD20 and CD40 cross-linking on Ramos cells, a B lymphoma cell line, was examined. Ramos cells were analyzed for CD95 (Fas) expression and percent apoptosis eighteen hours after treatment (no goat anti-mouse IgG (GAM)) and/or cross-linking (+GAM) using murine mAbs that specifically bind CD20 (IF5) and CD40 (G28-5). Control cells were treated with a non-binding isotype control (64.1) specific for CD3.

Treated Ramos cells were harvested, incubated with FITC-anti-CD95, and analyzed by flow cytometry to determine the relative expression level of Fas on the cell surface after CD20 or CD40 cross-linking. Data is plotted as mean fluorescence of cells after treatment with the stimuli indicated (FIG. 6A).

Treated Ramos cells from the same experiment were harvested and binding of annexin V was measured to indicate the percentage apoptosis in the treated cultures. Apoptosis was measured by binding of Annexin V 18 hours after cross-linking of CD20 and CD40 using IF5 and G28-5 followed by cross-linking with GAM. Binding of Annexin V was measured using a FITC-Annexin V kit (Catalog #PN-IM2376, Immunotech, Marseille, France,). Annexin V binding is known to be an early event in progression of cells into apoptosis. Apoptosis, or programmed cell death, is a process characterized by a cascade of catabolic reactions leading to cell death by suicide. In the early phase of apoptosis, before cells change morphology and hydrolyze DNA, the integrity of the cell membrane is maintained but cells lose the asymmetry of their membrane phospholipids, exposing negatively charged phospholipids, such as phosphatidylserine, at the cell surface. Annexin V, a calcium and phopholipid binding protein, binds preferentially and with high affinity to phosphatidylserine. Results demonstrating the effect of cross-linking both CD20 and CD40 on expression of the FAS receptor (CD95) are presented in FIG. 6B. The effect of cross-linking of both CD20 and CD40 on Annexin V binding to cells is shown in FIG. 6B.

Example 4

Construction and Characterization of 2H7 ScFv-CD154 Fusion Proteins

To construct a molecule capable of binding to both CD20 and CD40, cDNA encoding the 2H7 scFv was fused with cDNA encoding CD154, the CD40 ligand. The 2H7 scFv cDNA encoded on the HindIII-BclI fragment was removed from the 2H7 scFvIg construct, and inserted into a pD 18 vector along with a BamHI-XbaI cDNA fragment encoding the extracellular domain of human CD154. The extracellular domain is encoded at the carboxy terminus of CD154, similar to other type II membrane proteins.

The extracellular domain of human CD154 was PCR amplified using cDNA generated with random primers and RNA from human T lymphocytes activated with PHA (phytohemagglutinin). The primer sets included two different 5' or sense primers that created fusion junctions at two different positions within the extracellular domain of CD154. Two different fusion junctions were designed that resulted in a short or truncated form (form S4) including amino acids 108 (Glu)-261 (Leu)+(Glu), and a long or complete form (form L2) including amino acids 48 (Arg)-261 (Leu)+(Glu), of the extracellular domain of CD154, both constructed as BamHI-XbaI fragments. The sense primer which fuses the two different truncated extracellular domains to the 2H7scFv includes a BamHI site for cloning. The sense primer for the S4 form of the CD154 cDNA is designated SEQUENCE ID NO:27 or CD154BAM108 and encodes a 34 mer with the following sequence: 5'-gtt gtc gga tcc aga aaa cag ctt tga aat gca a-3', while the antisense primer is designated SEQUENCE ID NO:28 or CD154XBA and encodes a 44 mer with the following sequence: 5'-gtt gtt tct aga tta tca ctc gag ttt gag taa gcc aaa gga cg-3'.

The oligonucleotide primers used in amplifying the long form (L2) of the CD154 extracellular domain encoding amino acids 48 (Arg)-261 (Leu) +(Glu), were as follows: The sense primer designated CD154 BAM48 (SEQUENCE ID NO:29) encoded a 35-mer with the following sequence: 5'-gtt gtc gga tcc aag aag gtt gga caa gat aga ag-3'. The antisense primer designated CD1 54XBA (SEQUENCE ID NO:28) encoded the 44-mer: 5'-gtt gtt tct aga tta tca ctc gag ttt gag taa gcc aaa gga cg-3'. Other PCR reaction conditions were identical to those used for amplifying the 2H7 scFv (see Example 1). PCR fragments were purified by PCR quick kits (QIAGEN, San Diego, Calif.), eluted in 30 µl ddH$_2$O, and digested with BamHI and XbaI (Roche) restriction endonucleases in a 40 µl reaction volume at 37° C. for 3 hours. Fragments were gel purified, purified using QIAEX kits according to the manufacturer's instructions (QIAGEN), and ligated along with the 2H7 HindIII-BclI fragment into the pD18 expression vector digested with HindIII+XbaI. Ligation reactions were transformed into DH5-alpha chemically competent bacteria and plated onto LB plates containing 100 µg/ml ampicillin. Transformants were grown overnight at 37° C., and isolated colonies used to inoculate 3 ml liquid cultures in Luria Broth containing 100 µg/ml ampicillin. Clones were screened after mini-plasmid preparations (QIAGEN) for insertion of both the 2H7 scFv and the CD154 extracellular domain fragments.

The 2H7scFv-CD154 construct cDNAs were subjected to cycle sequencing on a PE 9700 thermocycler using a 25-cycle program that included denaturating at 96° C., 10 seconds, annealing at 50° C. for 5 seconds, and extension at 60° C., for 4 minutes. The sequencing primers used were pD18 forward (SEQ ID NO:30: 5'-gtctatataagcagagctctggc-3') and pD18 reverse (SEQ ID NO:31: 5'-cgaggctgatcagcgagctctagca-3') primers. In addition, an internal primer was used that had homology to the human CD154 sequence (SEQ ID NO:32: 5'-ccgcaatttgaggattctgatcacc-3'). Sequencing reactions included primers at 3.2 pmol, approximately 200 ng DNA template, and 8 µl sequencing mix. Sequencing reactions were performed using the Big Dye Terminator Ready Sequencing Mix (PE-Applied Biosystems, Foster City, Calif.) according to the manufacturer's instructions. Samples were subsequently purified using Centrisep columns (Princeton Separations, Adelphia, N.J.). The eluates were dried in a Savant speed-vacuum dryer, denatured in 20 µl template Suppression Reagent (ABI) at 95° C. for 2 minutes, and analyzed on an ABI 310 Genetic Analyzer (PE-Applied Biosystems). The sequence was edited, translated, and analyzed using Vector Nti version 6.0 (Informax, North Bethesda, Md.). The 2H7scFv-CD154 L2 cDNA sequence and predicted amino acid sequence is presented in FIG. 7A, and 2H7scFv-CD154 S4 cDNA sequence and predicted amino acid sequence is presented in FIG. 7B.

Figure 8:
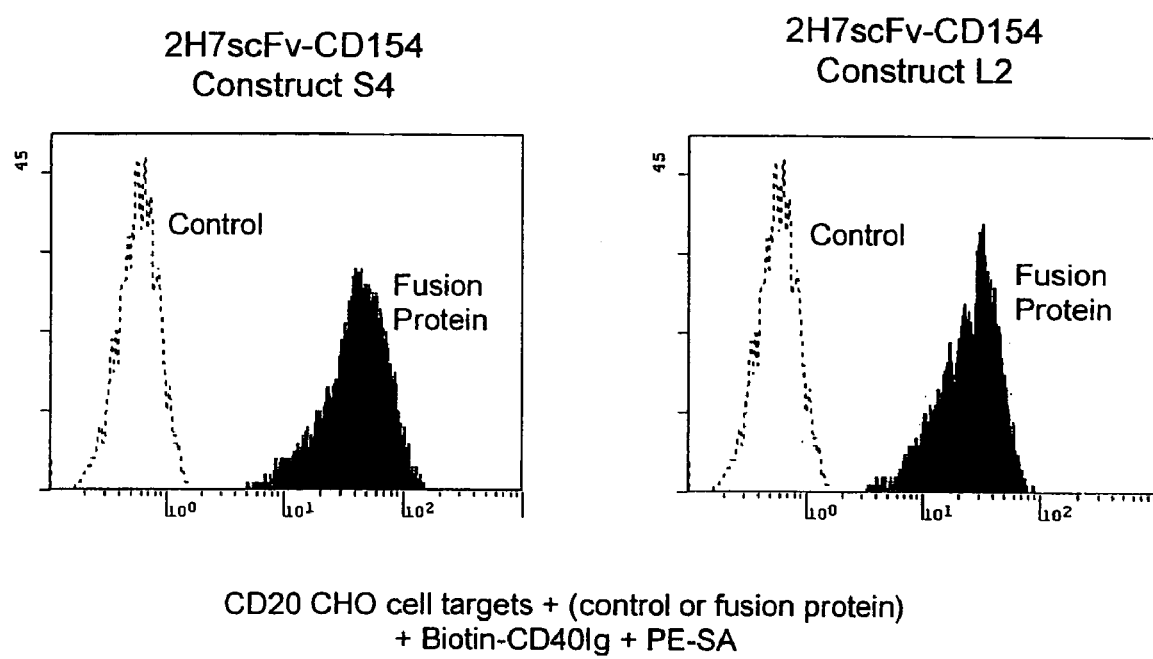
FIG. 8 shows binding of 2H7scFv-CD154 binding domain-immunoglobulin fusion proteins to CD20+ CHO cells by flow immunocytofluorimetry.

The binding activity of the 2H7 scFv-CD154 fusion proteins (SEQ ID NO:33 and 34) to CD20 and CD40 simultaneously was determined by flow cytometry. The assay used CHO cell targets that express CD20. After a 45-minute incubation of CD20 CHO cells with supernatants from cells transfected with the 2H7 scFv-CD154 expression plasmid, the CD20 CHO cells were washed twice and incubated with biotin-conjugated CD40-Ig fusion protein in PBS/2% FBS. After 45 min, cells were washed twice and incubated with phycoerythrin (PE)-labeled strepavidin at 1:100 in PBS/2% FBS (Molecular Probes, Eugene OR). After an additional 30 min incubation, cells were washed 2× and were analyzed by flow cytometry. The results show that the 2H7 scFv-CD 154 molecule was able to bind to CD20 on the cell surface and to capture biotin-conjugated CD40 from solution (FIG. 8).

Figure 9:
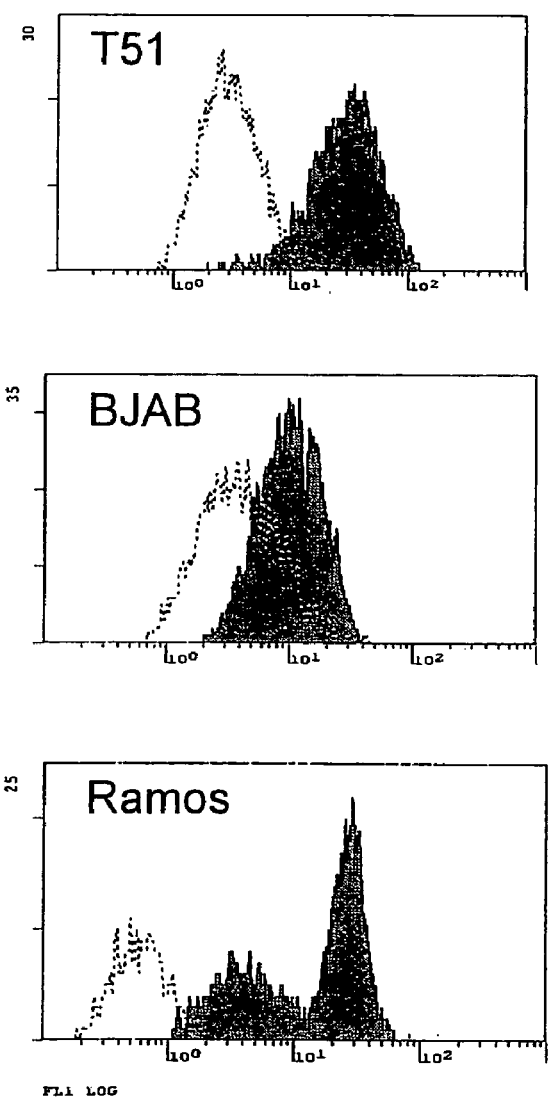
FIG. 9 shows binding of Annexin V to B cell lines Ramos, BJAB, and T51 after binding of 2H7scFv-CD154 binding domain-immunoglobulin fusion protein to cells.

To determine the effect of the 2H7scFv-CD154 on growth and viability of B lymphoma and lymphoblastoid cell lines, cells were incubated with 2H7scFv-CD154 L2 (SEQ. ID NO:33) for 12 hours and then examined for binding of Annexin V. Binding of Annexin V was measured using a FITC-Annexin V kit (Immunotech, Marseille, France, Catalog #PN-IM2376). B cell lines were incubated in 1 ml cultures with dilutions of concentrated, dialyzed supernatants from cells expressing secreted forms of the 2H7scFv-CD 154 fusion proteins. The results are presented in FIG. 9.

Figure 10:
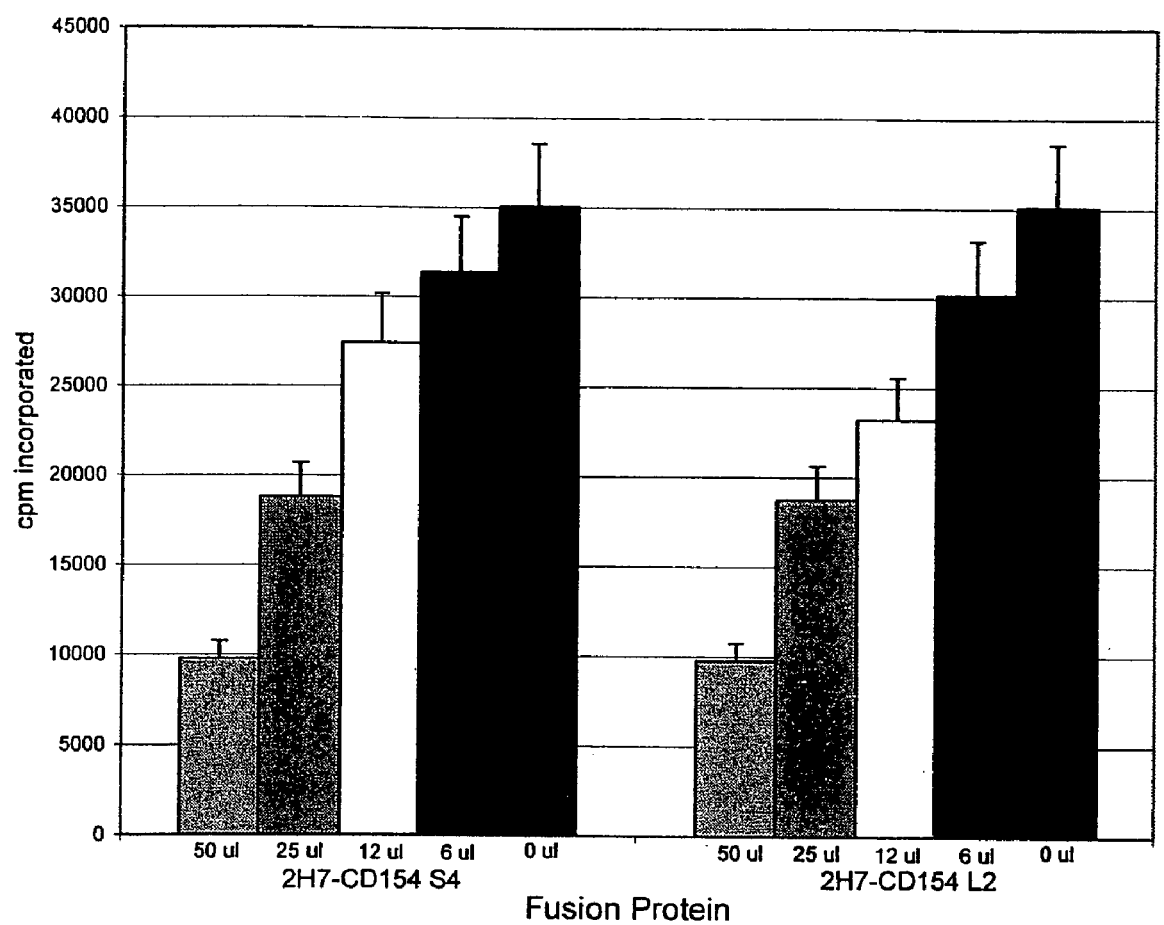
FIG. 10 shows effects on proliferation of B cell line T51 following binding of 2H7scFv-CD154 binding domain-immunoglobulin fusion protein.

The growth rate of the Ramos B lymphoma cell line in the presence of 2H7scFv-CD154 was examined by uptake of $^3$H-thymidine for the last 6 hours of a 24-hour culture. The effect of 2H7scFv-CD 154 on cell proliferation is shown in FIG. 10.

Example 5

Construction and Characterization of CytoxB Antibody Derivatives

CytoxB antibodies were derived from the 2H7 scFv-IgG polypeptide. The 2H7 scFv (see Example 1) was linked to the human IgG1 Fc domain via an altered hinge domain (see FIG. 11). Cysteine residues in the hinge region were substituted with serine residues by site-directed mutagenesis and other methods known in the art. The mutant hinge was fused either to a wild-type Fc domain to create one construct, designated CytoB-MHWTG1C, or was fused to a mutated Fc domain (CytoxB-MHMG1C) that had additional mutations introduced into the CH2 domain. Amino acid residues in CH2 that are implicated in effector function are illustrated in FIG. 11. Mutations of one or more of these residues may reduce FcR binding and mediation of effector functions. In this example, the leucine residue 234 known in the art to be important to Fc receptor binding, was mutated in the 2H7 scFv fusion protein, CytoxB-[MG1H/MG1C]. In another construct, the human IgG1 hinge region was substituted with a portion of the human IgA hinge, which was fused to wild-type human Fc domain (CytoxB-IgAHWTHG1C). (See FIG. 11). This mutated hinge region allows expression of a mixture of monomeric and dimeric molecules that retain functional properties of the human IgG1 CH2 and CH3 domains. Synthetic, recombinant cDNA expression cassettes for these molecules were constructed and polypeptides were expressed in CHODG44 cells according to methods described in Example 2.

Figure 12:
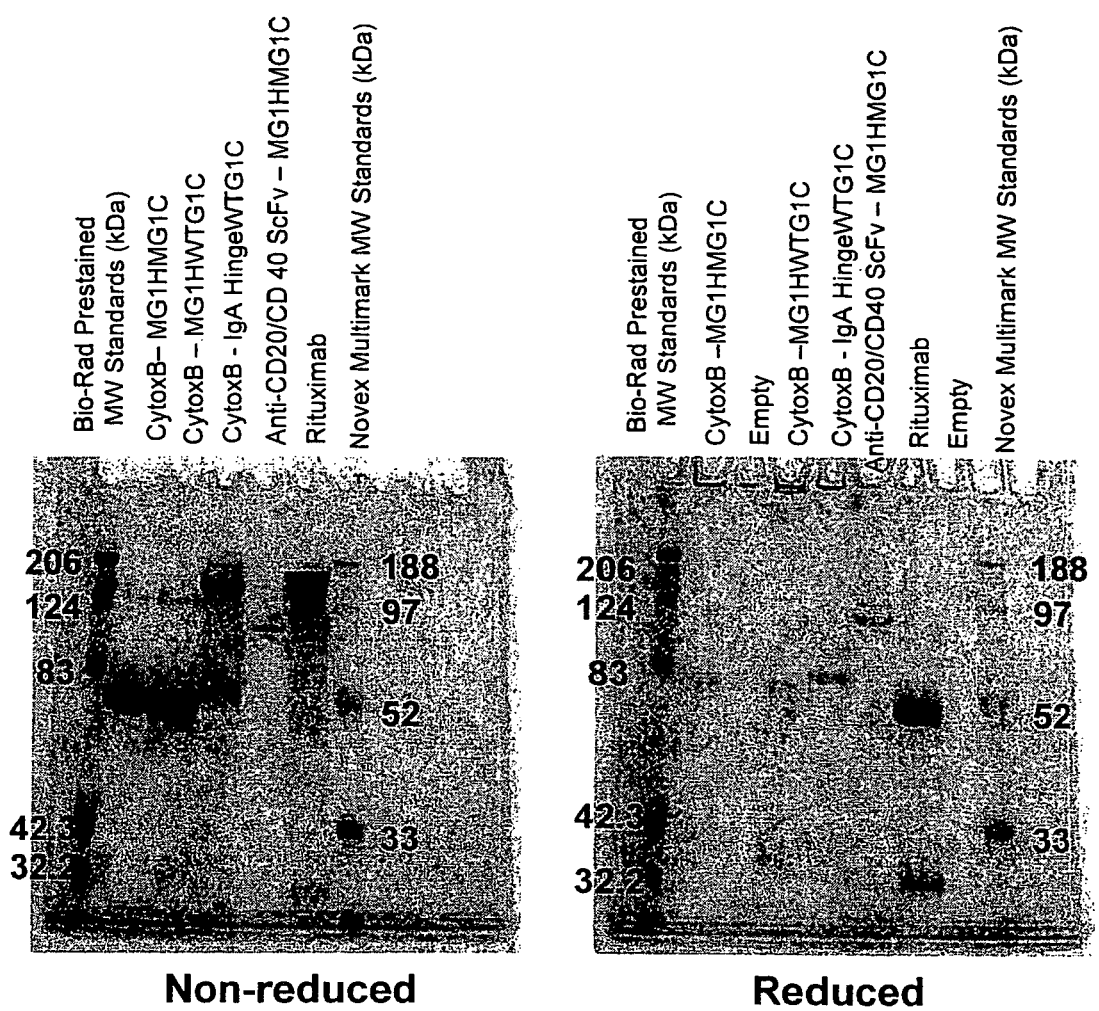
FIG. 12 shows SDS-PAGE analysis of isolated CytoxB and 2H7scFv-CD154 binding domain-immunoglobulin fusion proteins.

Purified fusion protein derivatives of CytoxB-scFvIg molecules were analyzed by SDS-PAGE according to the methods described in Example 2. Polyacrylamide gels were run under non-reducing and reducing conditions. Two different molecule weight marker sets, BioRad prestained markers, (BioRad, Hercules, Calif.) and Novex Multimark molecular weight markers were loaded onto each gel. The migration patterns of the different constructs and of Rituximab™ are presented in FIG. 12.

Figure 13:
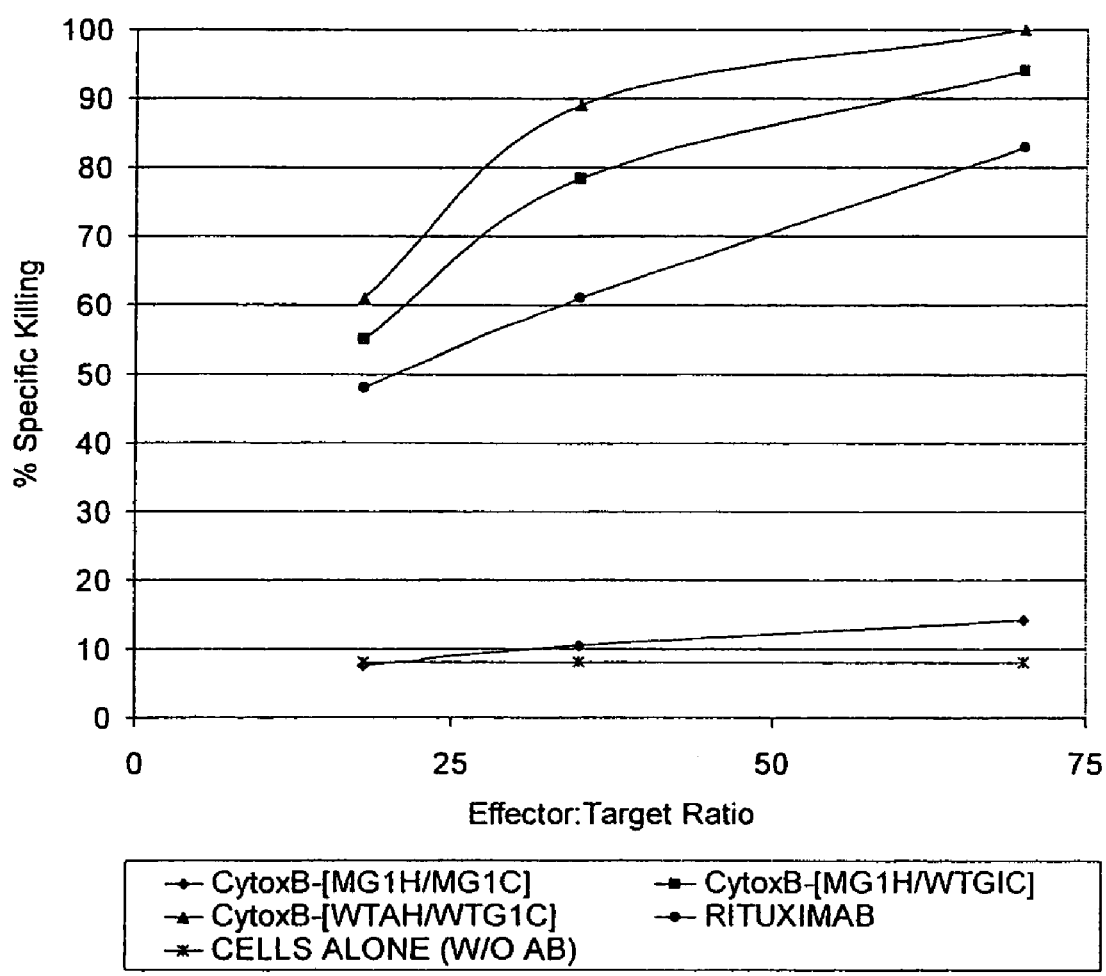
FIG. 13 shows antibody dependent cell-mediated cytotoxicity (ADCC) activity of CytoxB derivatives.

The ability of the different derivatives of CytoxB-scFvIg molecules to mediate ADCC was measured using the Bjab B lymphoma cells as the target and freshly prepared human PBMCs as effector cells. (See Example 2). Effector to target ratios were varied as follows: 70:1, 35:1, and 18:1, with the number of Bjab cells per well remaining constant but the number of PBMCs were varied. Bjab cells were labeled for 2 hours with $^{51}$Cr and aliquoted at a cell density of $5\times10^4$ cells/well to each well of flat-bottom 96 well plates. Purified fusion proteins or rituximab were added at a concentration of 10 mg/ml to the various dilutions of PBMCs. Spontaneous release was measured without addition of PBMC or fusion protein, and maximal release was measured by the addition of detergent (1% NP-40) to the appropriate wells. Reactions were incubated for 4 hours, and 100 μl of culture supernatant was harvested to a Lumaplate (Packard Instruments) and allowed to dry overnight prior to counting cpm released. The results are presented in FIG. 13.

Figure 14:
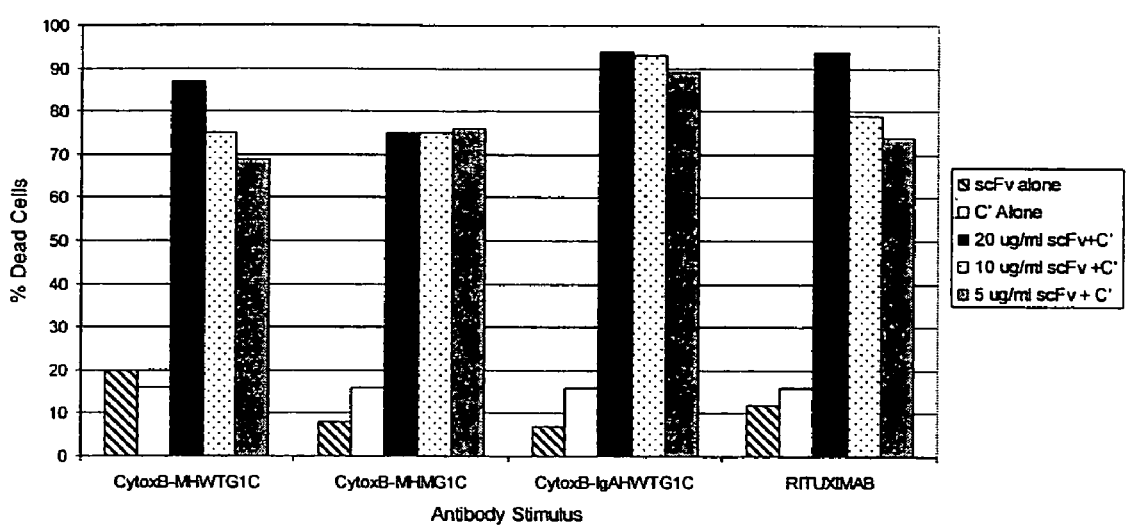
FIG. 14 shows complement dependent cytotoxicity (CDC) of CytoxB derivatives.

Complement dependent cytotoxicity (CDC) activity of the CytoxB derivatives was also measured. Reactions were performed essentially as described in Example 2. The results are presented in FIG. 14 as percent of dead cells to total cells for each concentration of fusion protein.

Example 6

In Vivo Studies in Macaques

Figure 15:
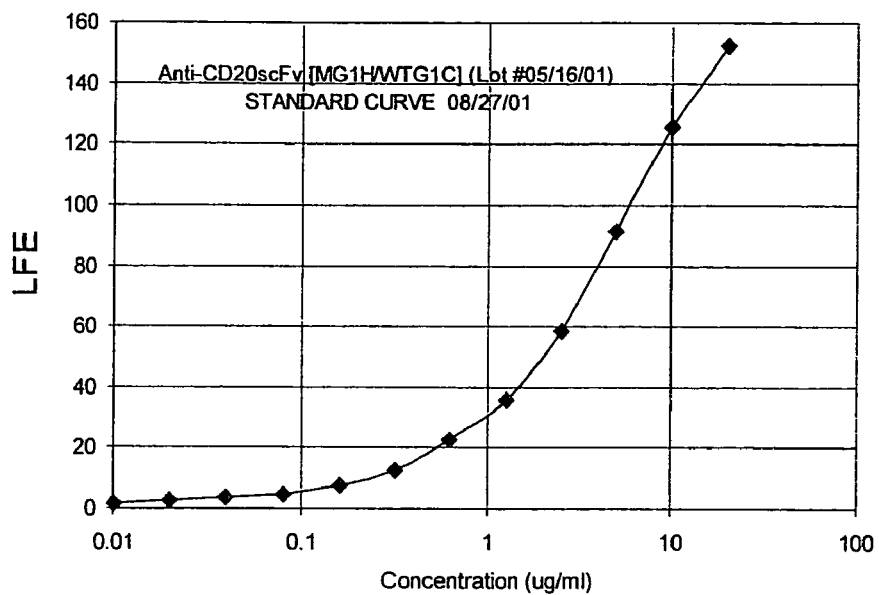
FIG. 15 shows serum half-life determinations of CytoxB-MHWTG1C in macaque blood samples.

Initial in vivo studies with CytoxB derivatives have been performed in nonhuman primates. FIG. 15 shows data characterizing the serum half-life of CytoxB in monkeys. Measurements were performed on serum samples obtained from two different macaques (J99231 and K99334) after doses of 6 mg/kg were administered to each monkey on the days indicated by arrows. For each sample, the level of 2H7scFvIg present was estimated by comparison to a standard curve generated by binding of purified CytoxB-(MHWTG1C)-Ig fusion protein to CD20 CHO cells (see Example 2). The data are tabulated in the bottom panel of the FIG. 15.

Figure 16:
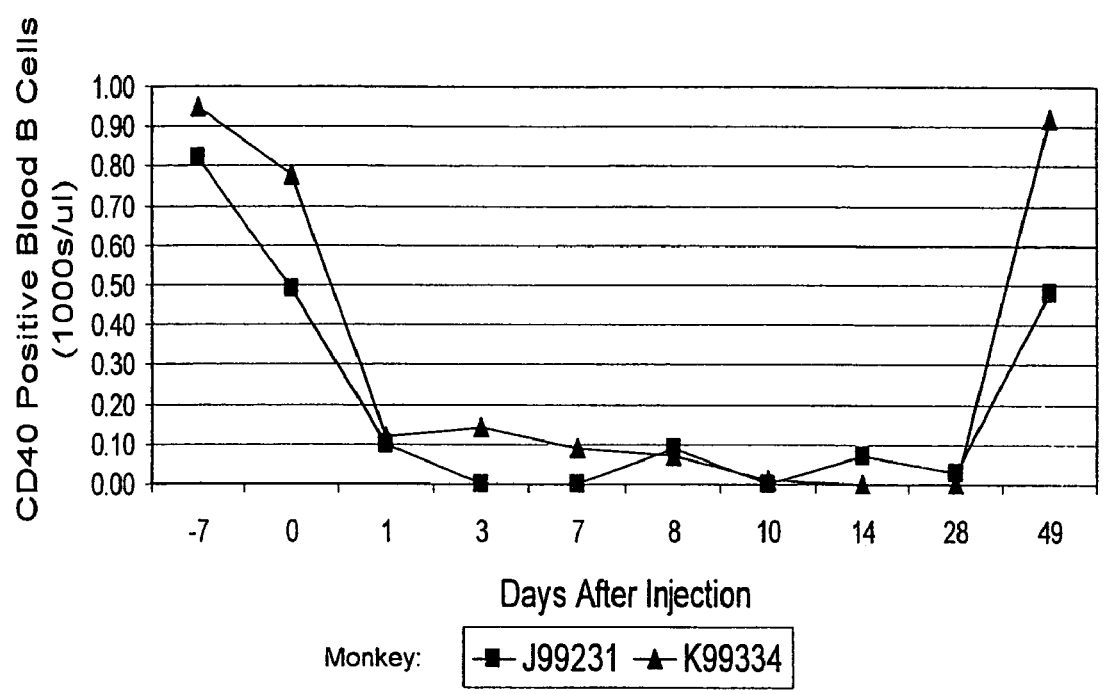
FIG. 16 shows effects of CytoxB-MHWTG1C on levels of circulating CD40+ B cells in macaque blood samples.

The effect of CytoxB-(MHWTG1C)Ig fusion protein on levels of circulating CD40+ cells in macaques was investigated. Complete blood counts were performed at each of the days indicated in FIG. 16. In addition, FACS (fluorescence activated cell sorter) assays were performed on peripheral blood lymphocytes using a CD40-specific fluorescein conjugated antibody to detect B cells among the cell population. The percentage of positive cells was then used to calculate the number of B cells in the original samples. The data are graphed as thousands of B cells per microliter of blood measured at the days indicated after injection (FIG. 16).

Example 7

Construction and Expression of an Anti-CD19 scFv-Ig Fusion Protein

Figure 17:
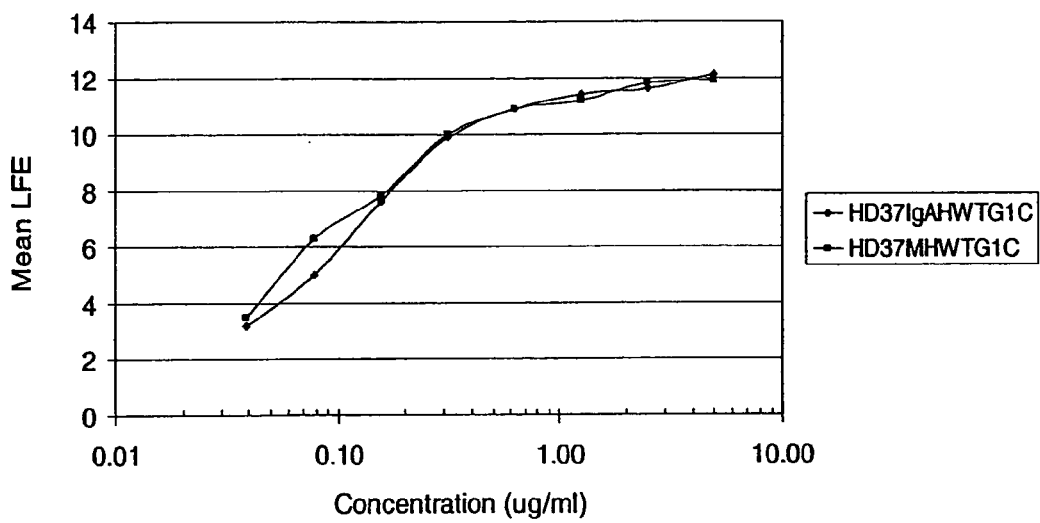
FIG. 17 shows production levels of HD37 (CD19-specific) ScFv-Ig by transfected mammalian cell lines and generation of a standard curve by binding of purified HD37 ScFv-Ig to cells expressing CD19.

An anti-CD19 scFv-Ig fusion protein was constructed, transfected into eukaryotic cells, and expressed according to methods presented in Examples 1, 2, and 5 and standard in the art. The variable heavy chain regions and variable light chain regions were cloned from RNA isolated from hybridoma cells producing antibody HD37, which specifically binds to CD19. Expression levels of a HD37scFv-IgAHWTG1C and a HD37scFv-IgMHWTG1C were measured and compared to a standard curve generated using purified HD37 scFvIg. The results are presented in FIG. 17.

Example 8

Construction and Expression of an Anti-L6 scFv-Ig Fusion Protein

Figure 18:
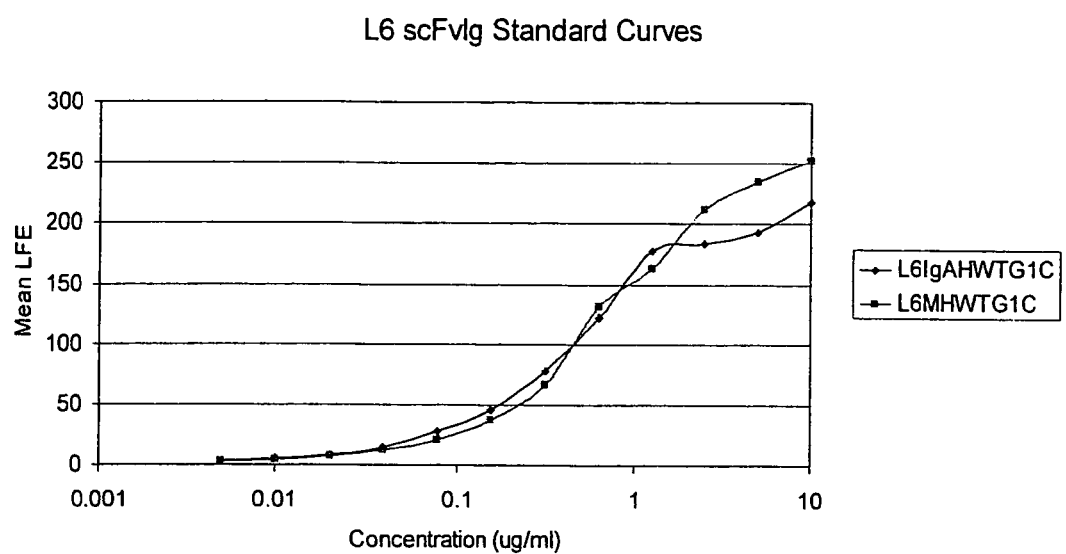
FIG. 18 shows production levels of L6 (carcinoma antigen) ScFv-Ig by transfected, stable CHO lines and generation of a standard curve by binding of purified L6 ScFv-Ig to cells expressing L6 antigen.

An scFv-Ig fusion protein was constructed using variable regions derived from an anti-carcinoma mAb, L6. The fusion protein was constructed, transfected into eukaryotic cells, and expressed according to methods presented in Examples 1, 2, and 5 and standard in the art. Expression levels of L6scFv-IgAHWTG1C and L6scFv-IgMHWTG1C were measured and compared to a standard curve generated using purified HD37 scFvIg. The results are presented in FIG. 18.

Example 9

Characterization of Various scFv-Ig Fusion Proteins

Figure 19A:
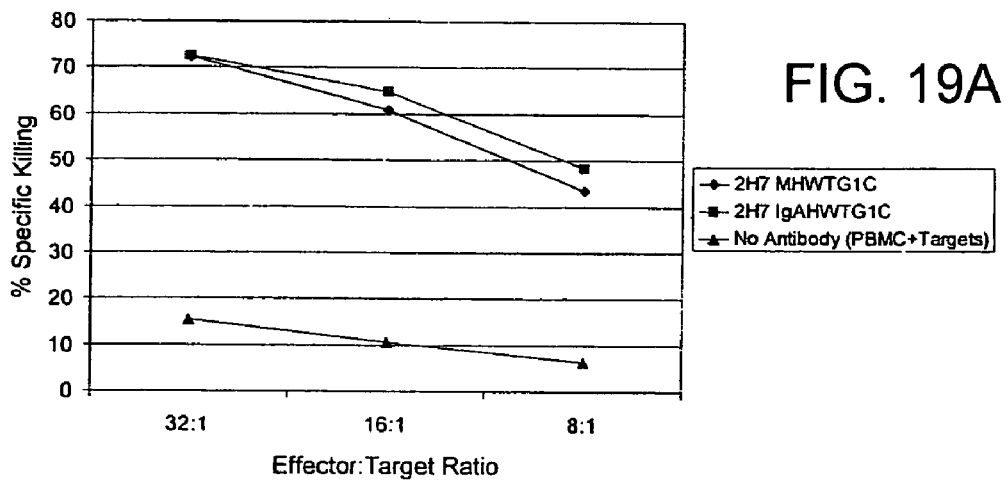
FIGS. 19A-19C show ADCC activity of binding domain-immunoglobulin fusion proteins 2H7 ScFv-Ig (19A), HD37 ScFv-Ig (19C) and G28-1 (CD37-specific) ScFv-Ig (19B).
Figure 19B:
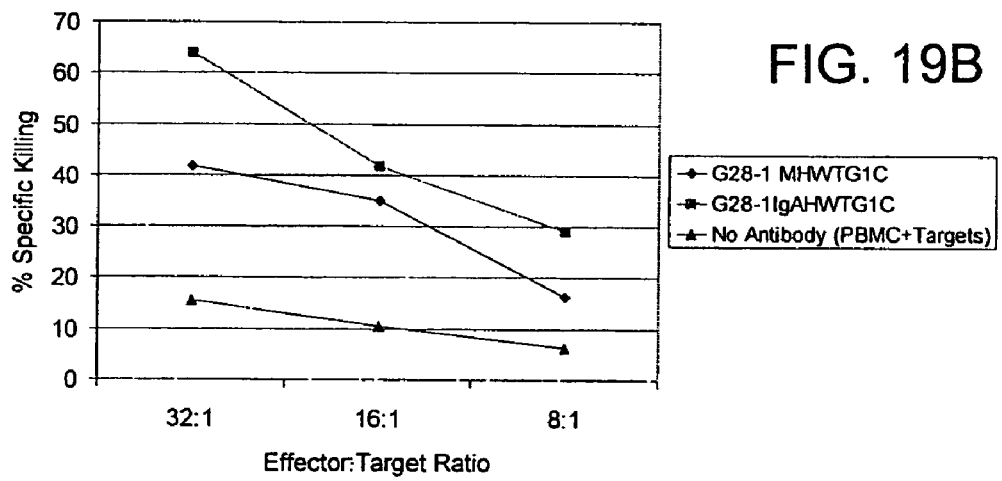
Figure 19C:
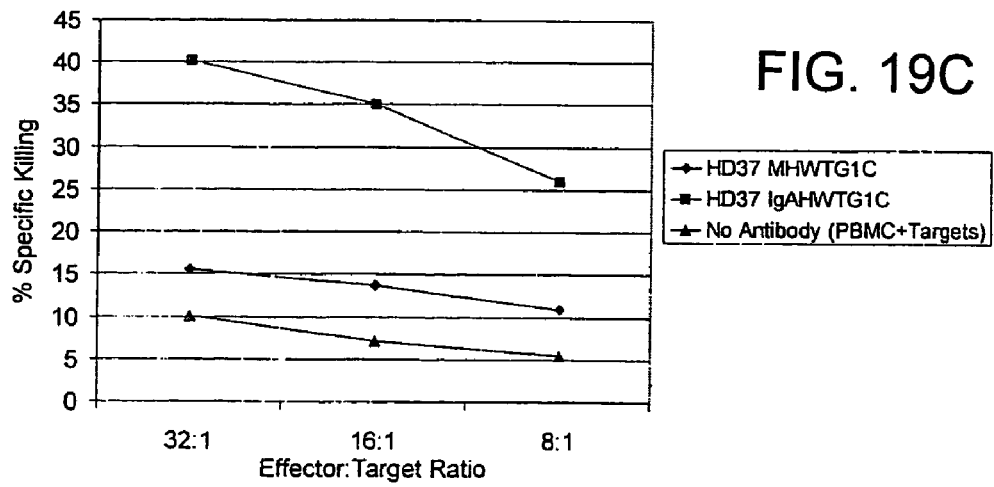
Figure 20:
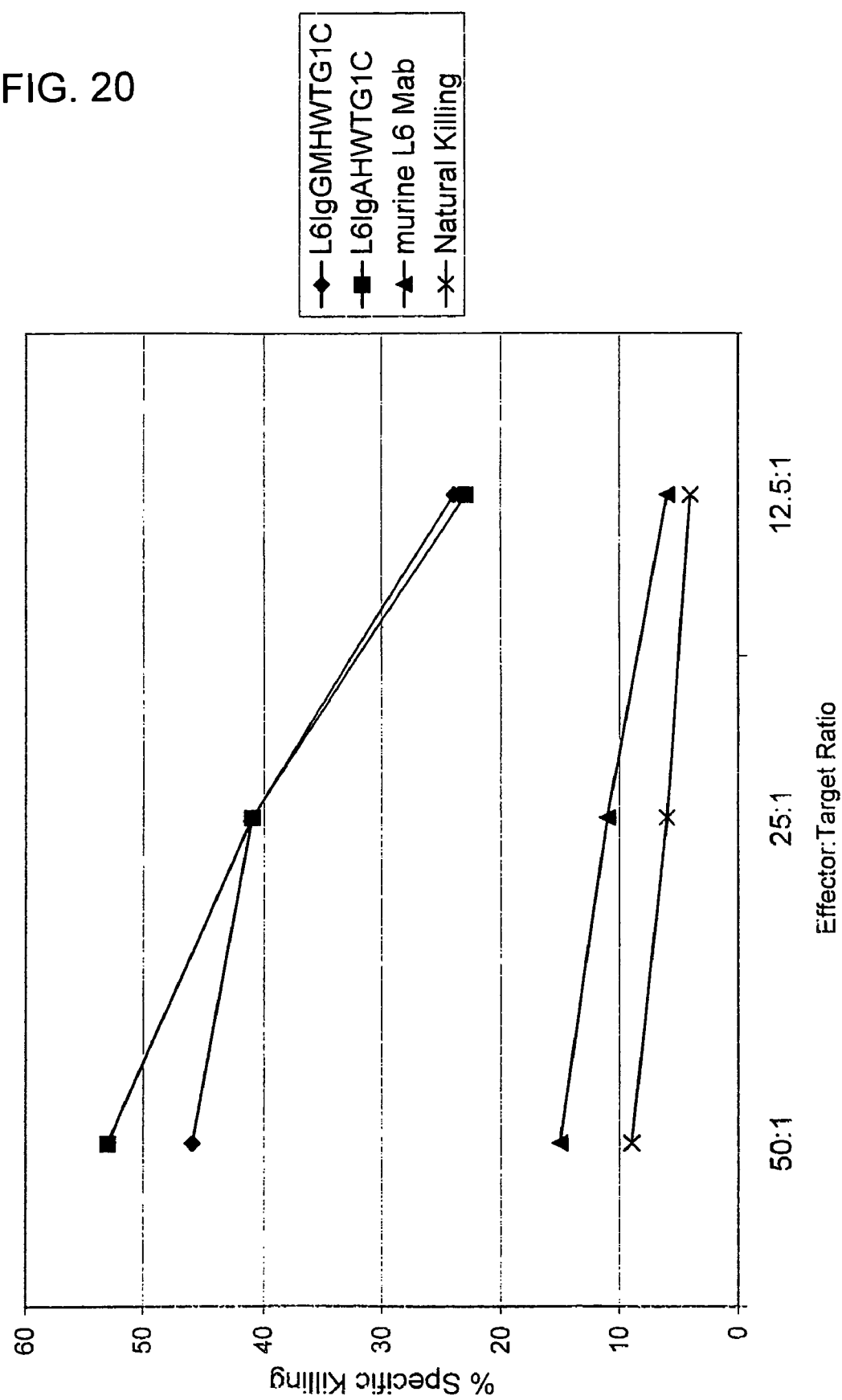
FIG. 20 shows ADCC activity of L6 ScFv-Ig fusion proteins.

In addition to the scFv-Ig fusion protein already described, G28-1 (anti-CD37) scFv-Ig fusion proteins were prepared essentially as described in Examples 1 and 5. The variable regions of the heavy and light chains were cloned according to methods known in the art. ADCC activity of 2H7-MHWTG1C, 2H7-IgAHWTG1C, G28-1-MHWTG1C, G28-1 IgAHWTG1C, HD37-MHWTG1C, and HD37-IgAHWTG1C was determined according to methods described above (see Example 2). Results are presented in FIG. 19. ADCC activity of L6scFv-IgAHWTG1C and L6scFv-IgMHWTG1C was measured using the 2981 human lung carcinoma cell line. The results are presented in FIG. 20. The murine L6 monoclonal antibody is known not to exhibit ADCC activity.

Figure 21:
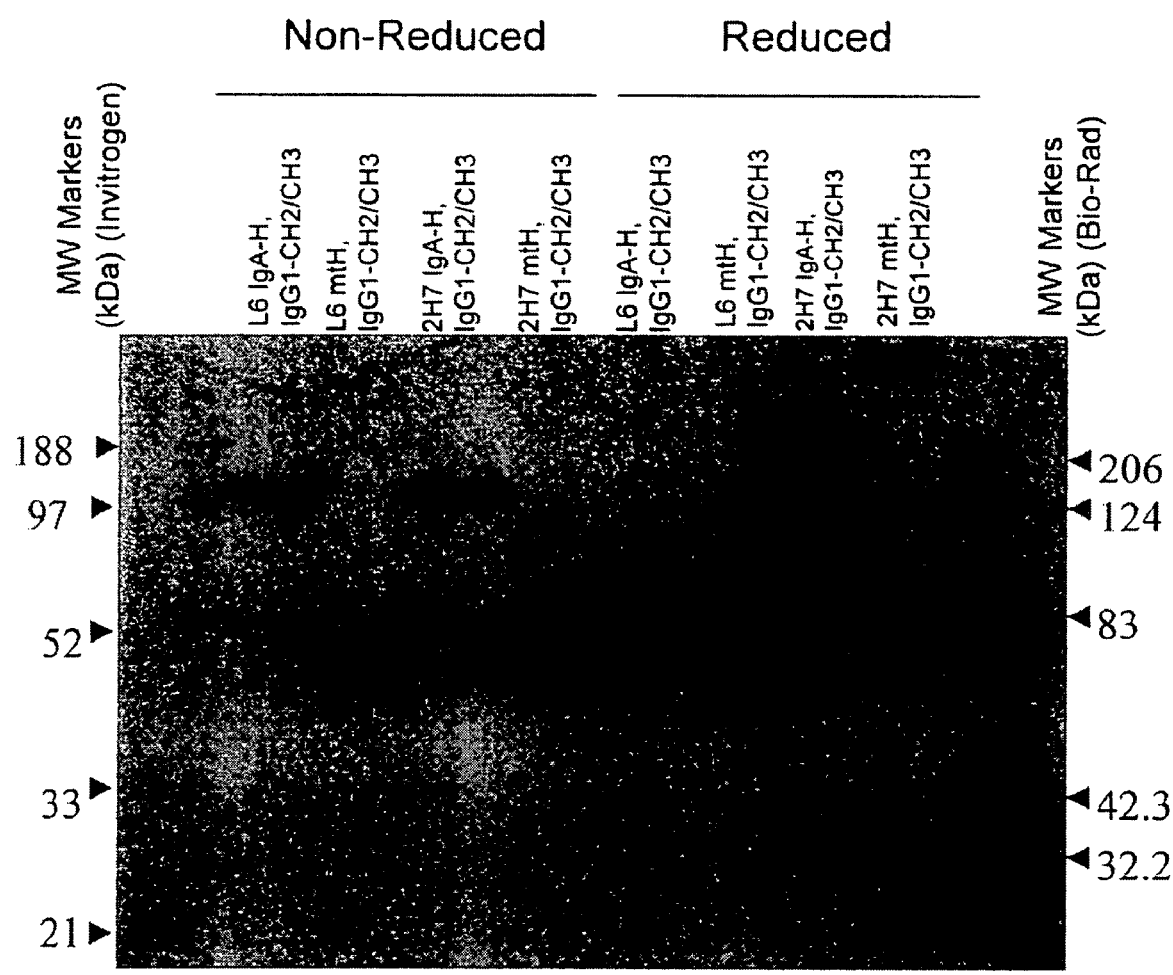
FIG. 21 shows SDS-PAGE analysis of L6 ScFv-Ig and 2H7 ScFv-Ig fusion proteins.
Figure 22:
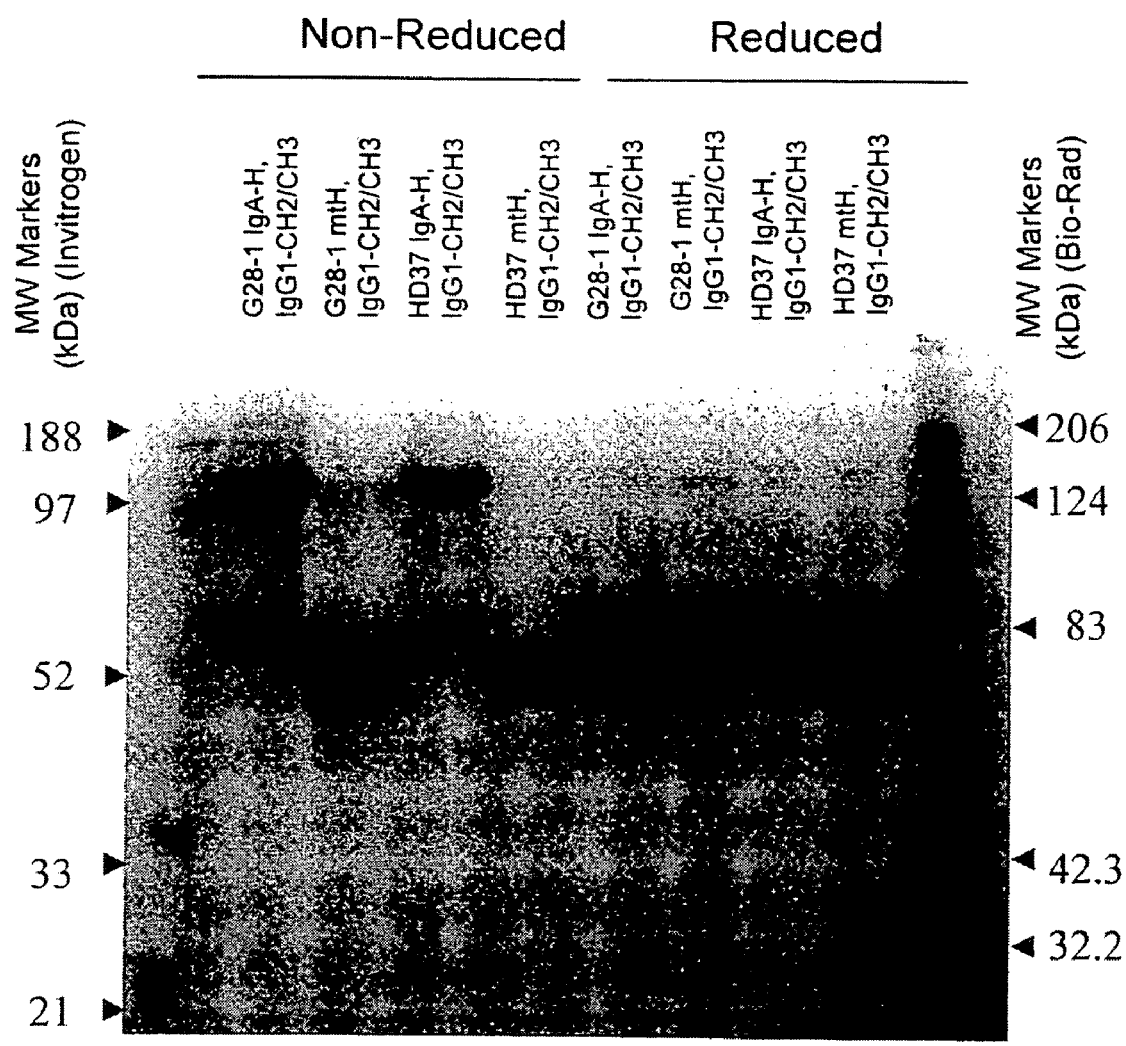
FIG. 22 shows SDS-PAGE analysis of G28-1 ScFv-Ig and HD37 ScFv-Ig fusion proteins.

The purified proteins were analyzed by SDS-PAGE under reducing and non-reducing conditions. Samples were prepared and gels run essentially as described in Examples 2 and 5. The results for the L6 and 2H7 scFv-Ig fusion proteins are presented in FIG. 21 and the results for the G28-1 and HD37 scFv-Ig fusion proteins are presented in FIG. 22.

From the foregoing, it will be appreciated that, although specific embodiments of the invention have been described herein for the purpose of illustration, various modifications may be made without deviating from the spirit and scope of the invention. Accordingly, the present invention is not limited except as by the appended claims.

What is claimed is:

1. A pharmaceutical composition comprising a pharmaceutically acceptable carrier and a therapeutically effective amount of a single chain protein that binds to a target biological molecule, wherein said single chain protein comprises:
   (a) an immunoglobulin binding domain polypeptide that binds said target, said binding domain polypeptide being joined to
   (b) a hinge peptide, hinge peptide being joined to
   (c) an immunoglobulin heavy chain CH2 constant region polypeptide, said CH2 constant region polypeptide being joined to
   (d) an immunoglobulin heavy chain CH3 constant region polypeptide,
   wherein said hinge peptide is an IgG1 hinge peptide in which the number of cysteines is one.

2. The pharmaceutical composition of claim 1 wherein the target biological molecule is on the surface of a target cell, and said single chain protein binds to said target and decreases the number of target cells.

3. The pharmaceutical composition of claim 1 wherein said binding domain polypeptide is a single chain Fv polypeptide.

4. The pharmaceutical composition of claim 1, wherein said single chain protein is capable of binding to a B cell target.

5. The pharmaceutical composition of claim 4, wherein said B cell target is CD20.

6. The pharmaceutical composition of claim 4, wherein said B cell target is CD37.

7. The pharmaceutical composition of claim 1 or 3, wherein said target is selected from the group consisting of CD19, CD22, CD30 ligand, CD54, CD106, and interleukin-12.

8. The pharmaceutical composition of claim 1, 3, 4, 5 or 6, wherein said single chain protein is capable of depleting a population of target cells.

9. The pharmaceutical composition of claim 1, 3, 4, 5 or 6, wherein said single chain protein is capable of decreasing the number of target cells in vivo.

10. The pharmaceutical composition of claim 1, 3, 4, 5 or 6, wherein said single chain protein is capable of decreasing the number of target cells in vitro.

11. The pharmaceutical composition of claim 3, wherein the heavy and light chain variable regions of the single chain Fv are joined by a polypeptide linker of about 5 amino acids to about 15 amino acids.

12. The pharmaceutical composition of claim 11 wherein said single chain Fv polypeptide is capable of binding to a target selected from the group consisting of CD2, CD5, CD10, CD27, CD28, CD40, CTLA-4, 4-1BB, 4-1BB ligand, interferon-γ, interleukin-4, and interleukin-17.

13. The pharmaceutical composition of claim 11 wherein said single chain Fv polypeptide is capable of binding to a target selected from the group consisting of CD59, CD48, CD72, CD70, CD86/B7.2, CD40 ligand, CD43 and VLA-4 ($\alpha_4\beta_7$).

14. The pharmaceutical composition of claim 11 wherein said single chain Fv polypeptide is capable of binding to a target selected from the group consisting of CD83 and DEC-205.

15. The pharmaceutical composition of claim 11 wherein said single chain Fv polypeptide is capable of binding to a target selected from the group consisting of HER1, HER2, HER3, HER4, vascular endothelial cell growth factor, insulin-like growth factor-I, insulin-like growth factor-II, MUC-1, NY-ESO-1, NA 17-A, Melan-A/MART-1, tyrosinase, Gp-100, MAGE, BAGE, GAGE, the HOM-MEL-40 antigen encoded by the SSX2 gene, carcinoembyonic antigen, and PyLT.

16. The pharmaceutical composition of claim 11, wherein said single chain Fv polypeptide is capable of binding to an interleukin-17 receptor, an epidermal growth factor receptor, a vascular endothelial cell growth factor receptor, a transferrin receptor, an estrogen receptor, a progesterone receptor, a follicle stimulating hormone receptor, a retinoic acid receptor, or any of the CTA class receptors.

17. The pharmaceutical composition of claim 4 wherein said binding domain polypeptide is a single chain Fv capable of binding human CD20, and said immunoglobulin heavy chain CH2 and CH3 constant region polypeptides are IgG1 CH2 and CH3 constant region polypeptides.

18. The pharmaceutical composition of claim 17, wherein said single chain protein includes a 2H7 single chain Fv binding domain polypeptide.

19. The pharmaceutical composition of claim 17, wherein said heavy chain constant region comprises a CH2 domain in which a leucine has been replaced with serine at position 234.

20. The pharmaceutical composition of claim 4 wherein said binding domain polypeptide is an single chain Fv capable of binding a human CD37, and said immunoglobulin heavy chain CH2 and CH3 constant region polypeptides are IgG1 CH2 and CH3 constant region polypeptides.

21. The pharmaceutical composition of claim 20 wherein said single chain protein comprises a G28-1 single chain Fv binding domain polypeptide.

22. The pharmaceutical composition of claim 1, 3, 5, 6, 18 or 21, wherein the single chain protein promotes antibody dependent cell-mediated cytotoxicity or complement fixation or both.

23. The pharmaceutical composition of claim 1, 3, 5, 6, 18 or 21, wherein the binding domain polypeptide is humanized.

* * * * *